US011213683B2

(12) United States Patent
Miller et al.

(10) Patent No.: US 11,213,683 B2
(45) Date of Patent: Jan. 4, 2022

(54) SYSTEMS AND METHODS FOR SELECTIVE MEMORY ENHANCEMENT AND/OR DISRUPTION

(71) Applicant: Massachusetts Institute of Technology, Cambridge, MA (US)

(72) Inventors: Earl K. Miller, Somerville, MA (US); Scott L. Brincat, Cambridge, MA (US)

(73) Assignee: Massachusetts Institute of Technology, Cambridge, MA (US)

( * ) Notice: Subject to any disclaimer, the term of this patent is extended or adjusted under 35 U.S.C. 154(b) by 883 days.

(21) Appl. No.: 15/676,880

(22) Filed: Aug. 14, 2017

(65) Prior Publication Data

US 2018/0028813 A1 Feb. 1, 2018

Related U.S. Application Data

(63) Continuation of application No. PCT/US2016/018700, filed on Feb. 19, 2016.
(Continued)

(51) Int. Cl.
*A61N 1/36* (2006.01)
*A61N 1/04* (2006.01)
(Continued)

(52) U.S. Cl.
CPC ....... *A61N 1/36082* (2013.01); *A61N 1/0456* (2013.01); *A61N 1/0529* (2013.01);
(Continued)

(58) Field of Classification Search
CPC ................................ A61N 1/36025
See application file for complete search history.

(56) References Cited

U.S. PATENT DOCUMENTS 10,307,592 B1 * 6/2019 Pilly .................. A61B 5/4812
2008/0004660 A1    1/2008 Assaf et al.
(Continued)

OTHER PUBLICATIONS

Haddadi et al., Neurofeedback Training to Enhance Learning and Memory in Patient's with Cognitive Impairment, 2011, Procedia—Social and Behavioral Sciences, 30, 608-610. (Year: 2011).*
(Continued)

*Primary Examiner* — Rex R Holmes
*Assistant Examiner* — Jennifer L Ghand
(74) *Attorney, Agent, or Firm* — Smith Baluch LLP

(57) ABSTRACT

Systems and methods are disclosed for selectively reinforcing or weakening memory associations. At least one current generator provides an electrical current including a plurality of oscillating pulses with at least one predetermined frequency. A user interface includes at least one output device for delivering a sensory stimulus to a user and at least one user input device for registering a response to the stimulus. At least one processor determines from the response, based on at least one predetermined standard, whether an underlying memory association is desired or undesired and respectively sets the at least one predetermined frequency to be a beta or theta frequency. Consequently, the electrical current is generated and administered, via at least one electrode pair, thereby stimulating at least one specific portion of the user's brain so as to reinforce or weaken the underlying memory association.

31 Claims, 35 Drawing Sheets

Related U.S. Application Data

(60) Provisional application No. 62/118,190, filed on Feb. 19, 2015.

(51) Int. Cl.
    *A61N 1/05*    (2006.01)
    *A61N 1/372*    (2006.01)

(52) U.S. Cl.
    CPC ..... *A61N 1/36025* (2013.01); *A61N 1/36146* (2013.01); *A61N 1/36196* (2013.01); *A61N 1/37247* (2013.01)

(56) References Cited

U.S. PATENT DOCUMENTS

| | | |
|---|---|---|
| 2008/0269840 A1 | 10/2008 | Scott et al. |
| 2011/0319975 A1 | 12/2011 | Ho et al. |
| 2012/0071947 A1 | 3/2012 | Gupta et al. |
| 2012/0101147 A1 | 4/2012 | Tsai et al. |
| 2013/0184781 A1 | 7/2013 | Eskandar et al. |
| 2013/0190556 A1 | 7/2013 | Wetmore et al. |
| 2013/0245714 A1 | 9/2013 | Gupta et al. |
| 2014/0172041 A1 | 6/2014 | Draghici et al. |
| 2014/0272826 A1 | 9/2014 | Wilkins et al. |
| 2019/0247662 A1* | 8/2019 | Poltroak ................ A61B 5/246 |

OTHER PUBLICATIONS

Luu et al. Frontal midline theta and the error-related negativity: neurophysiological mechanisms of action regulation. Clin. Neurophysiol. 115, 1821-1835 (2004).
Matsumoto et al. Lateral habenula as a source of negative reward signals in dopamine neurons. Nature 447, 1111-1115 (2007).
McKenzie et al. Hippocampal Representation of Related and Opposing Memories Develop within Distinct, Hierarchically Organized Neural Schemas. Neuron 83, 202-215 (2014).
Merletti et al. Standards for reporting EMG data. J Electromyogr Kinesiol 9, 3-4 (1999).
Messinger et al. Neuronal representations of stimulus associations develop in the temporal lobe during learning. Proc. Natl. Acad. Sci. 98, 12239-12244 (2001).
Miller et al. Habituation-like decrease in the responses of neurons in inferior temporal cortex of the macaque. Vis. Neurosci. 7, 357-362 (1991).
Morf et al. Recursive multichannel maximum entropy spectral estimation. Geosci. Electron. IEEE Trans. 16, 85-94(1978).
Murray et al. Neural substrates of visual stimulus-stimulus association in rhesus monkeys. J. Neurosci. 13, 4549-4561 (1993).
Nassar et al. Rational regulation of learning dynamics by pupil-linked arousal systems. Nat. Neurosci. 15, 1040-1046 (2012).
Nelson et al. Review of signal distortion through metal microelectrode recording circuits and filters. J. Neurosci. Methods 169, 141-157 (2008).
Olejnik et al. Generalized Eta and Omega Squared Statistics: Measures of Effect Size for Some Common Research Designs. Psychological Methods 8, 434-447 (2003).
Oostenveld et al. FieldTrip: Open Source Software for Advanced Analysis of MEG, EEG, and Invasive Electrophysiological Data. Comput. Intell. Neurosci. 2011, 1-9 (2011).
Rainer et al. Prospective coding for objects in primate prefrontal cortex. J. Neurosci. 19, 5493-5505 (1999).
Rigotti et al. The importance of mixed selectivity in complex cognitive tasks. Nature 497, 585-590 (2013).
Sakai et al. Neural organization for the long-term memory of paired associates. Nature 354, 152-155 (1991).
Schoffelen. Neuronal Coherence as a Mechanism of Effective Corticospinal Interaction. Science 308, 111-113 (2005).
Schultz et al. Predictive reward signal of dopamine neurons. J. Neurophysiol. 80, 1-27 (1998).
Scoville et al. Loss of Recent Memory After Bilateral Hippocampal Lesions. J. Neurol. Neurosurg. Psychiatry 20, 11-21 (1957).
Shepherd et al. Facial Muscle Coordination in Monkeys during Rhythmic Facial Expressions and Ingestive Movements. J. Neurosci. 32, 6105-6116 (2012).
Siapas et al. Coordinated interactions between hippocampal ripples and cortical spindles during slow-wave sleep. Neuron 21, 1123-1128 (1998).
Siegel et al. Phase-dependent neuronal coding of objects in short-term memory. Proc. Natl. Acad. Sci. 106, 21341-21346 (2009).
Skaggs et al. EEEG Sharp Waves and Sparse Ensemble Unit Activity in the Macaque Hippocampus. J. Neurophysiol. 98, 898-910 (2007).
Sperling et al. Encoding novel face-name associations: A functional MRI study. Hum. Brain Mapp. 14, 129-139 (2001).
Squire et al. The medial temporal lobe. Annu. Rev. Neurosci. 27, 279-306 (2004).
Stokes et al. et al. Dynamic Coding for Cognitive Control in Prefrontal Cortex. Neuron 78, 364-375 (2013).
Torrence et al. A practical guide to wavelet analysis. Bull. Am. Meteorol. Soc. 79, 61-78 (1998).
Vinck et al. The pairwise phase consistency: A bias-free measure of rhythmic neuronal synchronization. NeuroImage 51, 112-122 (2010).
Wirth et al. Single neurons in the monkey hippocampus and learning of new associations. Science 300, 1578-1581 (2003).
Wirth et al. Trial Outcome and Associative Learning Signals in the Monkey Hippocampus. Neuron 61, 930-940 (2009).
Xiang et al. Neuronal responses related to long-term recognition memory processes in prefrontal cortex. Neuron 42, 817-829 (2004).
Yanike et al. Comparison of Associative Learning-Related Signals in the Macaque Perirhinal Cortex and Hippocampus. Cereb. Cortex 19, 1064-1078 (2009).
Abe et al. Reward Improves Long-Term Retention of a Motor Memory through Induction of Offline Memory Gains. Curr. Biol. 21, 557-562 (2011).
Baccalá et al. Generalized partial directed coherence in Digital Signal Processing, 2007 15th International Conference in Digit. Signal Process 163-166 (2007) at <http://ieeexplore.ieee.org/xpls/abs_all.jsp?arnumber=4288544>.
Bethus. Dopamine and Memory: Modulation of the Persistence of Memory for Novel Hippocampal NMDA Receptor-Dependent Paired Associates. J. Neurosci. 30, 1610-1618 (2010).
Bokil et al. Chronux: A platform for analyzing neural signals. Journal of Neuroscience Methods 192, 146-151 (2010).
Bunsey et al. Conservation of memory function in rats and humans. Nature 379, 255-257 (1996).
Buschman et al. Top-Down Versus Bottom-Up Control of Attention in the Prefrontal and Posterior Parietal Cortices. Science 315, 1860-1862 (2007).
Buzsaki et al. Memory, navigation and theta rhythm in the hippocampal-entorhinal system. Nat. Neurosci. 16, 130-138 (2013).
Buzsaki et al. Neuronal Oscillations in Cortical Networks. Science 304, 1926-1929 (2004).
Cohen et al. Preserved Learning and Retention of Pattern-Analyzing Skill in Amnesia: Dissociation of Knowing How and Knowing That. Science 210, 207-210 (1980).
Colgin et al. Understanding memory through hippocampal remapping. Trends Neurosci. 31, 469-477 (2008).
Cromer et al. Rapid association learning in the primate prefrontal cortex in the absence of behavioral reversals. J. Cogn. Neurosci. 23, 1823-1828 (2011).
Cui et al. BSMART: A Matlab/C toolbox for analysis of multichannel neural time series. Neural Netw. 21, 1094-1104 (2008).
Ding et al. Short-window spectral analysis of cortical event-related potentials by adaptive multivariate autoregressive modeling: data preprocessing, model validation, and variability assessment. Biol. Cybern. 83, 35-45 (2000).
Dudek et al. Homosynaptic long-term depression in area CA1 of hippocampus and effects of N-methyl-D-aspartate receptor blockade. Proc. Natl. Acad. Sci. 89, 4363—4367 (1992).
Düzel et al. Brain oscillations and memory. Curr. Opin. Neurobiol. 20, 143-149 (2010).

(56) References Cited

OTHER PUBLICATIONS

Eichenbaum et al. The hippocampus, memory, and place cells: Is it spatial memory or a memory space? Neuron 23, 209-226 (1999).
Eichenbaum et al. Towards a functional organization of episodic memory in the medial temporal lobe. Neurosci. Biobehav. Rev. 36, 1597-1608 (2012).
Engel et al. Beta-band oscillations—signalling the status quo? Curr. Opin. Neurobiol. 20, 156-165 (2010).
Erickson et al. Responses of macaque perirhinal neurons during and after visual stimulus association learning. J. Neurosci. 19, 10404-10416 (1999).
Farovik et al. Medial Prefrontal Cortex Supports Recollection, but Not Familiarity, in the Rat. J. Neurosci. 28, 13428-13434 (2008).
Fell et al. The role of phase synchronization in memory processes. Nat. Rev. Neurosci. 12, 105-118 (2011).
Fries. A mechanism for cognitive dynamics: neuronal communication through neuronal coherence. Trends Cogn. Sci. 9, 474-480 (2005).
Funahashi et al. Mnemonic coding of visual space in the monkey's dorsolateral prefrontal cortex. J Neurophysiol 61, 331-349 (1989).
Gallistel et al. The learning curve: Implications of a quantitative analysis. Proc. Natl. Acad. Sci. U. S. A. 101, 13124-13131 (2004).
Geweke. Measurement of linear dependence and feedback between multiple time series. J. Am. Stat. Assoc. 77, 304-313 (1982).
Granger et al. Investigating causal relations by econometric models and cross-spectral methods. Econ. J. Econ. Soc. 424-438 (1969).
Gutnikov et al. Temporo-frontal Disconnection Impairs Visual-visual Paired Association Learning but not Configural Learning in Macaca Monkeys. Eur. J. Neurosci. 9, 1524-1529 (1997).
Hess et al. Pupil size as related to interest value of visual stimuli. Science 132, 349-350 (1960).
Histed et al. Learning Substrates in the Primate Prefrontal Cortex and Striatum: Sustained Activity Related to Successful Actions. Neuron 63, 244-253 (2009).
Hyman et al. Medial prefrontal cortex cells show dynamic modulation with the hippocampal theta rhythm dependent on behavior. Hippocampus 15, 739-749 (2005).
International Search Report and Written Opinion dated Apr. 29, 2016 for International Application No. PCT/US2016/018700, 26 pages.
Jones et al. Theta Rhythms Coordinate Hippocampal-Prefrontal Interactions in a Spatial Memory Task. PLoS Biol. 3, e402 (2005), 13 pages.
Jutras et al. Gamma-Band Synchronization in the Macaque Hippocampus and Memory Formation. J. Neurosci. 29, 12521-12531 (2009).
Kalcher et al. Discrimination between phase-locked and non-phase-locked event-related EEG activity. Electroencephalogr. Clin. Neurophysiol. 94, 381-384 (1995).
Kennerley et al. Reward-Dependent Modulation of Working Memory in Lateral Prefrontal Cortex. J. Neurosci. 29, 3259-3270 (2009).
Kim. Neural activity that predicts subsequent memory and forgetting: A meta-analysis of 74 fMRI studies. NeuroImage 54, 2446-2461 (2011).
Komorowski et al. Robust Conjunctive Item-Place Coding by Hippocampal Neurons Parallels Learning What Happens Where. J. Neurosci. 29, 9918-9929 (2009).
Kopell et al. Gamma rhythms and beta rhythms have different synchronization properties. Proc. Natl. Acad. Sci. 97, 1867-1872 (2000).
Lachaux et al. Measuring Phase Synchrony in Brain Signals. Human Brain Mapping 8, 194-208 (1999).
Leutgeb et al. Pattern Separation in the Dentate Gyrus and CA3 of the Hippocampus. Science 315, 961-966 (2007).

* cited by examiner

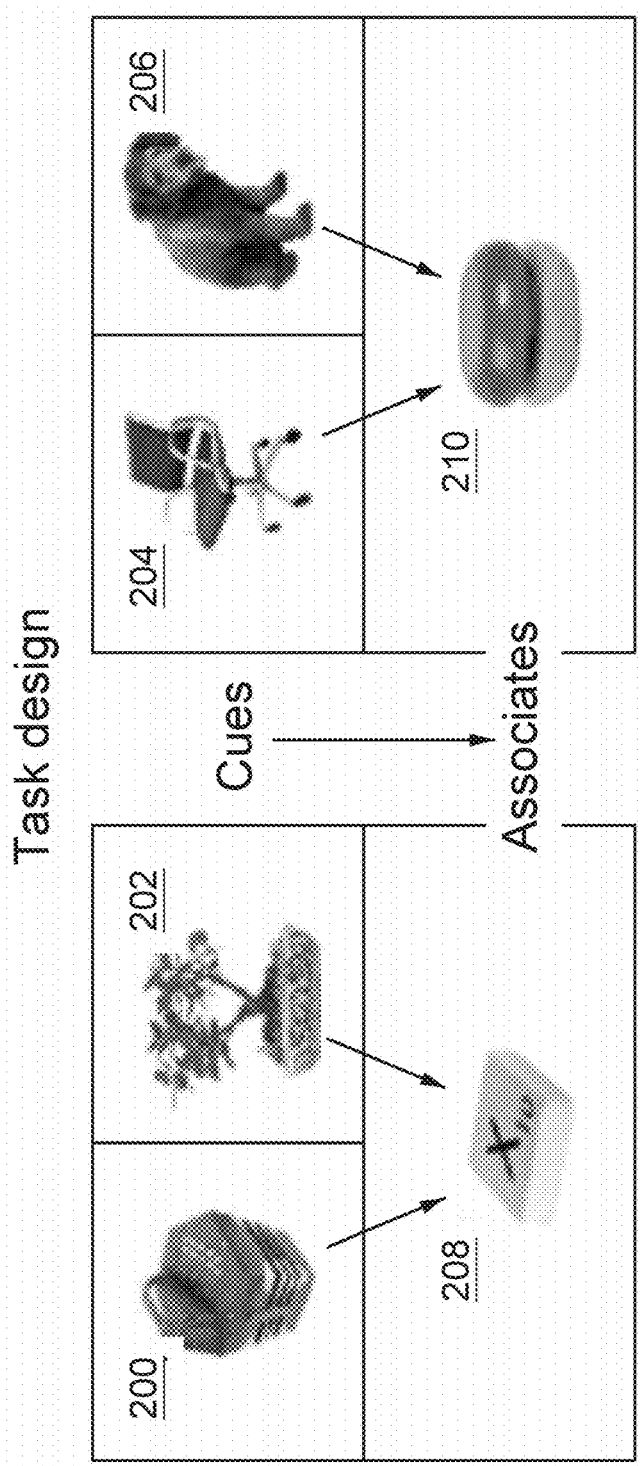

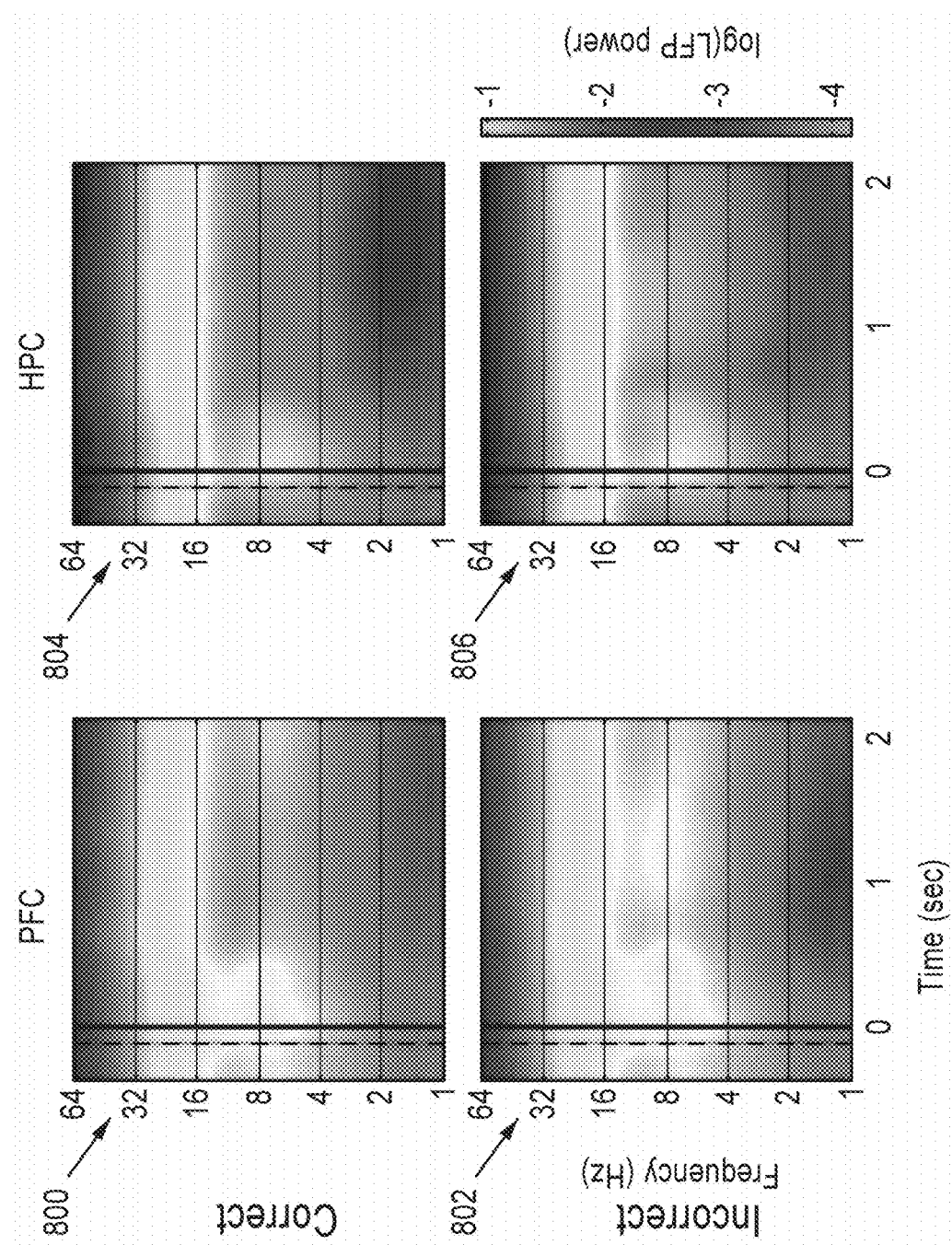

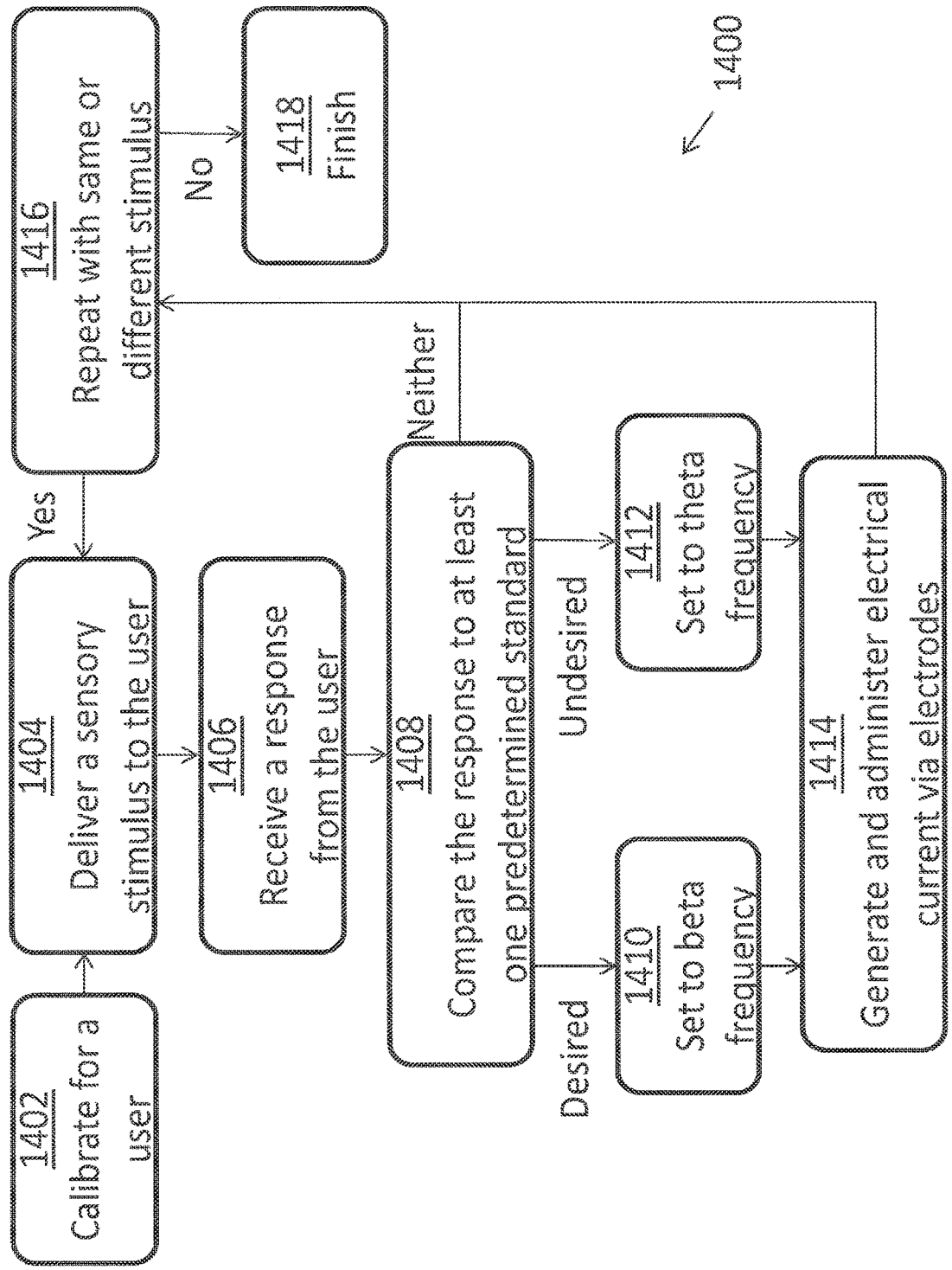

SYSTEMS AND METHODS FOR SELECTIVE MEMORY ENHANCEMENT AND/OR DISRUPTION

CROSS-REFERENCE TO RELATED APPLICATIONS

This application is a bypass continuation of International Application No. PCT/US2016/018700, entitled "Systems and Methods for Selective Memory Enhancement and/or Disruption" and filed Feb. 19, 2016, which claims priority to U.S. Application No. 62/118,190, entitled "Systems and Methods for Selective Memory Enhancement or Disruption" and filed Feb. 19, 2015. Each of these applications is hereby incorporated by reference in its entirety.

GOVERNMENT SUPPORT STATEMENT

This invention was made with Government support under Grant No. MH065252 awarded by the National Institutes of Health. The Government has certain rights in the invention.

TECHNICAL FIELD

The present disclosure relates generally to systems and methods for selectively reinforcing some memory associations and/or selectively weakening different memory associations. More specifically, the present disclosure relates to systems and methods for electrically stimulating the brain to enhance and/or disrupt memory formation, storage, and reconsolidation.

BACKGROUND

Much of our knowledge of the world and our ability to function within it depends on our ability to receive, store, and recall arbitrary associations. For example, we form memories to associate faces with names, words with meanings, and consequences with behaviors. Memory failures, such as forgetting or making incorrect associations, may be caused by a lack of attention during the receipt or storage of the correct association, a natural degradation of the association over time, a learning disability, or a memory loss disorder (e.g., amnesia or Alzheimer's disease). However, even a "correct" memory association (of, e.g., an intrusive a traumatic experience or fear conditioning) may be detrimental to normal functioning as a result of stress (e.g., post-traumatic stress disorder) or a memory disorder (e.g., hyperthymesia).

Existing treatments for enhancing or disrupting memory are ineffective, expensive, and/or dangerous. Furthermore, existing treatments are not selective as to which memory associations may be affected. For example, shock treatment not only has severe side effects but also disrupts all recent memories, not just undesired memory associations. Meanwhile, drugs, supplements, nutraceuticals, and functional foods offer neither proven effectiveness nor selectivity. In fact, many nootropics like amphetamines or other stimulants are associated with adverse effects and a relatively narrow therapeutic window (i.e., a high overdose risk). Likewise, antidepressants and anti-anxiety medications may help mitigate some symptoms of memory-related stress but at the cost of adverse side effects and potential for abuse.

SUMMARY

At least two parts of the brain are important for memory storage, namely the prefrontal cortex (PFC) and the hippocampus (HPC). Through research and analysis, the inventors have determined that the PFC and the HPC synchronize their oscillations at specific frequencies when memory associations are formed. For example, when a subject forms a correct memory association, oscillations in the PFC and the HPC synchronize at beta frequencies. However, when a subject makes a mistake or attempts to form an incorrect memory association, oscillations in the PFC and the HPC synchronize at theta frequencies. Thus, beta synchrony indicates to the brain that the subject should "store" the correct memory association, while theta synchrony indicates to the brain that the subject should "forget" the incorrect memory association.

The inventors have further recognized and appreciated that the external application of synchronized oscillations may be used to train the brain to reinforce and/or weaken associations during memory formation and/or reconsolidation. For example, oscillations with beta frequencies may be applied to artificially create beta synchrony between the PFC and the HPC, and oscillations with theta frequencies may be applied to artificially create theta synchrony between the PFC and the HPC.

According to some embodiments, electrical stimulation is applied to the brain (e.g., through electrodes in substantial contact with the scalp). For example, the electrical stimulation may be safely applied to the PFC and the HPC using low-voltage transcranial electrical stimulation (TES). TES involves passing a very low current between electrodes and has been used to pass a constant current (DC). Brain activity naturally waxes and wanes in phase with endogenous rhythms. By adapting TES to use an oscillating current (AC) to enhance these rhythms, the inventors have recognized and appreciated that TES may be used to enhance specific brain activities in a more precise, physiological manner (i.e., by selectively administering electrical currents oscillating at beta frequencies and/or theta frequencies).

In one embodiment, a system for selectively reinforcing or weakening memory associations includes at least one current generator for providing an electrical current. The electrical current may include a plurality of oscillating pulses with at least one predetermined frequency. The system may include a user interface, including at least one output device for delivering at least one sensory stimulus to a user, at least one user input device for registering at least one response of the user to the at least one sensory stimulus, and at least one electrode pair for detachable attachment to or proximate to the user's scalp. The at least one electrode pair may be configured to stimulate at least one specific portion of the user's brain with the electrical current based at least in part on the at least one response of the user to the at least one sensory stimulus. The system may include at least one memory for storing processor-executable instructions and at least one processor communicatively coupled to the at least one current generator, the user interface, and the at least one memory. Upon execution of the processor-executable instructions by the at least one processor, the at least one processor may control the user interface to deliver a first sensory stimulus to the user and register the at least one response of the user to the first sensory stimulus, process the at least one response of the user to the first sensory stimulus to determine whether an underlying memory association is desired or undesired according to at least one predetermined standard, set the at least one predetermined frequency to be a beta frequency if the underlying memory association is desired or a theta frequency if the underlying memory association is undesired, control the at least one current generator to generate the electrical current with the beta frequency or the theta frequency, and control the user interface to administer the electrical current, via the at least one electrode pair, thereby stimulating the at least one specific portion of the user's brain with the electrical current based at least in part on the at least one response of the user to the first sensory stimulus so as to reinforce or weaken the underlying memory association.

In another embodiment, a system for selectively weakening memory associations includes at least one current generator for providing an electrical current. The electrical current may include a plurality of oscillating pulses with at least one predetermined frequency. The system may include a user interface, including at least one output device for delivering at least one sensory stimulus to a user, at least one user input device for registering at least one response of the user to the at least one sensory stimulus, and at least one electrode pair for detachable attachment to or proximate to the user's scalp. The at least one electrode pair may be configured to stimulate at least one specific portion of the user's brain with the electrical current based at least in part on the at least one response of the user to the at least one sensory stimulus. The system may include at least one memory for storing processor-executable instructions, and at least one processor communicatively coupled to the at least one current generator, the user interface, and the at least one memory. Upon execution of the processor-executable instructions by the at least one processor, the at least one processor may control the user interface to deliver a first sensory stimulus to the user and register the at least one response of the user to the first sensory stimulus, and process the at least one response of the user to the first sensory stimulus to determine whether an underlying memory association is undesired according to at least one predetermined standard. If the underlying memory association is undesired, the at least one processor may set the at least one predetermined frequency to be a theta frequency, control the at least one current generator to generate the electrical current with the theta frequency, and control the user interface to administer the electrical current, via the at least one electrode pair, thereby stimulating the at least one specific portion of the user's brain with the electrical current based at least in part on the at least one response of the user to the first sensory stimulus so as to weaken the underlying memory association.

In an embodiment, a system for selectively reinforcing memory associations includes at least one current generator for providing an electrical current. The electrical current may include a plurality of oscillating pulses with at least one predetermined frequency. The system may include a user interface, including at least one output device for delivering at least one sensory stimulus to a user, at least one user input device for registering at least one response of the user to the at least one sensory stimulus, and at least one electrode pair for detachable attachment to or proximate to the user's scalp. The at least one electrode pair may be configured to stimulate at least one specific portion of the user's brain with the electrical current based at least in part on the at least one response of the user to the at least one sensory stimulus. The system may include at least one memory for storing processor-executable instructions, and at least one processor communicatively coupled to the at least one current generator, the user interface, and the at least one memory. Upon execution of the processor-executable instructions by the at least one processor, the at least one processor may control the user interface to deliver a first sensory stimulus to the user and register the at least one response of the user to the first sensory stimulus, and may process the at least one response of the user to the first sensory stimulus to determine whether an underlying memory association is desired according to at least one predetermined standard. If the underlying memory association is desired, the at least one processor may set the at least one predetermined frequency to be a beta frequency. Then, the at least one processor may control the at least one current generator to generate the electrical current with the beta frequency and the user interface to administer the electrical current, via the at least one electrode pair, thereby stimulating the at least one specific portion of the user's brain with the electrical current based at least in part on the at least one response of the user to the first sensory stimulus so as to reinforce the underlying memory association.

In an embodiment, a method for selectively reinforcing or weakening memory associations includes delivering, via at least one output device, a first sensory stimulus to a user, registering, via at least one user input device, at least one response of the user to the first sensory stimulus, processing, via at least one processor in communication with the at least one output device and the at least one input device, the at least one response of the user to the first sensory stimulus to determine whether an underlying memory association is desired or undesired according to at least one predetermined standard, generating, via at least one current generator in communication with the at least one processor, an electrical current, the electrical current including a plurality of oscillating pulses with at least one predetermined frequency, the at least one predetermined frequency being set to a beta frequency if the underlying memory association is desired or a theta frequency if the underlying memory association is undesired, and administering the electrical current, via at least one electrode pair detachably attached to or proximate to the user's scalp, to stimulate at least one specific portion of the user's brain with the electrical current based at least in part on the at least one response of the user to the first sensory stimulus so as to reinforce or weaken the underlying memory association.

In an embodiment, a method for selectively weakening memory associations includes delivering, via at least one output device, a first sensory stimulus to a user, registering, via at least one user input device, at least one response of the user to the first sensory stimulus, processing, via at least one processor in communication with the at least one output device and the at least one input device, the at least one response of the user to the first sensory stimulus to determine whether an underlying memory association is undesired according to at least one predetermined standard, and if the underlying memory association is undesired, generating, via at least one current generator in communication with the at least one processor, an electrical current, the electrical current including a plurality of oscillating pulses with at least one predetermined frequency, the at least one predetermined frequency being set to a theta frequency, and administering the electrical current, via at least one electrode pair detachably attached to or proximate to the user's scalp, to stimulate at least one specific portion of the user's brain with the electrical current based at least in part on the at least one response of the user to the first sensory stimulus so as to weaken the underlying memory association.

In an embodiment, a method for selectively reinforcing memory associations includes delivering, via at least one output device, a first sensory stimulus to a user, registering, via at least one user input device, at least one response of the user to the first sensory stimulus, processing, via at least one processor in communication with the at least one output device and the at least one input device, the at least one response of the user to the first sensory stimulus to determine whether an underlying memory association is desired according to at least one predetermined standard, and if the underlying memory association is desired, generating, via at least one current generator in communication with the at least one processor, an electrical current, the electrical current including a plurality of oscillating pulses with at least one predetermined frequency, the at least one predetermined frequency being set to a beta frequency, and administering the electrical current, via at least one electrode pair detachably attached to or proximate to the user's scalp, to stimulate at least one specific portion of the user's brain with the electrical current based at least in part on the at least one response of the user to the first sensory stimulus so as to reinforce the underlying memory association.

The at least one output device for delivering the at least one sensory stimulus to the user may include a visual display, a printer, a refreshable tactile display, and/or a speaker. The at least one sensory stimulus may include a digital image, an alphanumeric character, a braille character, and/or an audible sound. The at least one sensory stimulus may include an objective assessment question that requires the user to select, via the at least one input device, an indication of true or false, an answer from a plurality of presented answers, or a match from a plurality of presented matches. The at least one sensory stimulus may include an objective assessment question that requires the user to supply at least one of an alphanumeric character, a braille character, and an audible sound via the at least one input device.

The at least one input device for registering at least one response of the user to the at least one sensory stimulus may include a keyboard, a scanner, a microphone, a pointing device, a touchscreen, a webcam, and/or a refreshable tactile display. The at least one response of the user to the at least one sensory stimulus may be a selection of an indication of true or false, a selection of an answer from a plurality of presented answers, or a selection of a match from a plurality of presented matches. The at least one response of the user to the at least one sensory stimulus may be an alphanumeric character, a braille character, and/or an audible sound.

Some embodiments may include at least one sensor for at least one of detecting and measuring at least one physiological input signal from the user. The at least one sensor may be in addition to the at least one input device for registering the at least one response of the user to the at least one sensory stimulus, at least one sensor for at least one of detecting and measuring at least one physiological input signal from the user. The system may also include an analog-to-digital converter coupled to the at least one sensor for electronically converting the at least one physiological input signal from the at least one sensor to a plurality of digital samples of the at least one physiologic signal relating to at least one physiological parameter.

The at least one input device for registering the at least one response of the user to the at least one sensory stimulus may include at least one sensor for at least one of detecting and measuring at least one physiological input signal from the user. The at least one input device may include a heart rate monitor, an ECG system, a blood pressure monitor, a respiration rate monitor, a thermometer, an fMRI system, an EEG system, and/or an MEG system. The at least one response of the user to the at least one sensory stimulus may relate to a change in a physiological parameter of the user. The physiological parameter may relate to the user's heart rate, blood pressure, body temperature, respiration rate, neural activation, and/or neural oscillation.

Some embodiment include selecting, calibrating, and/or customizing for the user the at least one output device, the at least one input device, a placement of the at least one electrode pair, a type of the first sensory stimulus, a content of the first sensory stimulus, a type of the at least one response to the first sensory stimulus, the at least one predetermined standard, an amplitude of the electrical current, and the at least one predetermined frequency.

The at least one specific portion of the user's brain may include the prefrontal cortex, the hippocampus, associated structures of the limbic system, or some combination thereof.

The at least one electrode pair may be a plurality of electrode pairs. Each electrode of the at least one electrode pair may be a transcranial electrode and/or an alternating current electrode. A conductive gel and/or paste may be used to reduce impedance between each electrode of the at least one electrode pair and the user's scalp. Wiring may be used to connect each electrode of the at least one electrode pair to the at least one current generator. Some embodiments may include attaching the at least one electrode pair to or proximate to the user's scalp, applying a conductive gel and/or paste between each electrode of the at least one electrode pair and the user's scalp, and/or attaching connecting each electrode of the at least one electrode pair to the at least one current generator.

Some embodiments may include a low voltage power source for the current generator. The low voltage power source may supply about 5-20 volts. The electrical current may have a current flow of about 0.25-1.5 milli-amps. The frequency and/or an amplitude of the electrical current may be regulated by, for example, the at least one processor.

Determining whether an underlying memory association is desired or undesired may include comparing the at least one response of the user to the at least one predetermined standard. The at least one predetermined standard may include a correct response to an associated sensory stimulus, a response time, a magnitude of a physiological parameter of the user, and/or a frequency of a physiological parameter of the user.

The beta frequency may be a frequency between about 12 Hz and about 40 Hz. For example, the beta frequency may be about 16 Hz. The theta frequency may be a frequency between about 3 Hz and about 8 Hz. For example, the theta frequency may be about 4 Hz.

Some embodiments may be used for computer-based learning and/or to administer treatment to a patient with a learning disability, a memory disorder, and/or a stress disorder.

It should be appreciated that all combinations of the foregoing concepts and additional concepts discussed in greater detail below (provided such concepts are not mutually inconsistent) are contemplated as being part of the inventive subject matter disclosed herein. In particular, all combinations of claimed subject matter appearing at the end of this disclosure are contemplated as being part of the inventive subject matter disclosed herein. It should also be appreciated that terminology explicitly employed herein that also may appear in any disclosure incorporated by reference should be accorded a meaning most consistent with the particular concepts disclosed herein.

Other systems, processes, and features will become apparent to those skilled in the art upon examination of the following drawings and detailed description. It is intended that all such additional systems, processes, and features be included within this description, be within the scope of the present invention, and be protected by the accompanying claims.

BRIEF DESCRIPTION OF THE DRAWINGS

The skilled artisan will understand that the drawings primarily are for illustrative purposes and are not intended to limit the scope of the inventive subject matter described herein. The drawings are not necessarily to scale; in some instances, various aspects of the inventive subject matter disclosed herein may be shown exaggerated or enlarged in the drawings to facilitate an understanding of different features. In the drawings, like reference characters generally refer to like features (e.g., functionally similar and/or structurally similar elements).

FIGS. 2A and 2B are diagrams illustrating a task trial design and a task trial sequence, primate learning performance, and different behavioral metrics, respectively, in accordance with some embodiments.

FIG. 8A is a series of mean log-transformed local field potential power spectrograms in PFC and HPC, respectively, in accordance with some embodiments.

FIG. 14 is a flow diagram illustrating a method for selectively reinforcing and/or weakening memory associations in accordance with some embodiments.

DETAILED DESCRIPTION

Figure 1A:
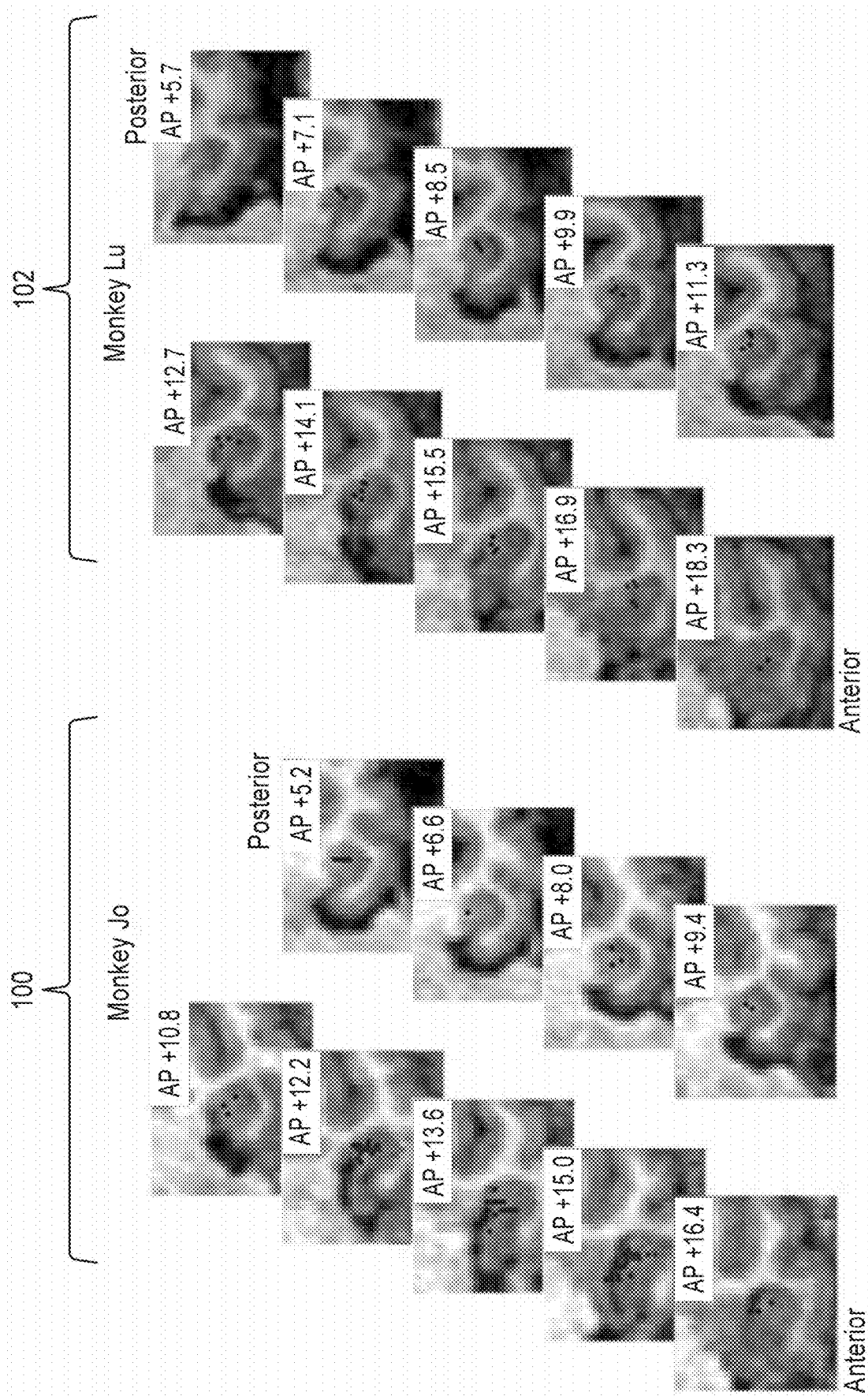
FIG. 1A is a diagram including anterior-to-posterior series of coronal MRI slices from hippocampal recording sites in two primate subjects, respectively, in accordance with some embodiments.

The present disclosure describes systems and methods for selectively reinforcing memory associations to enhance memory formation and/or storage. Systems and methods for selectively weakening memory associations to disrupt memory formation and/or storage are also described. According to some embodiments, systems and methods may be used to selectively reinforce some memory associations and selectively weaken different memory associations.

Memory can be categorized as explicit or implicit. Explicit memory involves deliberate conscious recollection of information, such as facts and specific personal experiences, whereas implicit memory involves unconscious recollection of information, such as skills. The recall of a specific foreign language lesson is an example of explicit memory, but speaking in the foreign language as a result of the lesson is an example of implicit memory. A subject encodes explicit memory by processing and reorganizing the data through associations with previous related stimuli or experiences. Later recall of the data depends at least in part on the way the data was initially encoded, for example, repetition, subsequent testing, emotional involvement, surroundings/cues, etc.

By tracing subsequent memory deficits in patients and animal models to neuroanatomical damage or irregularities, researchers have identified different areas of the brain associated with memory encoding, storage, and recollection. Depending on the type of memory, the PFC, the HPC, the amygdala, the striatum, the mammillary bodies, adjacent areas, and/or related pathways may be involved.

The HPC and the PFC are critical, especially in primates, for forming and consolidating memory associations, including non-spatial explicit memory. HPC damage causes memory loss and problems with memory storage, including deficits in non-spatial associative learning (if implicit memory cannot be used). The anatomy and role of the HPC is largely conserved across mammals with similar organization and neural pathways in humans and other mammal species. Likewise, PFC damage impairs non-spatial explicit memory (but appears to spare implicit memory).

At a cellular level, neurons maintain the brain's electrical charge by constantly exchanging ions with the extracellular space to maintain resting potential and to propagate action potentials. The electric potential of a single neuron is very small; however, during volume conduction, many ions are pushed out of many neurons with similar spatial orientation at the same time and a wave of ions is created. This synchronous electrical activity can be detected using, for example, electroencephalography (EEG) or magnetoencephalography (MEG). In EEG, multiple electrodes are placed on the subject's scalp to measure voltage fluctuations from these ionic current flows. Different types of neural oscillations may be observed in, for example, EEG signals. Neural oscillations vary in their frequency ranges, spatial distributions, and associations with different states of brain functioning. Frequency bands associated with neural oscillations have been delimited with some overlap depending on the source. For example, and according to some embodiments herein, theta frequencies range from about 3 Hz to about 8 Hz, and beta frequencies range from about 12 Hz to about 40 Hz. The relationship between neural oscillations and the underlying neuronal network is highly complex and often not well understood.

In humans, neuroimaging has demonstrated that both the HPC and the PFC are activated during associative memory processes. In rodents, theta-frequency synchrony has been detected between the HPC and the PFC during spatial memory performance, and high-frequency ripple synchrony has been detected during subsequent sleep, which is thought to reflect acquisition and integration, by the HPC, of spatial information into cortical networks for long-term storage.

In primates, spiking neuronal activity in the PFC—but not in the HPC—has reflected new learning in parallel with behavioral performance. The HPC neurons were instead most active following the behavioral response, reflecting feedback about whether trial-and-error guesses were correct (rewarded) or incorrect (not rewarded). Theta-frequency synchrony between the HPC and the PFC was stronger after errors, driven primarily by directional influences from the PFC to the HPC, and decreased with learning. In contrast, beta-frequency synchrony was stronger after correct trials, initially driven primarily by directional influences from the HPC to the PFC, and increased with learning, especially from the PFC to the HPC. Thus, rapid object associative learning may occur in the PFC while the HPC guides neocortical plasticity by signaling success or failure via oscillatory synchrony in different frequency bands.

Frequency-Specific Interactions Observed During Associative Learning

To examine the functional differences and frequency-specific interactions between the PFC and the HPC, an animal model of human explicit memory was defined for learning new arbitrary associations between object pairs. Monkeys were selected as subjects because their mnemonic and cognitive abilities are more akin to humans.

All experiments were performed in two adult rhesus macaques (*Macaca mulatta*), one male and one female, weighing 9 and 7.5 kg, respectively. Each monkey was implanted under general anesthesia with a titanium post for head restraint and two cylindrical 20-mm diameter titanium recording chambers. Chambers were stereotaxically placed over the PFC and the HPC in the left hemisphere based on coordinates from structural MRI scans in each monkey. All procedures followed the guidelines of the MIT Animal Care and Use Committee and the NIH.

Up to 16 microelectrodes in the PFC, and up to 4 in the HPC, were acutely inserted into the brain each day and removed at the end of each daily experiment. All recordings from the PFC, and most from the HPC, were performed with epoxy-coated tungsten microelectrodes (FHC). Some HPC recordings used 24-channel linear probes with 300 μm spacing between adjacent platinum-iridium recording contacts (e.g., U-Probes from Plexon Inc., Dallas, Tex.). For the PFC, electrodes were lowered through the dura using a custom-built screw microdrive assembly. For the HPC, electrodes were inserted through a 25 gauge transdural cannula using a motorized microdrive system (e.g., NAN-S4 from NAN Instruments Ltd., Nazareth, Israel).

Neural activity was amplified, filtered, digitized, and stored using an integrated multichannel recording system (Multichannel Acquisition Processor from Plexon Inc., Dallas, Tex.). The signal from each electrode was amplified by a high-input-impedance headstage (HST/8o50-G1 from Plexon Inc., Dallas, Tex.), then separately filtered to extract spiking activity (250-8000 Hz) and local field potentials (LFPs; 0.7-300 Hz). Both signals were referenced to ground, rather than to one of the electrodes, eliminating the possibility of artifactual synchrony due to neural signals measured by the reference itself. The spiking signal was threshold-triggered to separate neuronal spikes from background noise, and individual spike waveforms were digitized at 40 kHz and sorted offline into isolated neurons and multiunits using a combination of waveform shape and amplitude features (Offline Sorter from Plexon Inc., Dallas, Tex.). To minimize any sampling bias of neural activity, activity was not prescreened for responsiveness or task selectivity. Instead, electrodes were advanced until one or more neurons could be isolated, and then data collection began. Neurons were included in analyses only for the extent of time during which they were well isolated from background noise and other neurons. LFPs were recorded continuously at 1 kHz, and corrected offline for filtering-induced phase shifts (FPAlign Utility from Plexon Inc., Dallas, Tex.). Only LFPs from electrodes recording at least one neuron (isolated or multiunit) were used for all analyses, to ensure they were in the appropriate cell layer.

Electrodes were targeted using custom software written in the MATLAB® computing language and environment (available from The Mathworks, Inc. (Natick, Mass.)) that co-registered each monkey's implanted recording chambers and structural MRIs in stereotaxic coordinates, and re-sliced the MRIs along the electrode's path. The sequence of distinct neurophysiological compartments (gray matter, white matter, and sulcus/ventricle) along the electrode's path to HPC was compared online to these images. The HPC was also identified by its characteristic high-amplitude LFPs, low spike rates, and bursty spiking patterns. Recordings targeted dorsolateral and ventrolateral PFC, and all subregions (dentate gyrus/CA4, CA3, CA2, CA1, and subiculum) of about three fourths of the anterior of the hippocampal formation. For hippocampal subregion analyses, recordings were pooled across the dentate gyrus, CA3, and CA2 (HPC input/local-processing), and across CA1 and the subiculum (HPC output). A total of 496 PFC and 270 HPC neurons (156 from locally-projecting and 111 from output subregions) were recorded across all sessions.

FIG. 1A shows the hippocampal recording sites in a first monkey ("Jo") 100 and a second monkey ("Lu") 102, plotted on an anterior-to-posterior series of coronal MRI slices (labeled with mm relative to interaural line) in accordance with some embodiments. Each dot represents a location where neurons were recorded. Dark dots indicate locally-projecting subregions (dentate gyrus, CA3, CA2). Light dots indicate output subregions (CA1, subiculum). The recordings spanned all subregions of about three fourths of the anterior of the hippocampal formation.

Figure 1B:
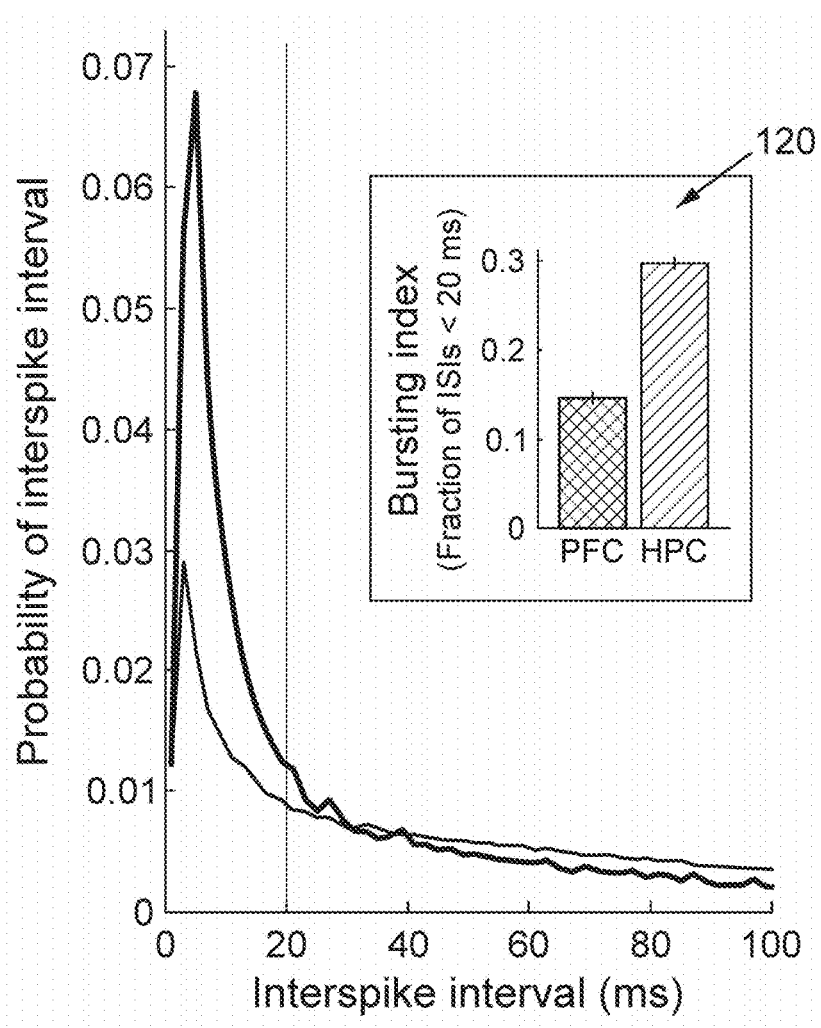
FIG. 1B is a plot illustrating the interspike interval (ISI) probability, including population mean ISI histograms showing each ISI averaged across all PFC and HPC putative principal neurons, in accordance with some embodiments.

Hippocampal neurons exhibit characteristic bursty firing. FIG. 1B is a plot of population mean (±SEM) interspike interval (ISI) histograms showing the probability of each ISI averaged across all PFC and HPC putative principal neurons (putative interneurons were discriminated based on spike waveform and firing rate, and excluded from this plot) in accordance with some embodiments. In the inset 120, population mean (±SEM) spike bursting index—the fraction of each neuron's ISIs is less than 20 ms. Both plots illustrate the distinctive burstiness of hippocampal units in comparison to neocortical units.

The monkeys were trained to perform a paired-associate learning task that required them to rapidly learn arbitrary associations between pairs of objects. For each daily recording session, six objects never before seen by the monkey were chosen from an image database (e.g., Hemera PhotoObjects available from BMSoftware (Norwich, UK)). FIG. 2A illustrates the task design in accordance with some embodiments. Like the example in FIG. 2A, four objects 200, 202, 204, 206 were randomly designated as cue objects, and each cue object was arbitrarily paired with one of the remaining two objects designated as associate objects 208, 210 for each daily session. The resulting many-to-one (4-to-2) mapping from cue objects to associate objects distinguished neural activity related to the cue from retrieval of its associate, and encouraged prospective recall of the associate before its appearance. The monkeys' task was to learn, through trial-and-error guessing, which associate object was paired with each cue object.

Figure 2B:
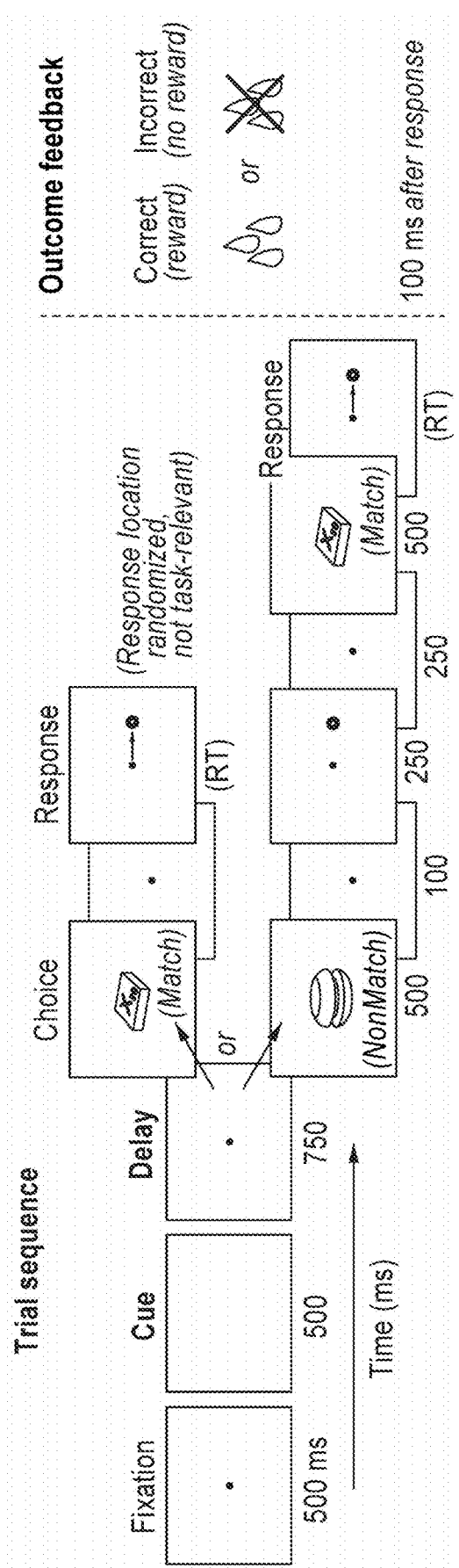

FIG. 2B illustrates the task trial sequence in accordance with some embodiments. Each trial started when the monkey acquired fixation of a white dot at the center of the stimulus screen. After a blank fixation baseline (500 ms), a cue object (foveal, 3° wide) was presented (500 ms), followed by a blank delay interval (750 ms) in which the monkey was expected to recall the paired associate object from memory. The two associate objects were then presented in a randomly-ordered series, with each presentation (500 ms) followed by a brief delay (100 ms) and a response target (250 ms; 7.5° to the left or right of fixation). The monkey was required to make a saccadic response to the target immediately following the correct paired associate for the given cue. Response to the correct associate was rewarded with juice and a short wait (3 s) until the subsequent trial. Response to the incorrect associate was punished by withholding reward, displaying a red "error screen" as secondary reinforcement (1.5 s), and a longer wait (6 s) for the subsequent trial. In FIG. 2B, the durations of each task period is indicated below the panels in ms, and "RT" represents reaction time. The location (left vs. right) of the response target after each associate was randomized and unrelated to task performance, so a specific motor plan could not be formed until the target was shown, and striatal-mediated procedural (stimulus-response) learning could not be used to correctly perform the task. Saccadic responses were used because their stereotypy obviates the possibility that changes in motor performance might be confounded with associative learning.

Each session began with a short block of 36 trials where the cue and associate objects for that day were passively presented to the monkey under fixation control (3 objects per trial at 500 ms each, 750 ms blank inter-stimulus interval), and a block of 96 identity match-to-sample trials in which each object was matched to itself, rather than to an arbitrary associate. These trials familiarized the monkeys with the stimuli, and eliminated any contribution of novelty-based or familiarity-based memory processes to the results.

Eye movements were monitored and recorded at 1 kHz using an infrared eye tracking system (using, e.g., EyeLink II available from SR Research Ltd. (Ottawa, Canada)). Fixation was required to be maintained within a 1.5° window around the fixation dot through the entire trial, until the response period; fixation breaks terminated the trial without reward. Behavioral monitoring and visual stimulus presentation were handled by the NIH CORTEX real-time control system, and displayed on a CRT monitor with a 100 Hz refresh rate.

Thus, during each daily session, the monkeys learned—through trial-and-error—four novel associations between pairs of objects across a few hundred trials. The monkeys routinely learned associations within a few hundred trials. Changes in behavior and neural activity across learning were measured by performing analyses independently in sliding trial windows, each defined by a percentile of the total number of session trials to normalize for differences in session length. Because the proportion of correct and incorrect trials changes with learning, their trial numbers were balanced for all analyses of trial outcome. First, for a given session, the smallest number of correct or incorrect trials in any trial window (usually incorrect trials late in learning) was identified. Then only this number of trials was randomly sampled from each outcome (correct or incorrect) within each trial window, the statistic of interest was calculated for this subsample of trials, and the resulting statistic was averaged across several random samplings to obtain a robust estimate.

To restrict analysis to only those sessions with successful learning, a learning criterion was set at 32 correct responses over the final 50 trials of each association ($p \approx 0.01$; binomial test). Only sessions where all four associations were learned to criterion were included in the reported analyses (61/87 sessions, including a total of 319 PFC and 199 HPC neurons [104 from locally-projecting and 93 from output subregions]). Trials in which no valid response was made (due to, e.g., fixation breaks, failures to respond, etc.) and sessions in which monkeys failed to learn all four associations were excluded from analysis.

Analyses focused on contrasts between (a) the recalled associate objects (signals reflecting associative learning), and (b) correct and incorrect trial outcomes (signals used to guide learning). For (a), analysis was temporally aligned to retrieval cue onset, and session trials were finely sampled via sliding trial windows. For (b), analysis was aligned to the outcome feedback (reward vs. no-reward) on each trial, and trial numbers were balanced across correct and incorrect outcomes, which necessitated coarser sampling of session trials. Correct and incorrect trial outcomes entail a number of perceptual differences that might affect neural activity (e.g., auditory click of reward solenoid, tactile/gustatory responses to juice reward). These distinctions remain constant across learning trials, however, so the analysis was focused on changes in activity with learning.

Significance testing was conducted using random resampling methods that make no assumptions about the data distribution. To test hypotheses that a statistic is distinct from a specified value (as in a 1-sample t-test), a bootstrap was used where the distribution of the statistic was estimated empirically by recalculating it repeatedly from random resamples-with-replacement of the observed data. The p value is the proportion of resampled values less than the specified comparison value (e.g., zero). To test hypotheses that a statistic takes different values for different groups (as in a 1-way ANOVA), permutation tests were used in which the null distribution reflecting no actual difference is estimated by repeatedly shuffling data values between groups. The p value is the proportion of shuffled values larger than the actual observed value. For comparisons involving two factors and their interaction (as in a 2-way ANOVA), group labels were shuffled across observations, maintaining any correlations between factors, but eliminating their correlation with experimental groups. The p value for each factor and interaction was calculated as above. At least 10,000 iterations were performed for each test. All analyses were performed using custom code written in MATLAB® (available from The MathWorks Inc. (Natick, Mass.)).

Behavioral learning curves were estimated in two ways. A sliding window analysis measured the percent of correct responses within a window of width equal to 10% of the total trials in a given session, stepped in 2.5% increments from the start to the end of the session. This permits identical trial sampling for behavioral and neural data analysis, but it underestimates learning rate due to the smoothing inherent in averaging across several abrupt, laterally-shifted learning curves. To estimate the true learning rate, binary outcomes (correct/incorrect) across trials were fit with a bounded logistic curve, as shown in Equation (1):

$$p = \alpha + \frac{b - \alpha}{1 + \exp\left(-\frac{x - \mu}{\sigma}\right)} \tag{1}$$

where the probability p of a correct response on each trial x is estimated as a sigmoidal learning curve with center $\mu$, width $\sigma$ (inversely related to learning rate), initial guess rate $\alpha$ (about 0.5 for the two-choice task), and post-learning asymptote b. These four parameters were fitted for each learned association using nonlinear least-squares estimation (e.g., the MATLAB® lsqnonlin function) with reasonable parameter bounds based on the data.

Figure 2C:
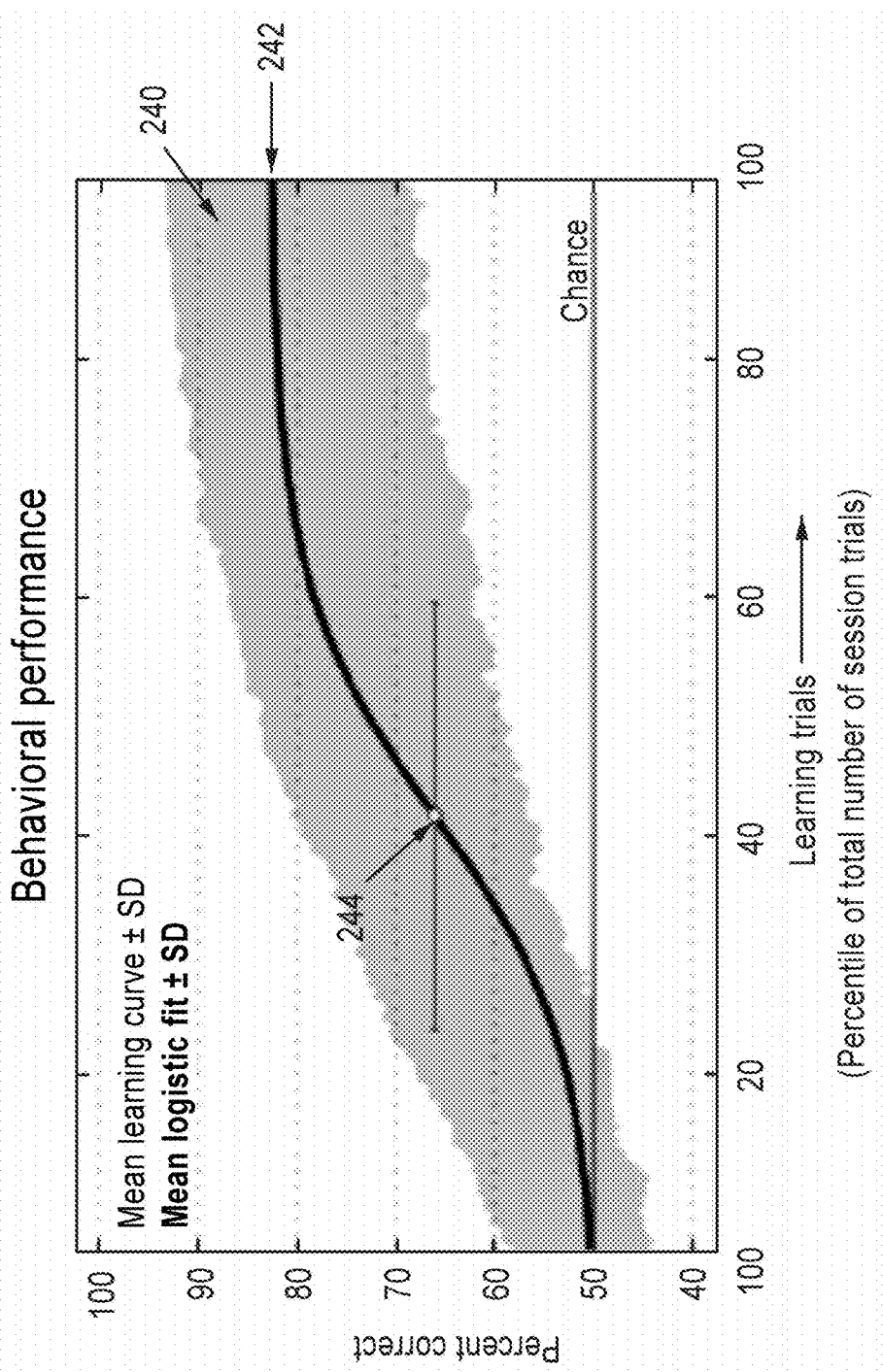
FIG. 2C is a plot illustrating primate learning performance in accordance with some embodiments.

FIG. 2C illustrates the monkeys' learning performance in accordance with some embodiments. The shaded area 240 is the mean±SD of logit-transformed percent correct performance across all 348 associations (87 sessions), plotted as a function of the percentile of each session's trials (mean±SD trials per session: 1117±125). Curve 242 is the average sigmoidal learning curve fit to each association. The white dot 244 is the mean±SD of fit curve centers. Of 348 associations, 313 associations were learned to criterion (p<0.01, binomial test).

Figure 2D:
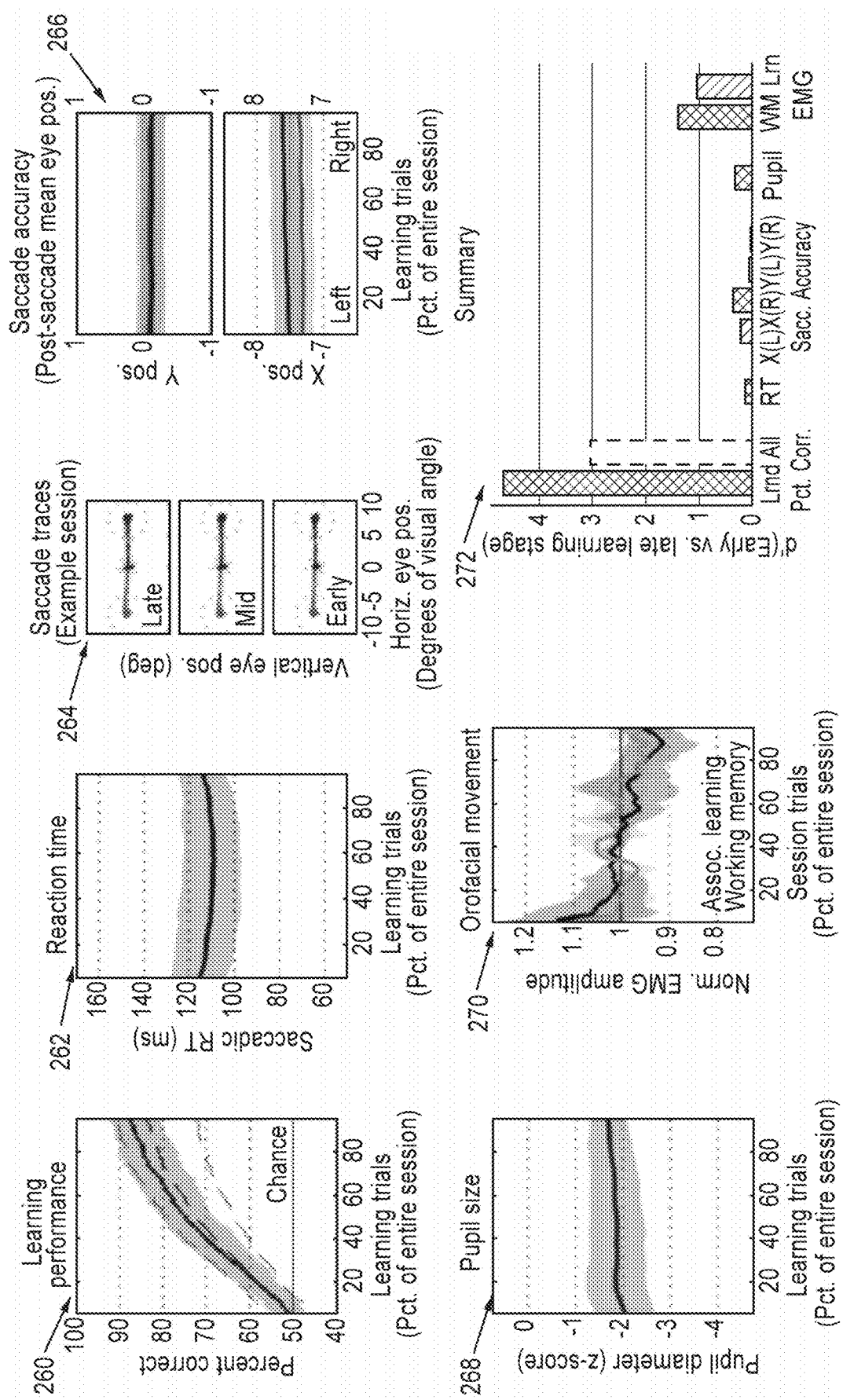
FIG. 2D is a series of plots illustrating primate learning performance and different behavioral metrics in accordance with some embodiments.

Behavioral measures of motor function, motivation, and arousal do not change appreciably with associative learning in accordance with some embodiments. FIG. 2D illustrates different behavioral metrics calculated in identical sliding trial windows (width, step=10%, 0.5% of each total session length) and plotted in a similar relative scale (about 10× average SD across trial windows). Panel 260 is a plot representing the across-session (all sessions meeting learning criteria; n=61) mean±SD of logit-transformed percent of correct trials, plotted as a function of the percentile of each session's trials. This is the same data plotted in FIG. 2C, but with learning curves pooled (averaged) across all four associations in each session, to match the number of observations for other data in this figure. Performance robustly increases across trials ($p<10^{-4}$; permutation test on means of early vs. late learning stage). This difference is not due to restricting analysis to sessions with successful learning, as it remains significant when all sessions (n=87) are included ($p<10^{-4}$; dashed curves). Panel 262 is a plot representing the across-session (n=61) mean±SD of log-transformed reaction times to response targets. This metric—which reflects both motor preparatory and motivational factors—does not change with learning (p=0.49).

Panel 264 includes saccade traces from a typical session. Eye position was plotted for −130 ms to 130 ms relative to saccade onset to left and right targets, for each trial in the early, middle, and late learning stages. Dashed circles indicate extent of fixation and saccade windows. Panel 266 is a plot of the across-session (n=61) mean±SD of vertical (top) and horizontal (bottom) saccade endpoint locations (mean position 30 ms to 130 ms after saccade onset, when the eyes were typically stable on the target). This motor-execution-related metric also does not reliably change with learning (all p>0.05 for two axes×two target locations).

Panel 268 is a plot of across-session (n=61) mean±SD of pupil diameter during delay period (100 ms to 850 ms after start of delay), when pupil size is least influenced by external factors. Within each session, pupil size is expressed as a z-score relative to the fixation period mean and SD. This metric—which has been strongly linked to global arousal—does not significantly change with learning (p=0.07).

Panel 270 is a plot of across-session mean±SD of lip EMG during outcome feedback period (100 ms to 1350 ms after outcome feedback), normalized by its mean value for each session. EMG was measured from dorsal lip muscles (orbicularis oris) as a proxy for reward-related orofacial movements. Since the original animals used for all other reported results were no longer available for these post hoc experiments, EMG was measured from two animals performing a working memory-guided saccade task (4 sessions) or a visuomotor associative learning task (6 sessions). Standard surface EMG methods were used (monopolar recording from 6 mm AgCl disc electrodes; filtered 10-250 Hz; full-wave rectified). This metric also shows little change with learning for either the working memory (p=0.1) or learning (p=0.43) tasks.

Panel 272 summarizes the behavioral results. To compare behavioral changes across all reported metrics, relatively independent of the number of observations, a d' statistic was calculated between the early and late learning stages (|mean$_{early}$−mean$_{late}$|/SD$_{pooled}$). These results reiterate that across-trial changes in motor behavior, motivation, and arousal are relatively minor compared with learning-related changes in performance.

For analyses of spiking activity, spike times were converted into smoothed rate (spike density) functions via convolution with a Hann window, as shown in Equation (2):

$$y(t) = \begin{cases} 0.5(1 + \cos(\pi t/\alpha)) & \text{if } -\alpha \leq t \leq \alpha \\ 0 & \text{otherwise} \end{cases} \quad (2)$$

where width parameter α=175 ms (nearly identical to a Gaussian function of 70 ms SD, but with a finite spread equal to ±α). For summary analyses, spike rates were instead calculated within time epochs designed to capture either primarily transient (100 ms to 500 ms after retrieval cue or outcome feedback onset) or sustained (600 ms to 1350 ms) neural responses during the delay or inter-trial interval periods.

To ensure the results were not affected, any slow fluctuations in spike rate unrelated to task factors were removed before further analysis. Slow trends were estimated at each time point/epoch by convolving the spike rate across trials with a Gaussian broad enough to blur out rate differences related to individual conditions (SD=32 trials=8 repetitions of all associations). This estimate was subtracted from the individual-trial spike density functions before further analysis. Results were similar, but with weaker signal-to-noise, without this detrending.

To measure the strength of spike rate signals reflecting each task factor of interest (i.e., cue and associate object identities, trial outcome), the percent of explained variance (PEV) in the smoothed rate functions by the task factor was calculated at each time point. For analysis of trial outcome, this was calculated via a 1-way ANOVA (2 levels: correct, incorrect). For cue and associate identity, a nested 2-way ANOVA was used in order to measure the effect of a nesting factor while partialling out the effect of a nested factor. To examine PEV across learning, these analyses were performed independently within sliding trial windows (for cue/associate identity, window width and step=10% and 2.5% of total number of session trials; for trial outcome, both=33%, due to necessity of trial-balancing). Because the traditional formulation of the PEV statistic $PEV_{\eta 2}=SS_{Groups}/SS_{Total}$ is biased toward positive values, the bias-corrected formulation was used instead, as shown in Equation (3):

$$PEV_\omega^2 = \frac{SS_{Groups} - df_{Groups}MS_{Error}}{SS_{Total} + MS_{Error}} \quad (3)$$

where $SS_{Groups}$ and $SS_{Total}$ are the between-groups (task conditions) and total sums of squares, $df_{Groups}$ is the groups' degrees of freedom, and $MS_{Error}$ is the mean squared error. This resulted in an unbiased metric, with an expected value of zero when there is no difference between conditions. Similar results were obtained using shuffle-corrected Shannon mutual information or area-under-ROC analyses.

As formulated, another unwanted signal might still contribute to associate-object PEV. Since it is computed as a contrast between pairs of cue-object conditions, some portion of associate PEV might be due to selective activation of a neuron by random combinations of cue objects. If so, activation to combinations of cues not paired with same associate would be just as likely as to cues paired with same associate. To control for this possibility, associate-object PEV was recalculated using all mispaired cue-associate nesting relationships, and the average of these was subtracted from the PEV calculated from the actual, proper condition grouping. The resulting corrected statistic is plotted in FIG. 3A in accordance with some embodiments. Simulations showed this statistic to have an expected value greater than zero for neurons active for a specific associate object, but less than or equal to zero for neurons activated by one or more cues not paired with the same associate.

To measure population neural bias toward representing one condition over another (i.e., correct more than incorrect outcomes or vice versa), a signed version of the PEV was calculated, where the PEV at each time point is multiplied by the sign of the difference in rate between the two conditions of interest, as shown in Equation (4):

$$PEV_{signed}(t)=PEV(t)*sign(rate_{cond1}(t)-rate_{cond2}(t)) \quad (4)$$

This metric has an expected value of zero if the two conditions are represented equally across the neural population. Finally, for display purposes only, spike selectivity plots were smoothed with a 2D Gaussian with SDs [5% of session length, 50 ms] and interpolated to a finer sampling grid.

Figure 3A:
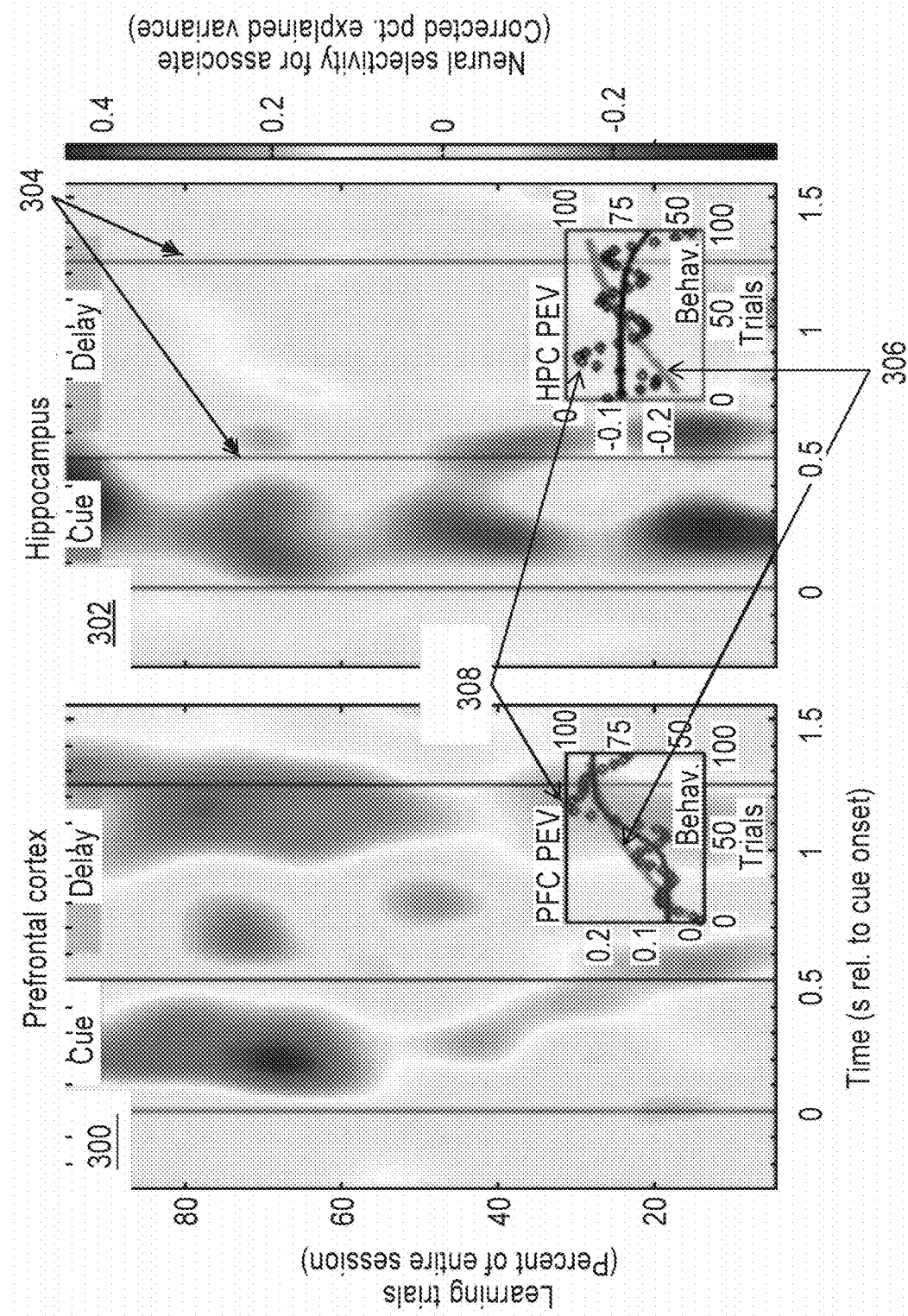
FIG. 3A is a series of plots illustrating the mean percent of variance explained by learned associate objects in PFC and HPC spiking activity, respectively, across time after cue onset and learning trials in accordance with some embodiments.

With learning, PFC neurons increasingly showed activity after the cue that anticipated its paired associate, with an across-trial progression similar to improvement in performance (Spearman's ρ=0.59 with cue-epoch spike rate, p=0.04, permutation test). FIG. 3A is a plot of the mean percent of variance explained (PEV) by learned associate objects in PFC 300 (n=319 neurons) and HPC 302 (n=199) spiking activity, plotted across time after cue onset (x-axis) and learning trials (y-axis). Bias correction results in negative values for some trials/time points in which values are less than expected based on selectivity for random combinations of cue objects. The gray bars 304 indicate analytical epochs focusing on cue and delay periods. The insets show behavioral learning curves 306 and neural "learning curves" 308—mean cue-epoch PEV across trials. Only the PFC shows learning of associates in parallel with behavior.

Figure 3B:
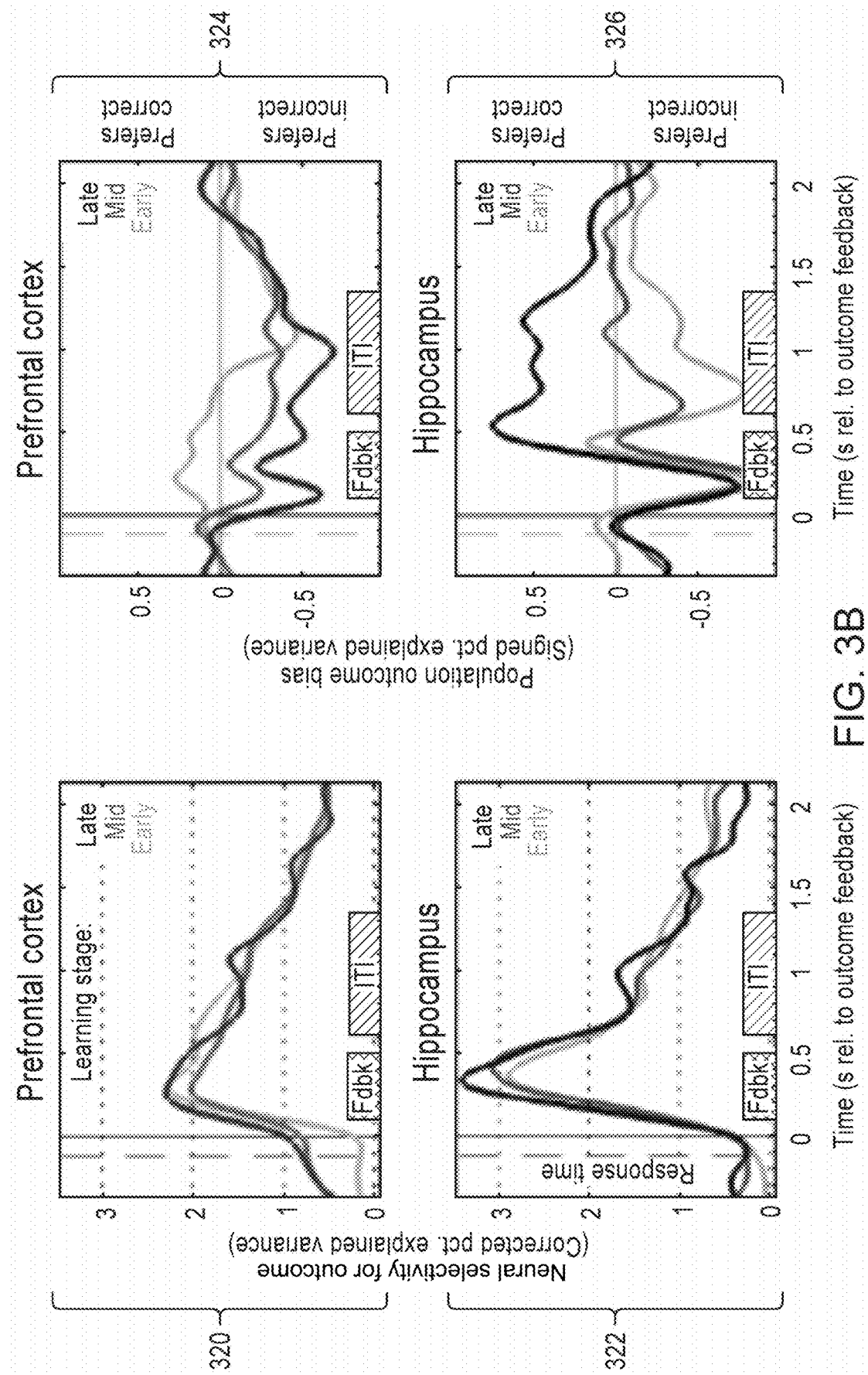
FIG. 3B is a series of plots illustrating the mean percent of variance and mean bias in PFC neurons and HPC neurons, respectively, based on trial outcomes across time after outcome feedback for early, middle, and late learning stages in accordance with some embodiments.

Hippocampal neurons reflect trial outcome in accordance with some embodiments. FIG. 3B includes plots of the mean percent of variance in PFC neurons 320 and HPC neurons 322 explained by trial outcome (correct vs. incorrect), plotted across time after outcome feedback (reward vs. no-reward) for early, middle, and late learning stages (first, middle, and last thirds of session trials; light-to-dark). The gray bars indicate analytical epochs focusing on transient responses to outcome feedback and sustained activity during the inter-trial interval (ITI). Outcome is represented more strongly in HPC (p=0.049, 2-way area×learning ANOVA in outcome feedback epoch). FIG. 3B also includes plots of the mean bias (signed PEV) in PFC neurons 324 and HPC neurons 326 for correct (positive values) vs. incorrect (negative values) outcomes, as a function of time and learning stages. HPC shifts from incorrect to correct outcomes with learning (p=0.027, permutation test on early vs. late learning stages, with correct and incorrect trial numbers matched across learning). Though there is a significant area×learning stage interaction (p=0.03), PFC shows no significant change with learning (p=0.3).

Figure 4A:
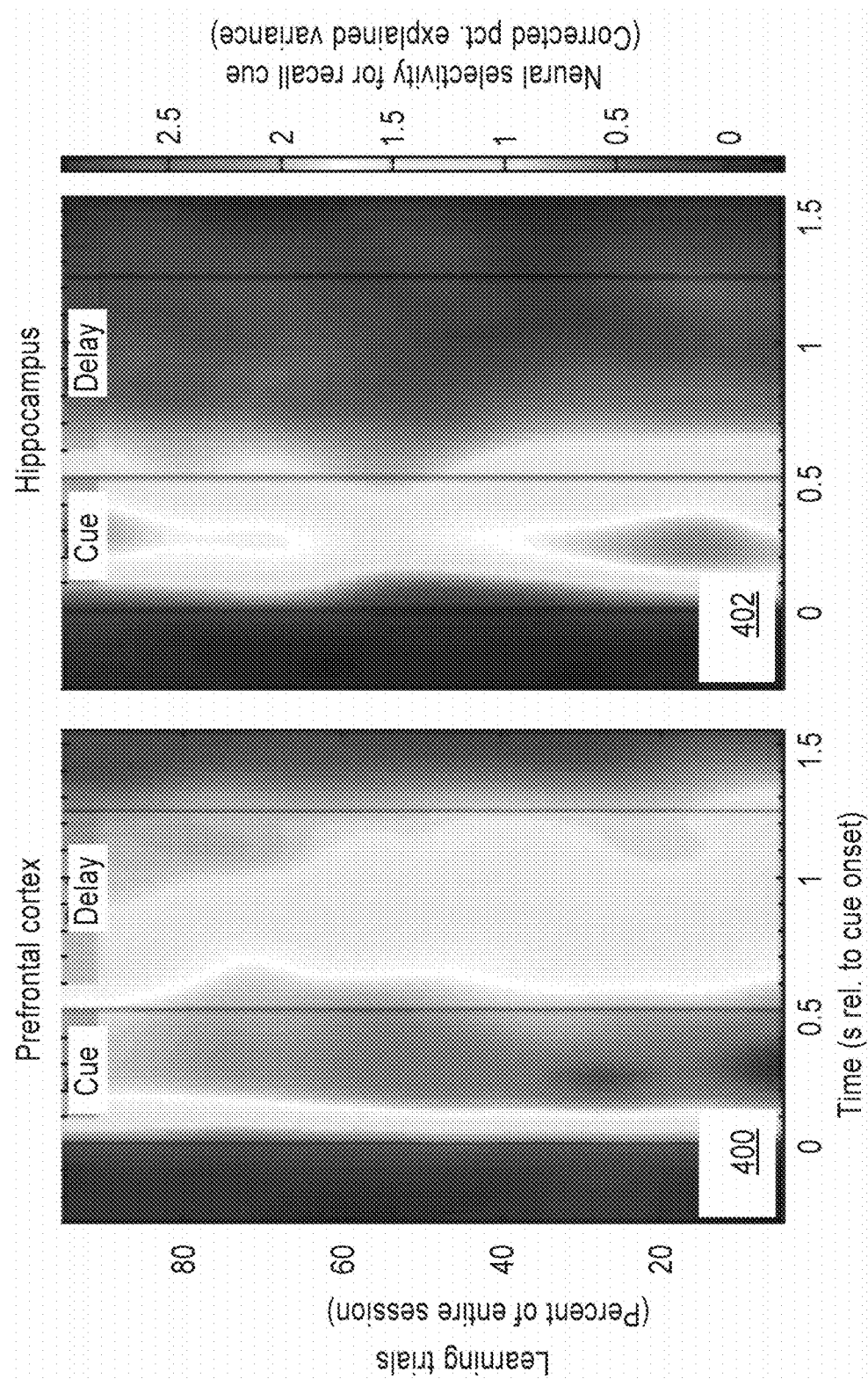
FIG. 4A is a series of plots illustrating the mean percent of variance in PFC spiking activity and HPC spiking activity, respectively, by retrieval cue across time after cue onset and learning trials in accordance with some embodiments.

Both the HPC and the PFC carry neural information about the retrieval cue in accordance with some embodiments. FIG. 4A includes plots of the mean percent of variance in PFC spiking activity 400 and HPC spiking activity 402 explained by retrieval cue, plotted across time after cue onset (x-axis) and learning trials (y-axis). Activity reflecting the cues is present in both areas, in contrast to activity reflecting the learned associates, which is only found in PFC, as shown in FIG. 3B. This indicates the lack of associate signals in HPC is not due to a lack of selective visual responses to the stimuli used.

However, while HPC neuronal activity conveyed sensory signals reflecting the cue object, it did not reflect learning of the paired associate and showed no correlation with behavior (ρ=−0.21, p=0.73). Instead, HPC reflected the trial outcome after the feedback (reward vs. no-reward) about whether the behavioral response was correct or incorrect. This effect was stronger in the HPC than in the PFC (p=0.049, ANOVA), and within the HPC, stronger in the output subregions (CA1 subiculum) than locally-projecting subregions (CA3, dentate gyrus; p<10-4). With learning, this HPC activity shifted from stronger activation after incorrect to correct outcomes (p=0.027, permutation test on early vs. late learning stages [first vs. last third of learning trials], with number of incorrect vs. correct trials matched across learning).

Figure 4B:
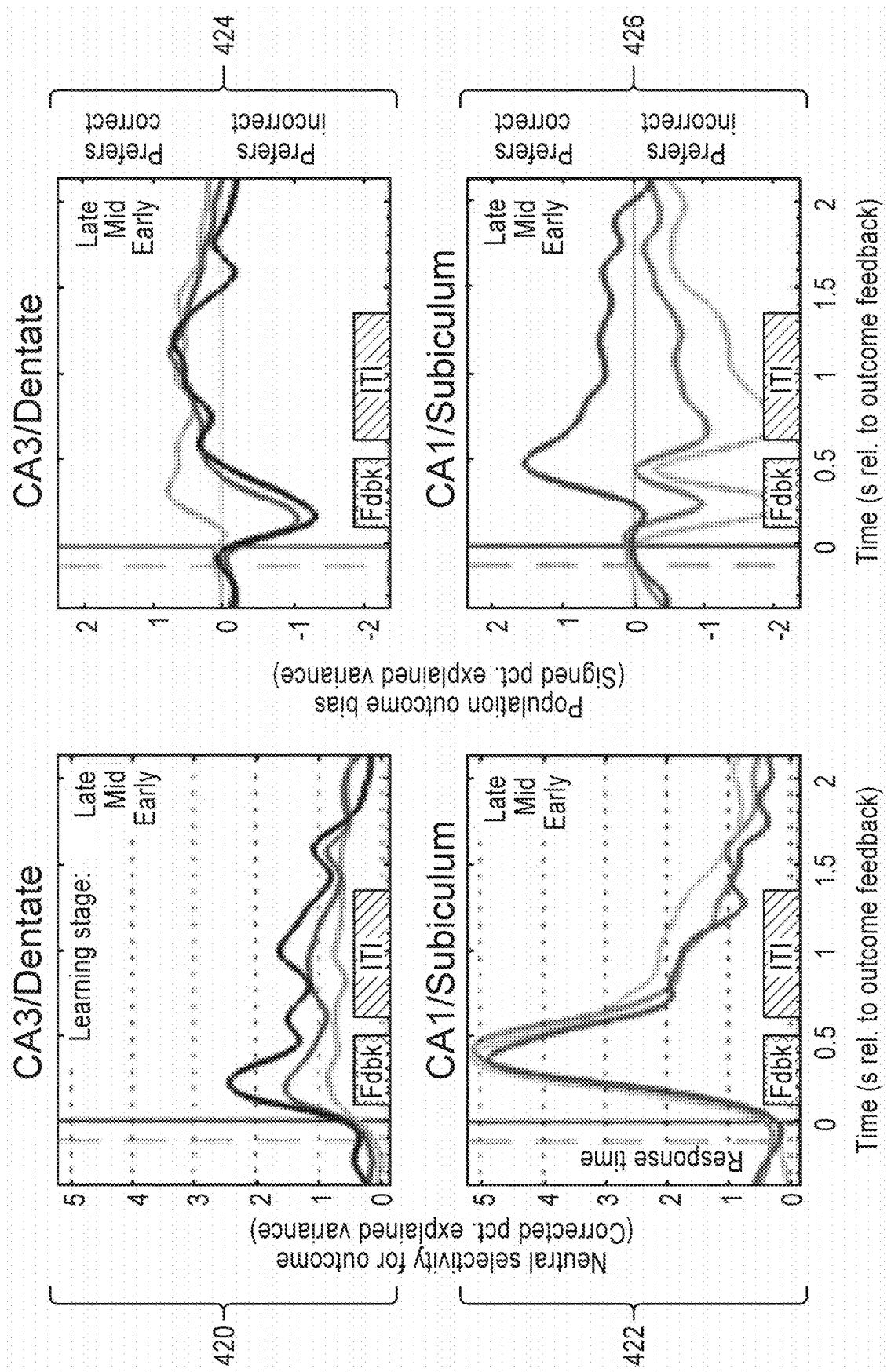
FIG. 4B is a series of plots illustrating the mean selectivity for trial outcome in HPC local-projection subregions and output subregions neurons across learning stages and the mean bias for correct versus incorrect outcomes, respectively, in accordance with some embodiments.

This change with learning was in HPC output subregions (p=0.005), but not local-projection subregions (p=0.83; subregion×learning-stage interaction: p=0.04), which may be related to a corresponding shift in communication between the HPC and PFC in accordance with some embodiments. FIG. 4B includes plots of the mean selectivity (PEV) for trial outcome in hippocampal local-projection subregions neurons 420 (Dentate gyrus/CA3; n=104 neurons) and output subregions neurons 422 (CA1/Subiculum; n=93), plotted across learning stages (light-to-dark). Outcome signals are significantly stronger overall in the HPC output subregions (p<10-4; 2-way subregion×learning-stage ANOVA in outcome feedback epoch). FIG. 4B also includes plots of the mean bias (signed PEV) in HPC local-projection neurons 424 and output subregion neurons 426 for correct (positive values) vs. incorrect (negative values) outcomes. With learning, there was a significant shift from stronger signals for incorrect to correct trials in HPC output subregions (p=0.005; permutation test on ITI epoch signals in early vs. late learning stages), but not local-projection subregions (p=0.83; interaction in 2-way subregion×learning-stage ANOVA: p=0.04).

Any power line noise, and its harmonics, was estimated by fitting sinusoids in 5 s sliding windows, and subtracted them from the raw data (i.e., using the rmlinesmovingwinc function in the Chronux toolbox, available from MedaMetrics, LLC (New York, N.Y.)). To remove the contribution of signal components phase-locked to trial events (event-related evoked potentials), these were measured as the across-trial mean of the raw LFP and subtracted off each individual trial's LFP before further analysis. This correction was performed separately for each trial window and condition, to account for any possible changes in evoked activity across these factors. For the multivariate auto-regression-based causality analysis (see below), each trial was additionally normalized by the across-trial standard deviation, and the LFP signals downsampled to 200 Hz.

For summary analyses, LFP metrics (power, synchrony, etc.) were pooled within spectrotemporal regions with time ranges based on epochs used for spike analyses, but extended by 50% to account for the longer duration LFP responses (100 ms to 700 ms and 600 ms to 1725 ms), and with frequency ranges based on the empirical results (2-6 and 9-16 Hz, respectively).

For measures of LFP-LFP synchrony, LFPs were transformed into the time-frequency domain using complex Morlet wavelets (wavenumber=6, evaluated at 0.25 octave intervals from 1-256 Hz), from which their phase was extracted. The strength of neural synchrony was quantified by the phase-locking value (PLV), the length of the across-trial vector average of cross-electrode differences in phase φ, for a given time point t and frequency f, as shown in Equation (5):

$$PLV(f, t) = \left| \frac{1}{nTrials} \sum_{tri=1}^{nTrials} \exp(i[\varphi_{tri,elec1}(f, t) - \varphi_{tri,elec2}(f, t)]) \right| \quad (5)$$

PLV measures the degree to which LFP pairs maintain the same phase relationship—independent of their absolute phases and amplitudes—across repeated trials. This analysis was performed separately for each electrode pair, trial window, and condition. To quantify the difference in synchrony between task conditions, the PLV(f,t) spectrogram for one condition was subtracted from another (e.g., correct outcome minus incorrect outcome). This was normalized to a z-score-like statistic by subtracting the mean, and dividing by the standard deviation, of the between-condition PLV difference calculated across 50 random permutations of the condition labels across trials. Similar results were obtained using classical coherence or pairwise phase consistency instead of the PLV. For display purposes only, LFP synchrony plots were smoothed with a 2D Gaussian with SDs [0.15 octaves, 100 ms] and interpolated to a finer sampling grid.

Figure 5A:
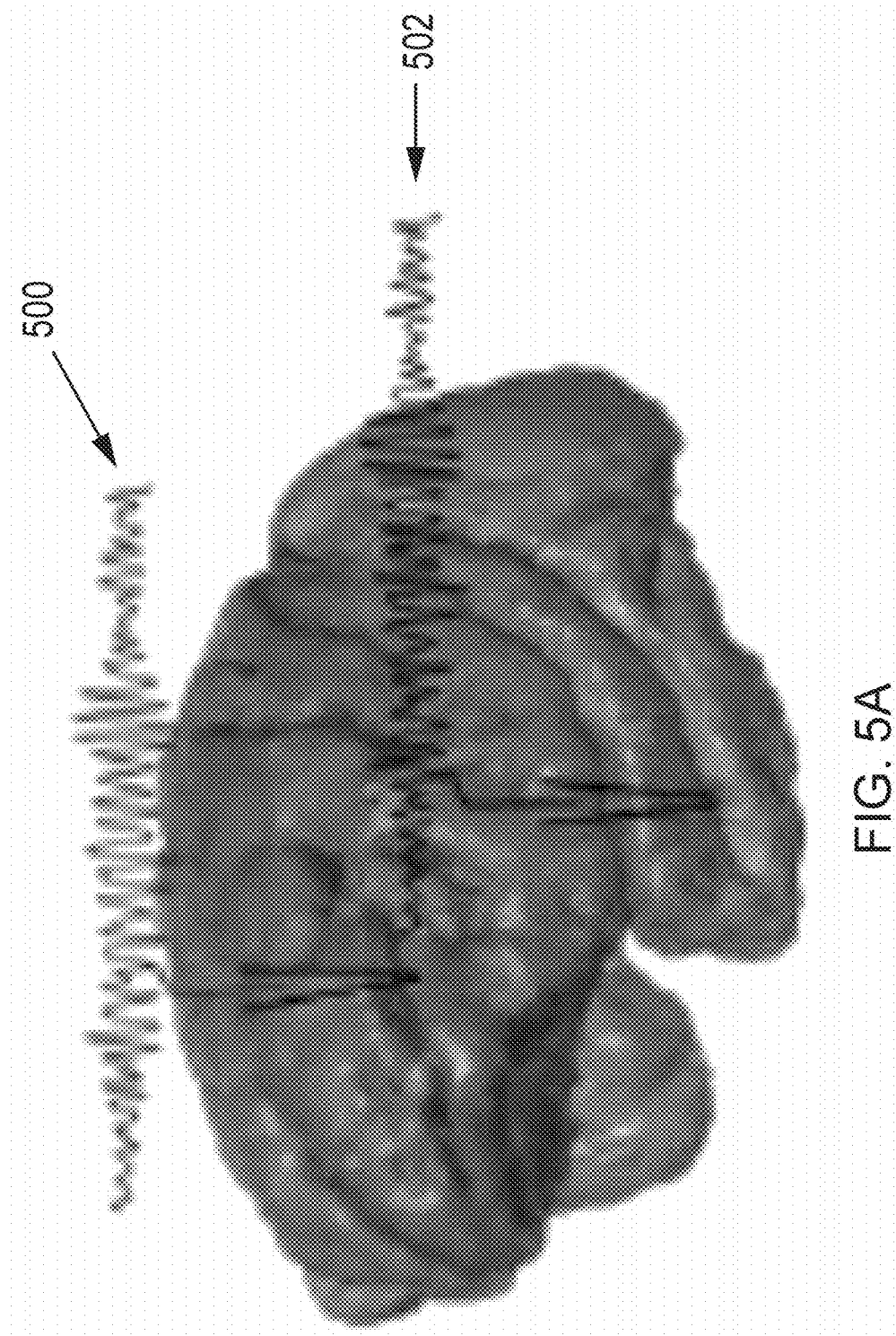
FIG. 5A is a diagram illustrating parallel recording of local field potentials from PFC and HPC in accordance with some embodiments.

Hippocampal-prefrontal oscillatory synchrony carries learning-related information about trial outcome in accordance with some embodiments. Outcome-related neural communication was examined using synchrony (phase-locking) between LFPs recorded after the behavioral response and feedback. FIG. 5A illustrates parallel recording of LFPs from PFC 500 and HPC 502. This revealed PFC-HPC synchrony in two frequency bands: a shorter latency theta-band (about 2-6 Hz) synchrony and longer latency alpha/low-beta band (about 9-16 Hz) synchrony. Alpha/beta synchrony was stronger after correct trials; theta synchrony was stronger after incorrect trials.

Figure 5B:
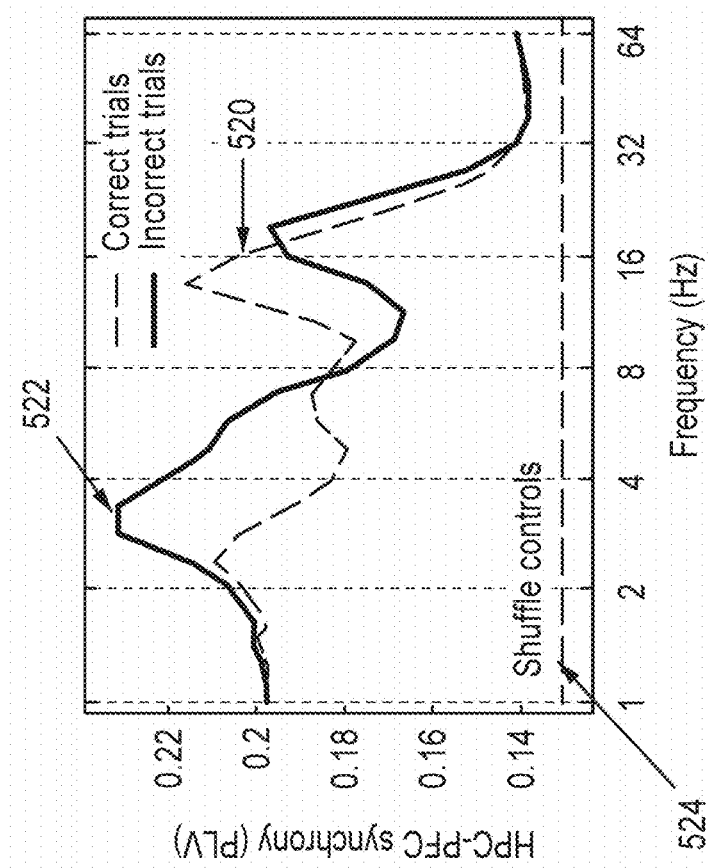
FIG. 5B is a plot of mean synchrony between HPC and PFC local field potentials as a function of frequency, following correct and incorrect outcomes in accordance with some embodiments.

FIG. 5B is a plot of mean synchrony (±SEM) between HPC and PFC LFPs, plotted as a function of frequency, following correct 520 and incorrect 522 outcomes in accordance with some embodiments. Synchrony is computed as the across-trial phase-locking value (PLV), calculated within the feedback and ITI epochs (100 ms to 1725 ms after outcome feedback), and is averaged across all 970 electrode pairs and sessions. Dashed line 524 represents mean synchrony (±SEM) expected by chance (based on shuffling HPC and PFC signals across trials), which is nearly identical across trial outcome and frequency.

Figure 5C:
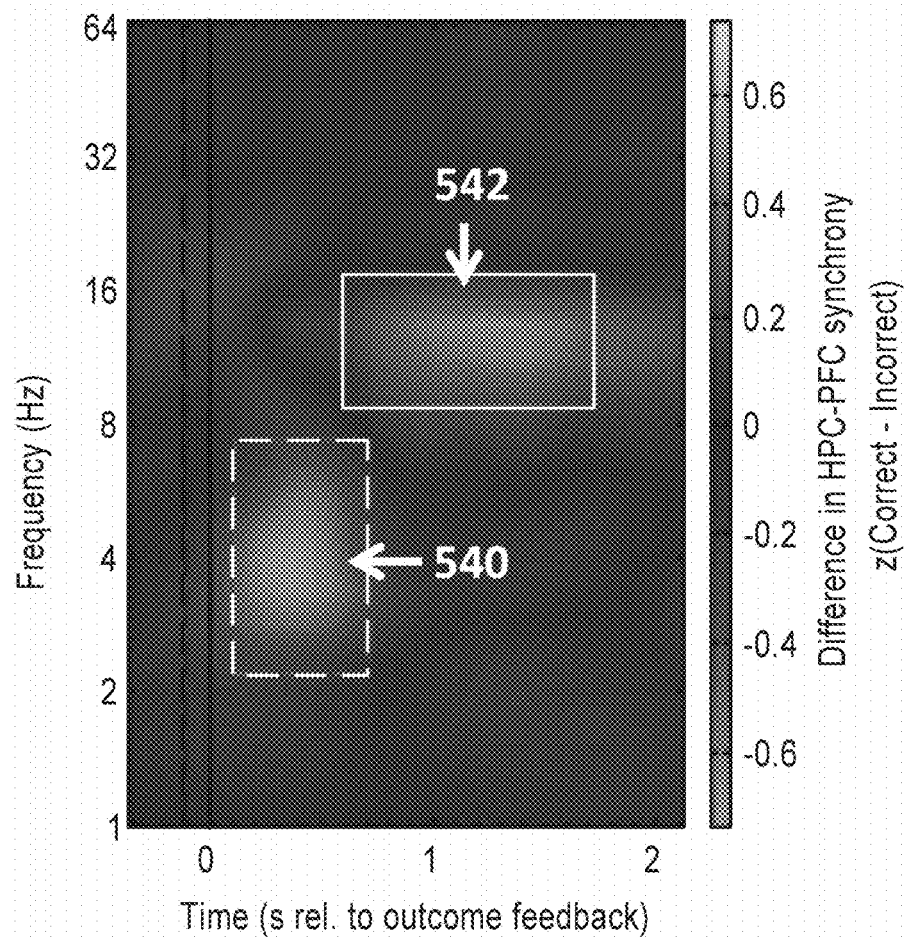
FIG. 5C is a spectrogram illustrating the mean difference in HPC-PFC synchrony between correct and incorrect trials across time and frequency in accordance with some embodiments.

FIG. 5C is a plot of the mean difference in HPC-PFC synchrony (PLV) between correct and incorrect trials, plotted as spectrograms across time (x-axis) and frequency (y-axis) in accordance with some embodiments. Correct and incorrect trials were balanced, and the PLV-difference was z-scored based on the null distribution obtained by shuffling trial outcome labels. Theta-band synchrony 540 and alpha/beta-band synchrony 542 were stronger for incorrect and correct outcomes, respectively.

Figure 5D:
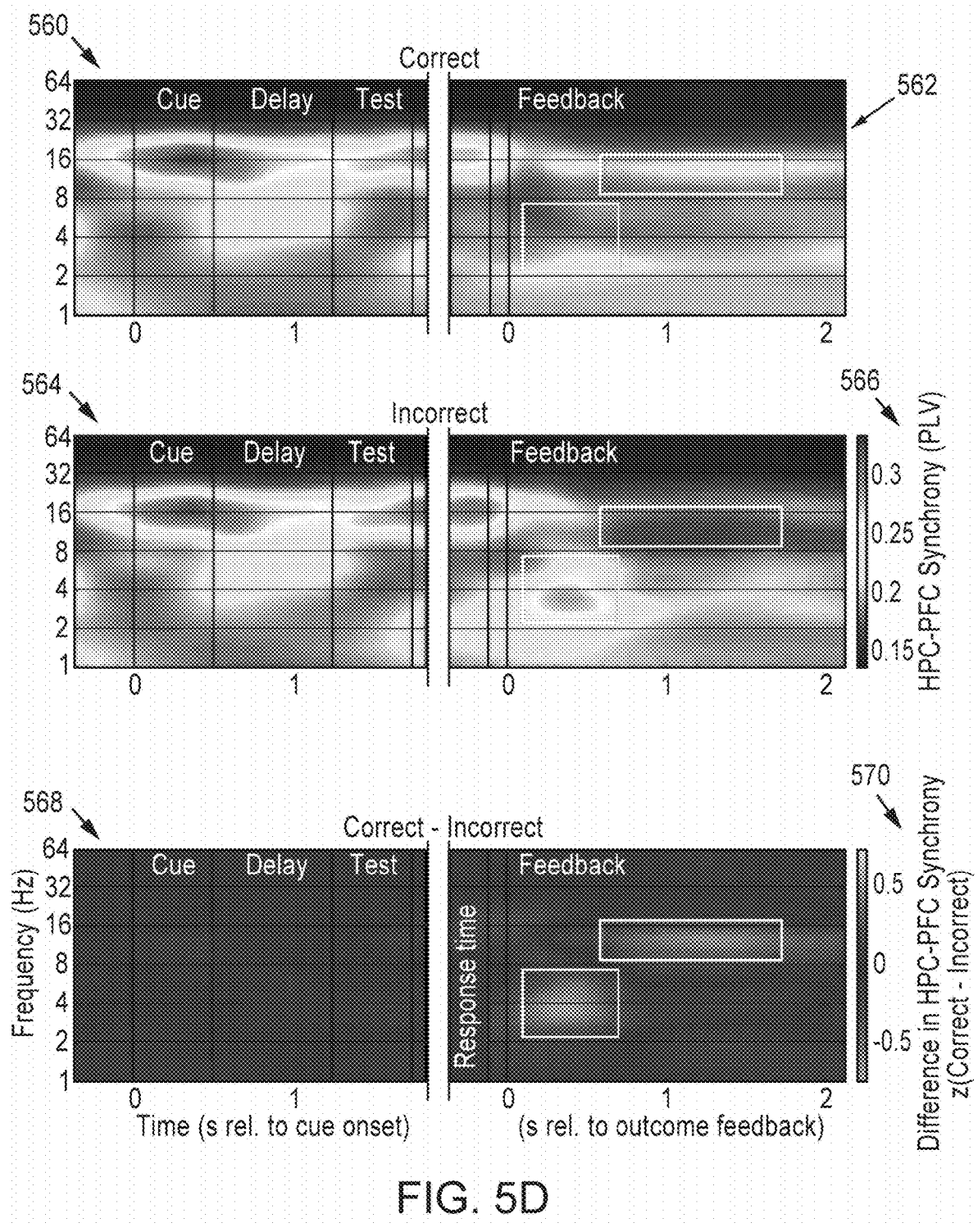
FIG. 5D is a series of plots and spectrograms illustrating HPC-PFC synchrony across all trial periods in accordance with some embodiments.

Though PFC-HPC synchrony was present before the behavioral response, it did not robustly reflect trial outcome. FIG. 5D includes plots showing HPC-PFC synchrony across all trial periods in accordance with some embodiments. First, mean synchrony (PLV) between HPC and PFC LFPs on correct trials is plotted as a spectrogram across frequency (y-axis) and time (x-axis) for time periods during the trial 560, and after outcome feedback is given 562. Mean HPC-PFC synchrony on incorrect trials is plotted as a spectrogram across frequency (y-axis) and time (x-axis) for time periods during the trial 564, and after outcome feedback is given 566. Mean z-scored difference in HPC-PFC synchrony between correct and incorrect trials for time periods during the trial 568, and after outcome feedback is given 570. Though there are clear periods of band-specific synchrony during trial performance, they are nearly identical for correct and incorrect trials, and thus convey little information about trial outcome.

Figure 5E:
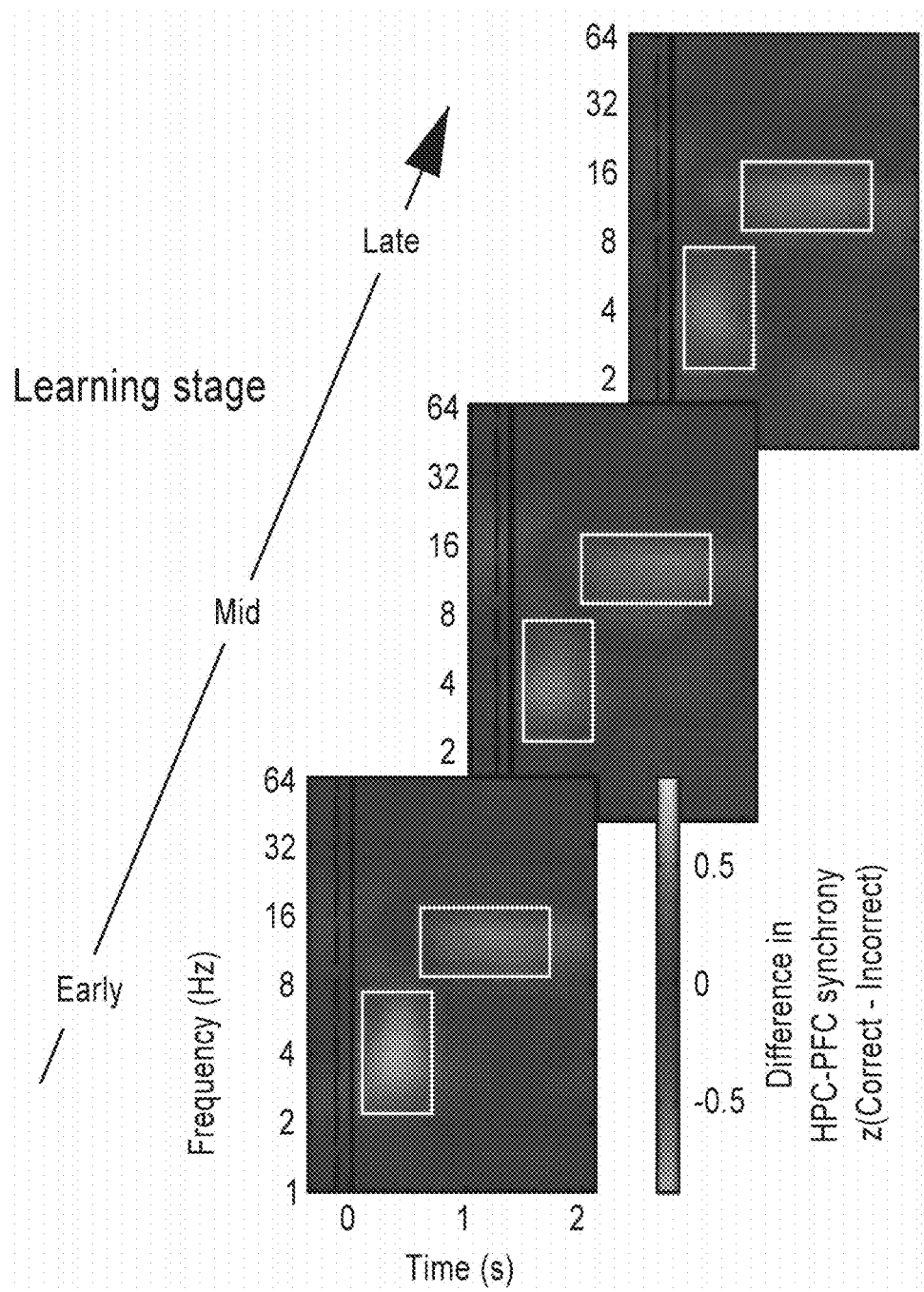
FIG. 5E is a diagram illustrating mean HPC-PFC phase-locking value difference as a function of learning, including a series of spectrograms, in accordance with some embodiments.
Figure 5F:
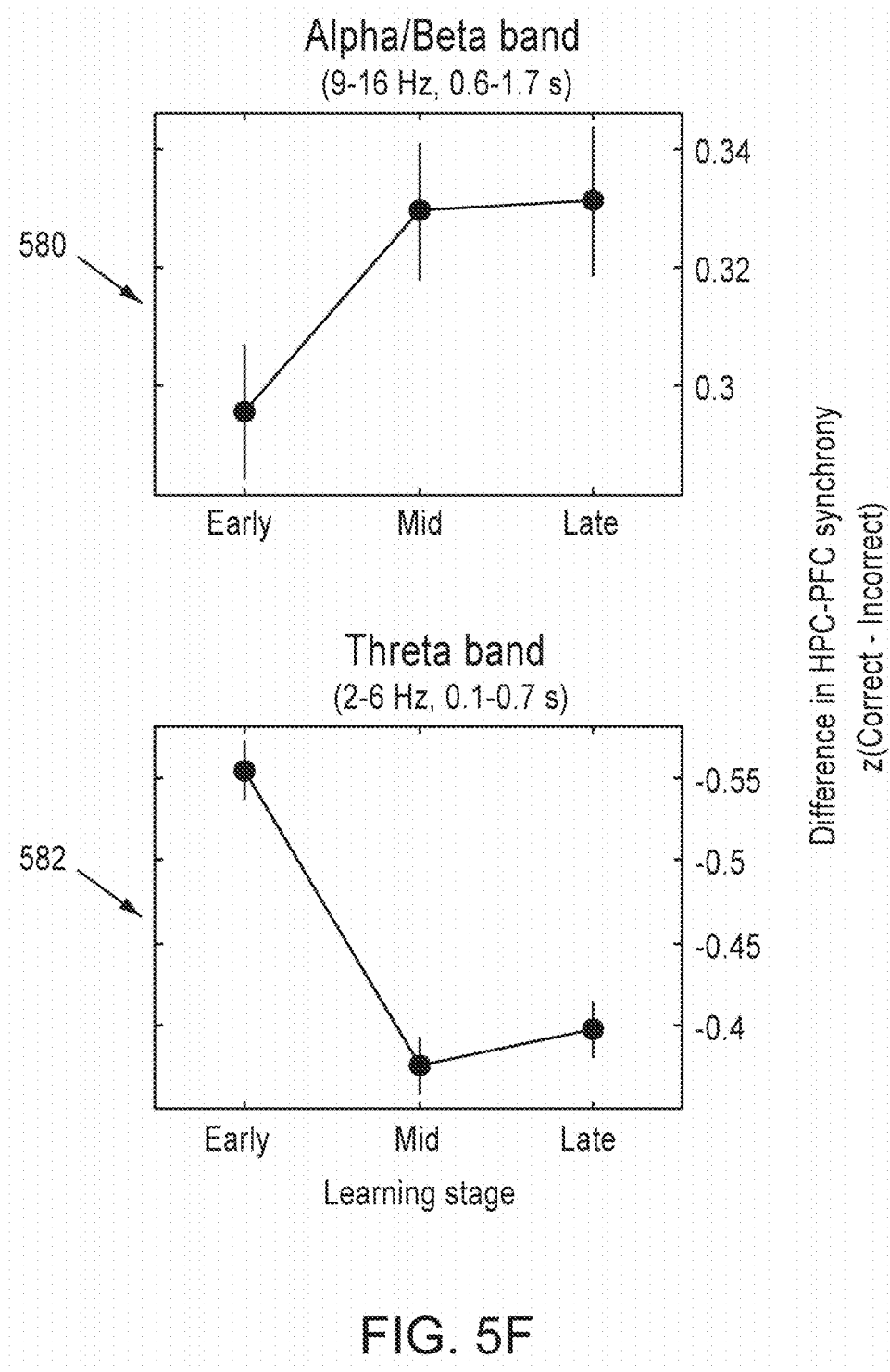
FIG. 5F is a series of plots illustrating observed synchrony learning effects for HPC-PFC as a function of learning stage in accordance with some embodiments.

FIG. 5E illustrates mean HPC-PFC PLV difference as a function of learning (bottom to top: early, middle, and late learning stages) in accordance with some embodiments. FIG. 5F summarizes observed synchrony learning effects, including the mean PLV difference (±SEM) pooled within the alpha/beta-band 580 and theta-band 582 (note that higher values in this plot reflect stronger negative PLV differences) regions of interest, as a function of learning stage in accordance with some embodiments. Theta (incorrect) synchrony decreases with learning, while alpha/beta (correct) increases. Theta synchrony following incorrect outcomes decreased with learning ($p<10$-4), while alpha/beta synchrony following correct outcomes increased with learning ($p=5\times10$-4, permutation test on early vs. late learning).

Figure 6A:
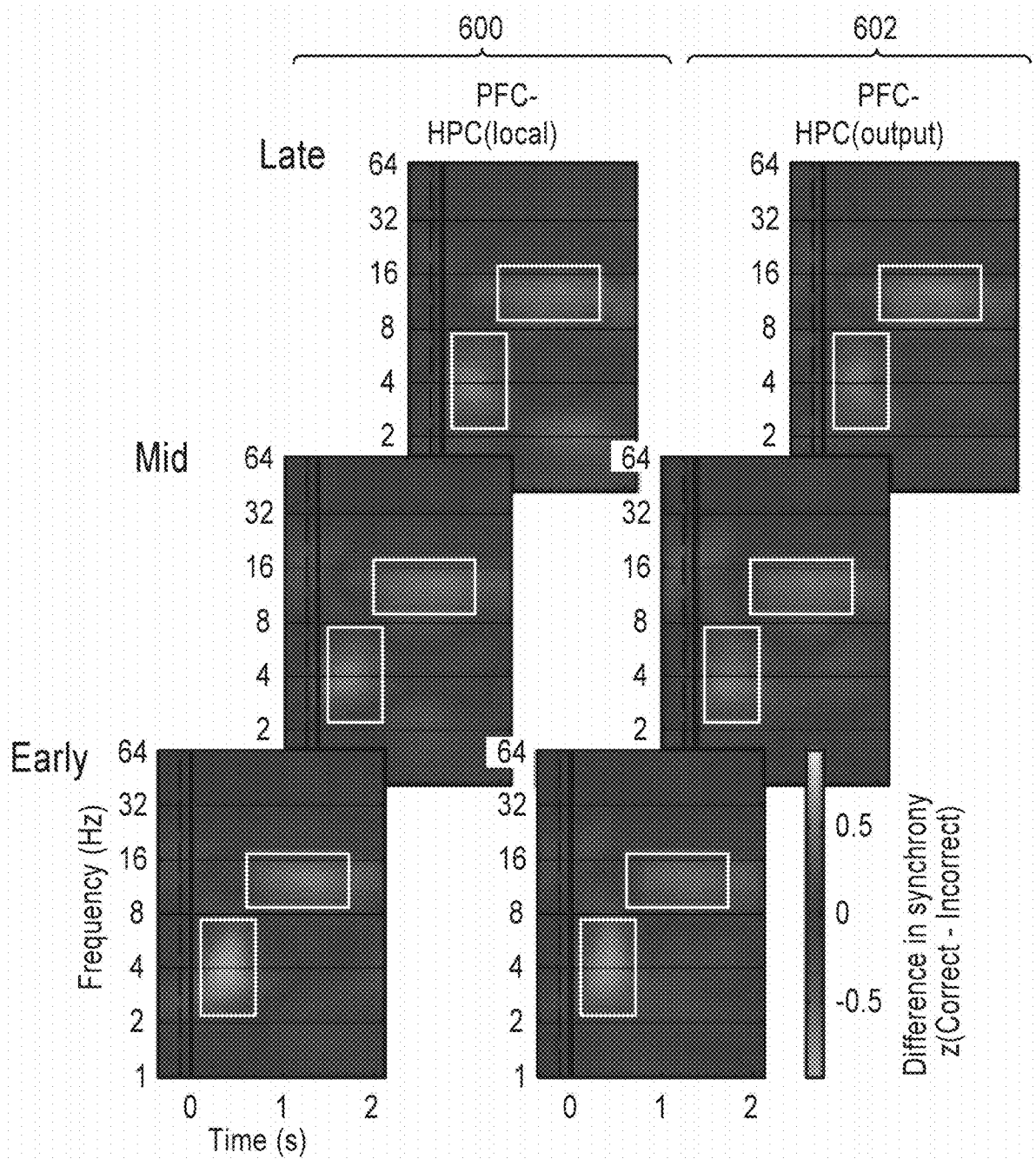
FIG. 6A is a diagram illustrating the mean z-scored difference in cross-electrode synchrony between correct and incorrect trials across learning stages for all HPC subregions, including two series of spectrograms, in accordance with some embodiments.
Figure 6B:
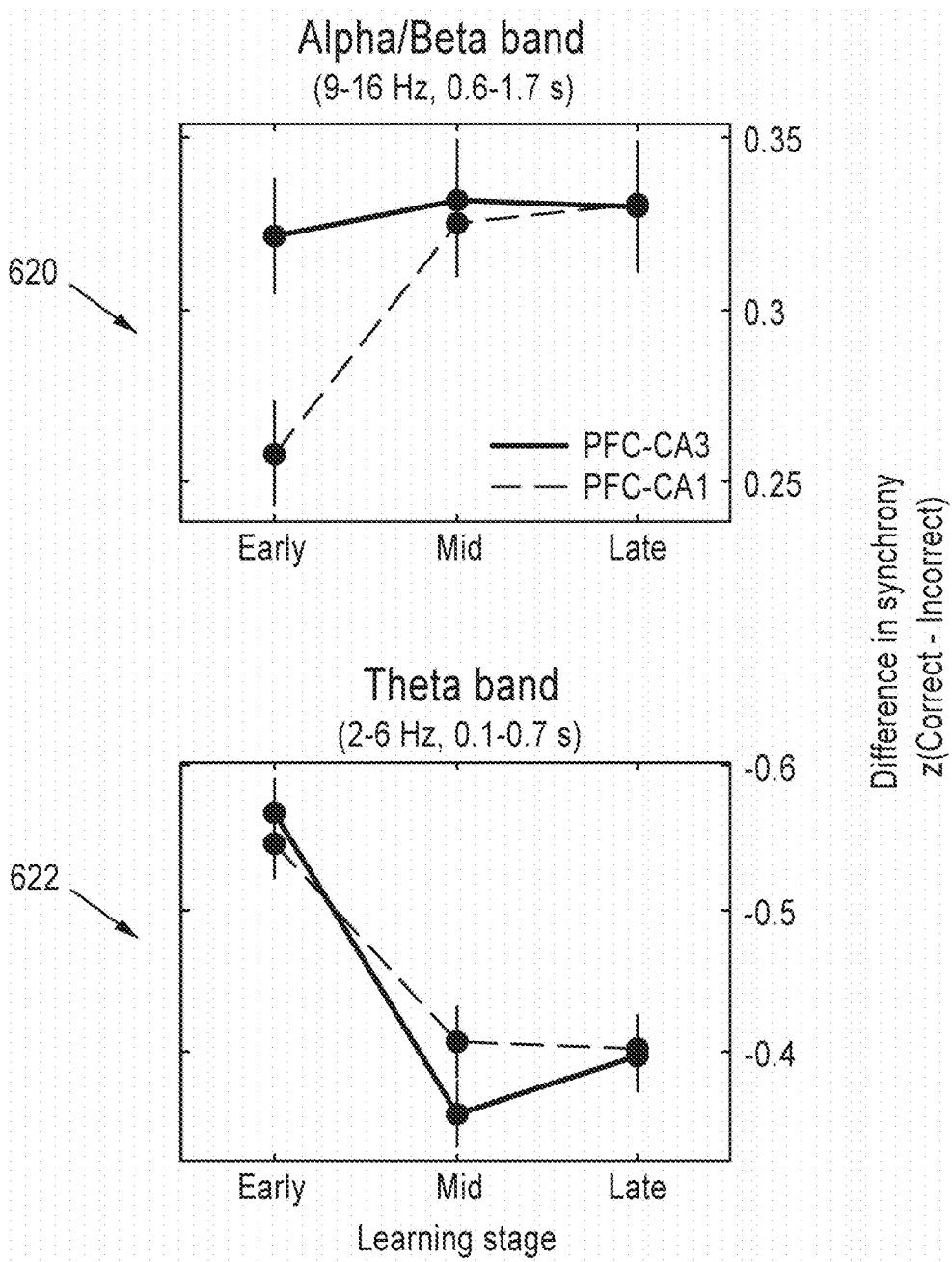
FIG. 6B is a series of plots illustrating observed synchrony learning effects for all HPC subregions as a function of learning stage in accordance with some embodiments.

While the theta effect was similar across HPC subregions, the alpha/beta increase with learning only occurred for synchrony between PFC and HPC output subregions in accordance with some embodiments. FIG. 6A illustrates the mean z-scored difference in cross-electrode synchrony between correct and incorrect trials across learning stages, for all HPC subregions, including between the PFC and the HPC local-projection subregions (i.e., the dentate gyrus and CA3: n=558 electrode pairs) 600 and between the PFC and the HPC output subregions (i.e., the CA1 and subiculum: n=407) 602. FIG. 6B summarizes synchrony learning effects, including the mean (±SEM) synchrony difference pooled within the alpha/beta-band 620 and theta-band 622 regions of interest, as a function of learning stage. While the theta-band decrease with learning is similar for synchrony between PFC and all HPC subregions ($p<10$-4 for both), the alpha/beta-band increase with learning is only present for synchrony between PFC and HPC output subregions (CA1/Sub.; $p<10$-4), but not for synchrony between PFC and HPC local-projection subregions (dentate/CA3; $p=0.52$) despite their greater numbers of observations. Synchrony between hippocampal subregions (not shown) is nearly identical to synchrony between all pairs of hippocampal electrodes; small numbers of observations precluded meaningful analysis of synchrony between sites within each subregion. Thus, with learning, there was a shift in PFC-HPC synchrony from theta toward higher frequencies, paralleling the shift in HPC spiking activity from incorrect to correct trials.

Figure 7A:
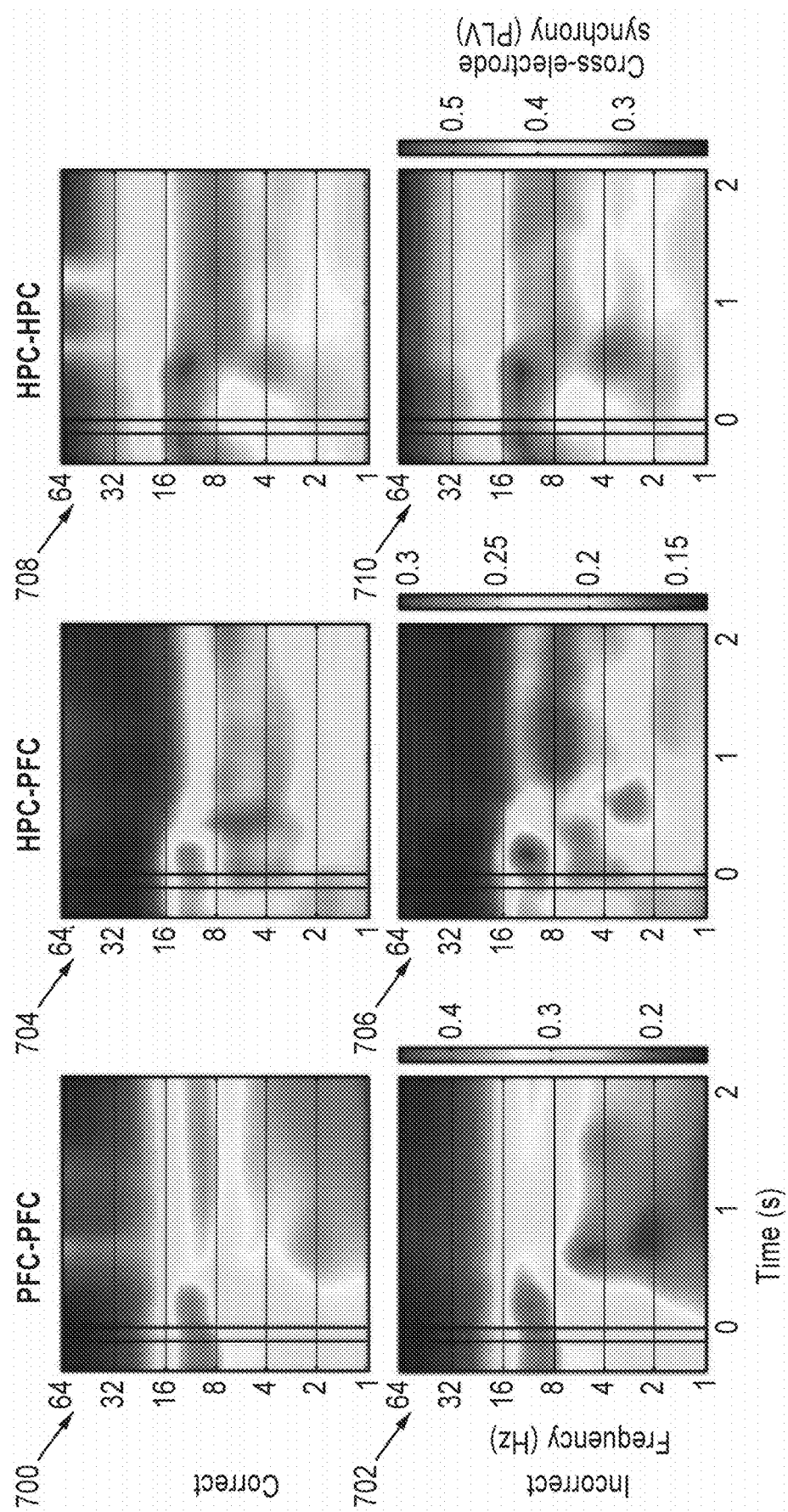
FIG. 7A is a series of spectrograms illustrating mean synchrony between pairs of electrodes in PFC, between HPC and PFC, and in HPC, respectively, in accordance with some embodiments.
Figure 7B:
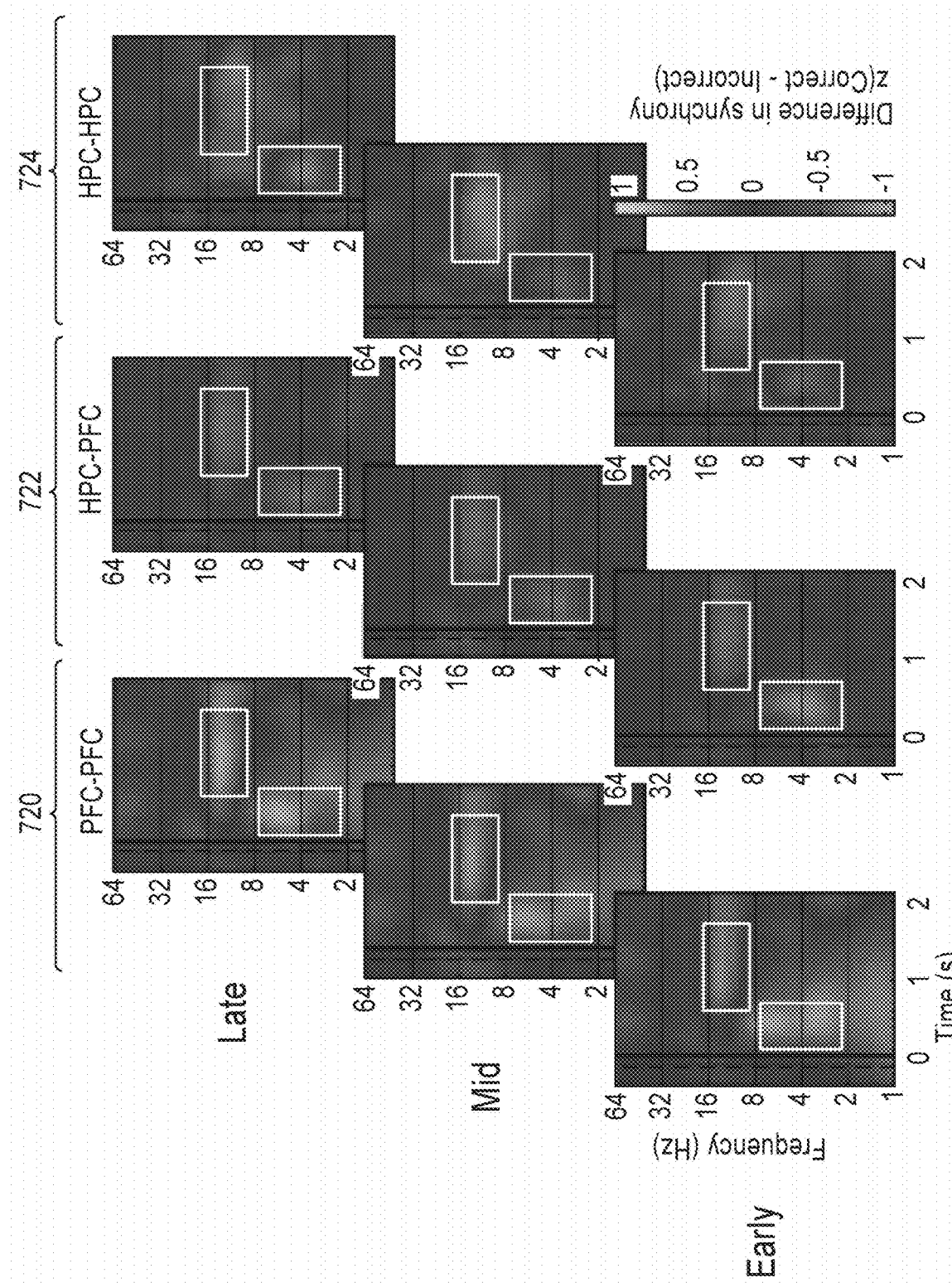
FIG. 7B is a diagram including series of spectrograms illustrating the mean z-scored difference in synchrony between correct and incorrect trials across learning stages, for all pairs of studied areas, including in PFC, between HPC and PFC, and in HPC, respectively, in accordance with some embodiments.
Figure 7C:
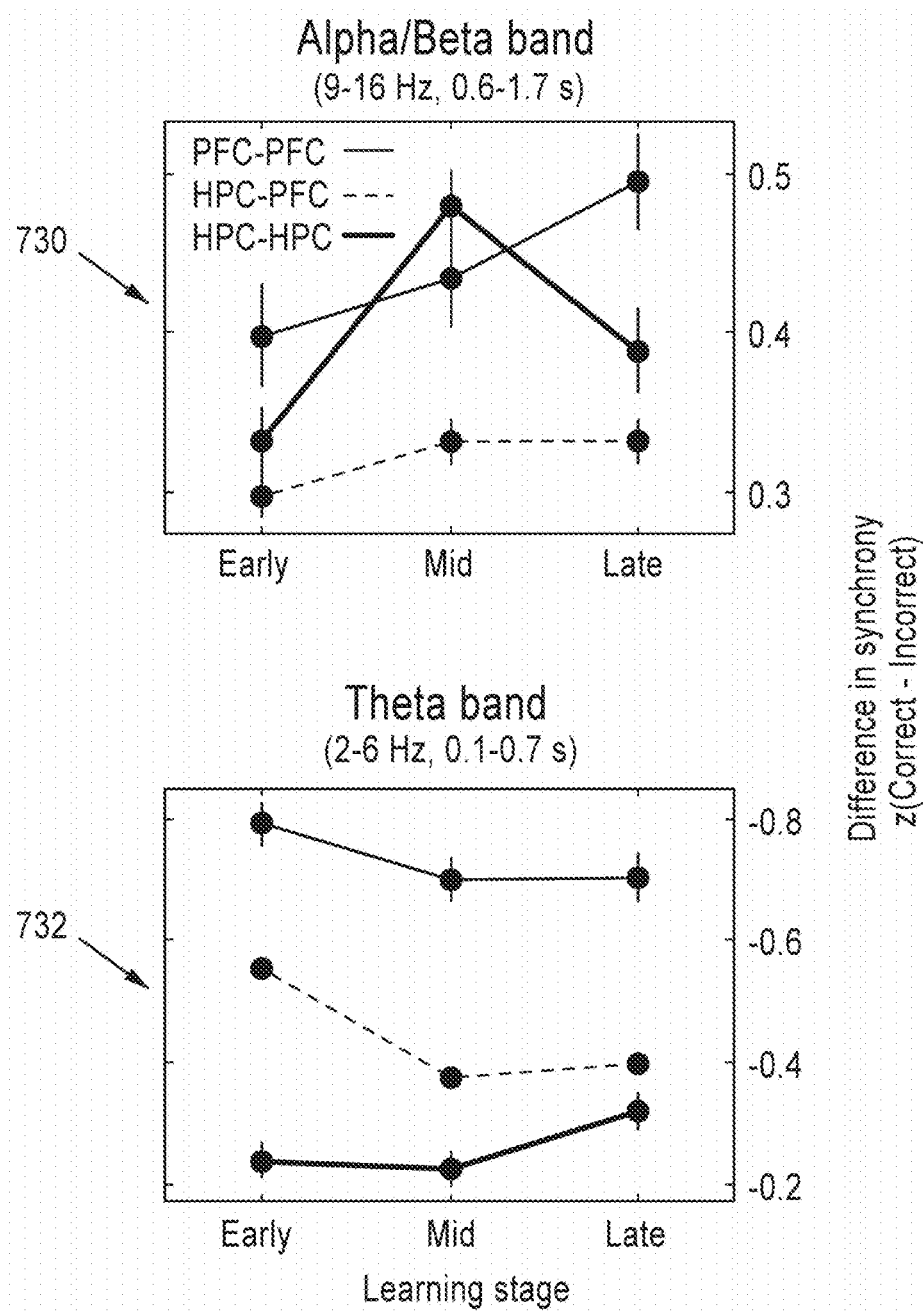
FIG. 7C is a series of plots illustrating observed synchrony learning effects between pairs of electrodes in PFC, between HPC and PFC, and in HPC, respectively, as a function of learning stage in accordance with some embodiments.

Learning-related information about trial outcome resulted in oscillatory synchrony between all area pairs in accordance with some embodiments. FIG. 7A is a series of mean synchrony (PLV) spectrograms between pairs of electrodes in PFC=648) following correct trials 700 and incorrect trials 702, between HPC and PFC (center; n=970) following correct trials 704 and incorrect trials 706, and in HPC=694) following correct trials 708 and incorrect trials 710. FIG. 7B illustrates the mean z-scored difference in synchrony between correct and incorrect trials across learning stages, for all pairs of studied areas, including in PFC 720, between HPC and PFC 722, and in HPC 724. FIG. 7C summarizes synchrony learning effects by plotting the mean (±SEM) synchrony difference pooled within the alpha/beta-band 730 and theta-band 732 regions of interest, as a function of learning stage. Synchrony between distinct sites within PFC follows a similar pattern to the cross-area synchrony—theta decreases ($p=3\times10^{-4}$), while alpha/beta increases with learning ($p<10^{-4}$, permutation test on early vs. late learning). In contrast, intra-hippocampal synchrony increases with learning for both the theta ($p=2\times10^{-4}$) and alpha/beta bands ($p<10^{-4}$), indicating the observed learning effects do not reflect global state changes that are invariant across all brain areas.

Within-area LFP phase-locking and power was also examined. While within-PFC synchrony followed a similar pattern to between-area synchrony, intra-hippocampal synchrony exhibited a distinct pattern in which theta synchrony increased—rather than decreased—with learning. This indicates the observed learning-related synchrony changes do not simply reflect state changes with global effects.

Figure 8B:
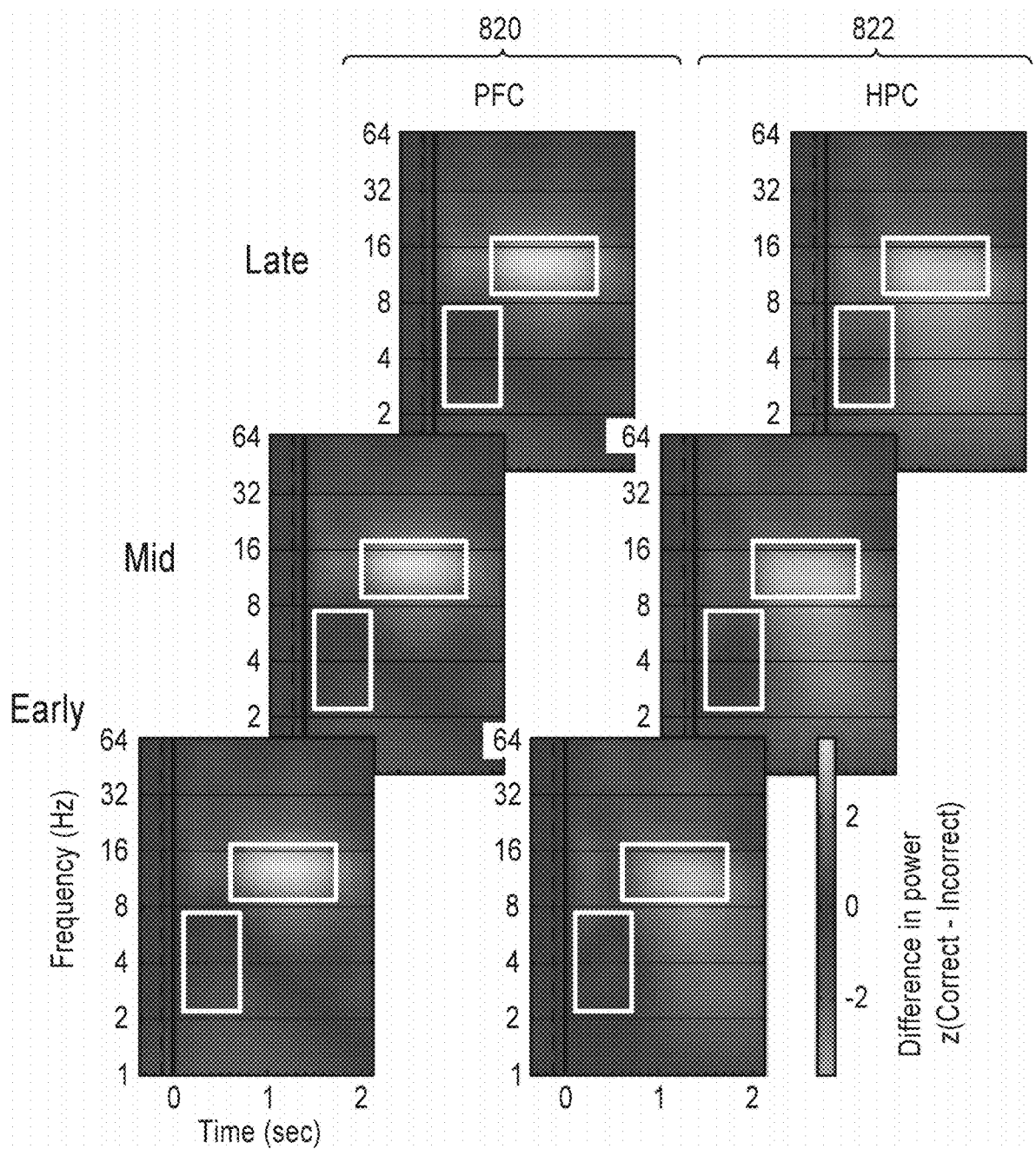
FIG. 8B is a diagram including series of spectrograms illustrating the mean z-scored difference in log-power between correct and incorrect trials across learning stages, for PFC and HPC, respectively, in accordance with some embodiments.
Figure 8C:
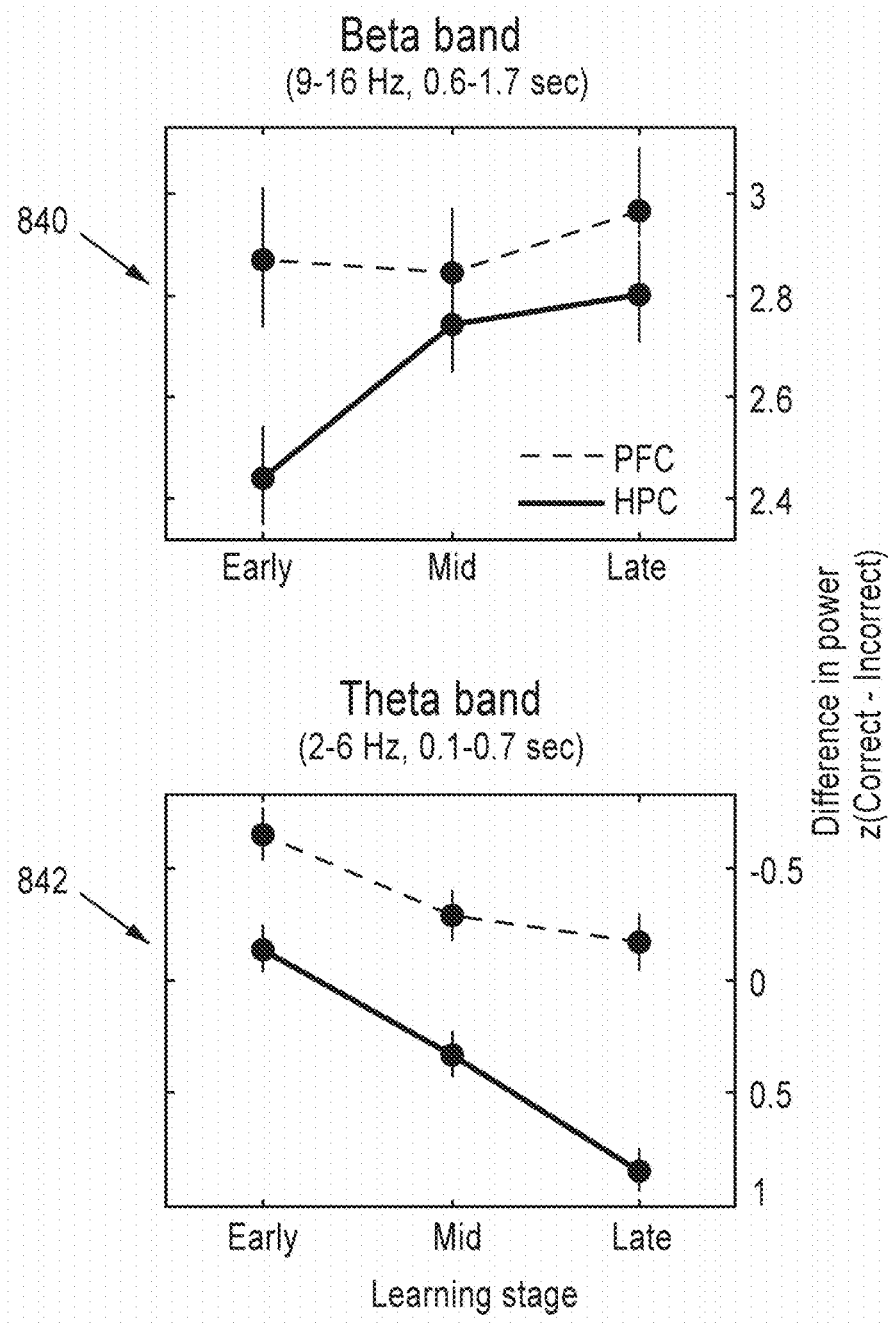
FIG. 8C is a series of plots illustrating the mean power difference pooled within the alpha/beta-band and theta-band regions of interest, respectively, as a function of learning stage in accordance with some embodiments.

LFP power, reflecting local synchrony, exhibited a pattern broadly similar to cross-area synchrony, as would be expected from an interacting system with causal links between local and long-range synchrony and in accordance with some embodiments. FIG. 8A includes mean log-transformed LFP power spectrograms in PFC (n=250 electrodes) following correct trials 800 and incorrect trials 802, and in HPC (n=166), following correct trials 804 and incorrect trials 806. FIG. 8B illustrates the mean z-scored difference in log-power between correct and incorrect trials across learning stages, for PFC 820 and HPC 822. While there is a strong alpha/beta-band signal for correct trials, the theta-band signal for incorrect trials observed in the cross-electrode synchrony results is not as robust in local power. FIG. 8C summarizes power learning effects by plotting the mean (±SEM) power difference pooled within the alpha/beta-band 840 and theta-band 842 regions of interest, as a function of learning stage. Theta power exhibits a significant positive shift (from incorrect toward correct bias) with learning ($p<10-4$ for both areas), and alpha/beta power also shows a positive trend (significant only for HPC: $p<10-4$; PFC: $p=0.06$). These results indicate a similar change with learning for both cross-area synchrony and within-area power.

Figure 9A:
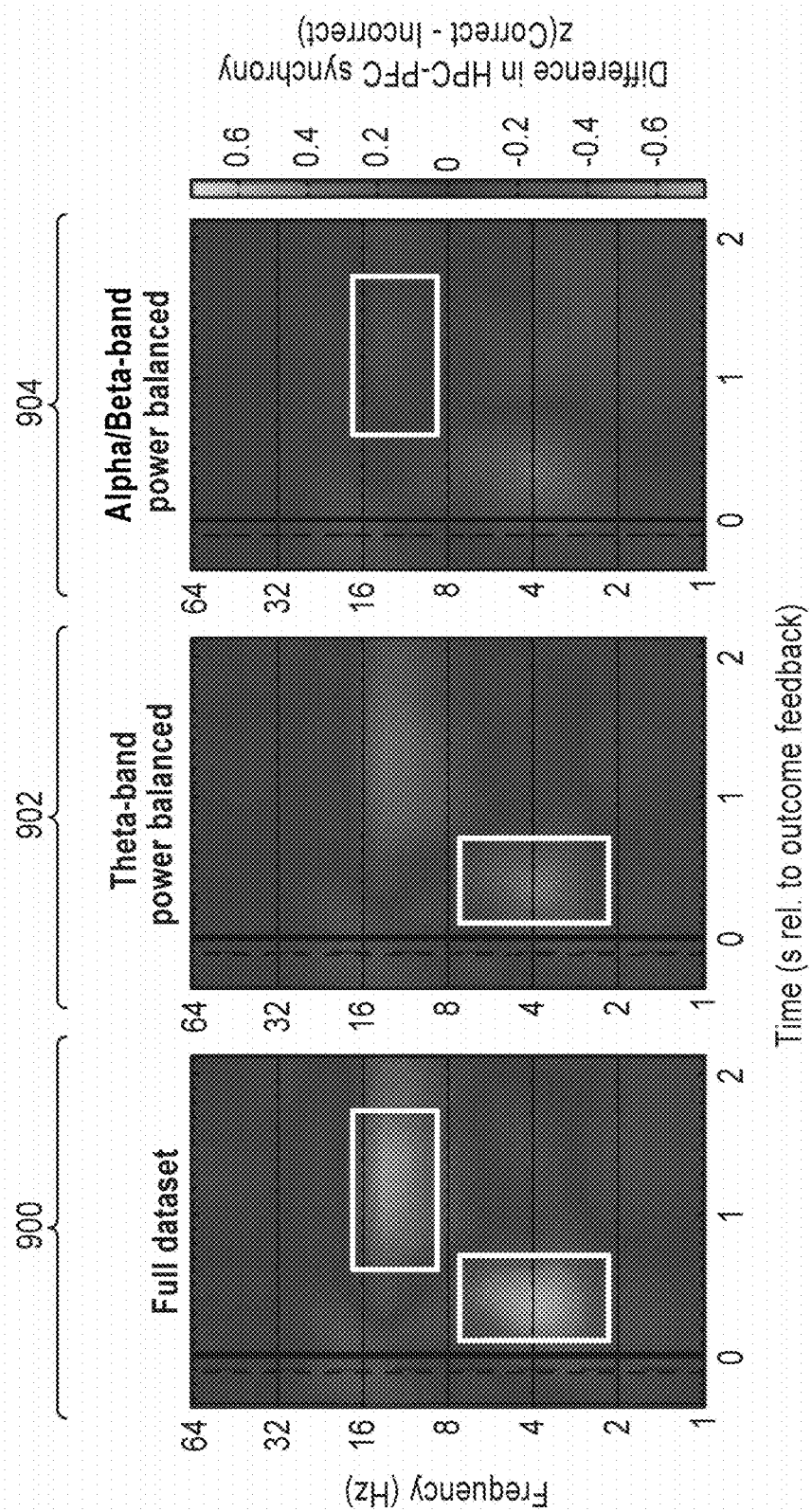
FIG. 9A is a series of spectrograms illustrating the mean z-scored difference in HPC-PFC synchrony between correct and incorrect trials for the full dataset, and for data where power pooled within the theta-band or alpha/beta-band regions of interest was balanced across trial outcomes, respectively, in accordance with some embodiments.
Figure 9B:
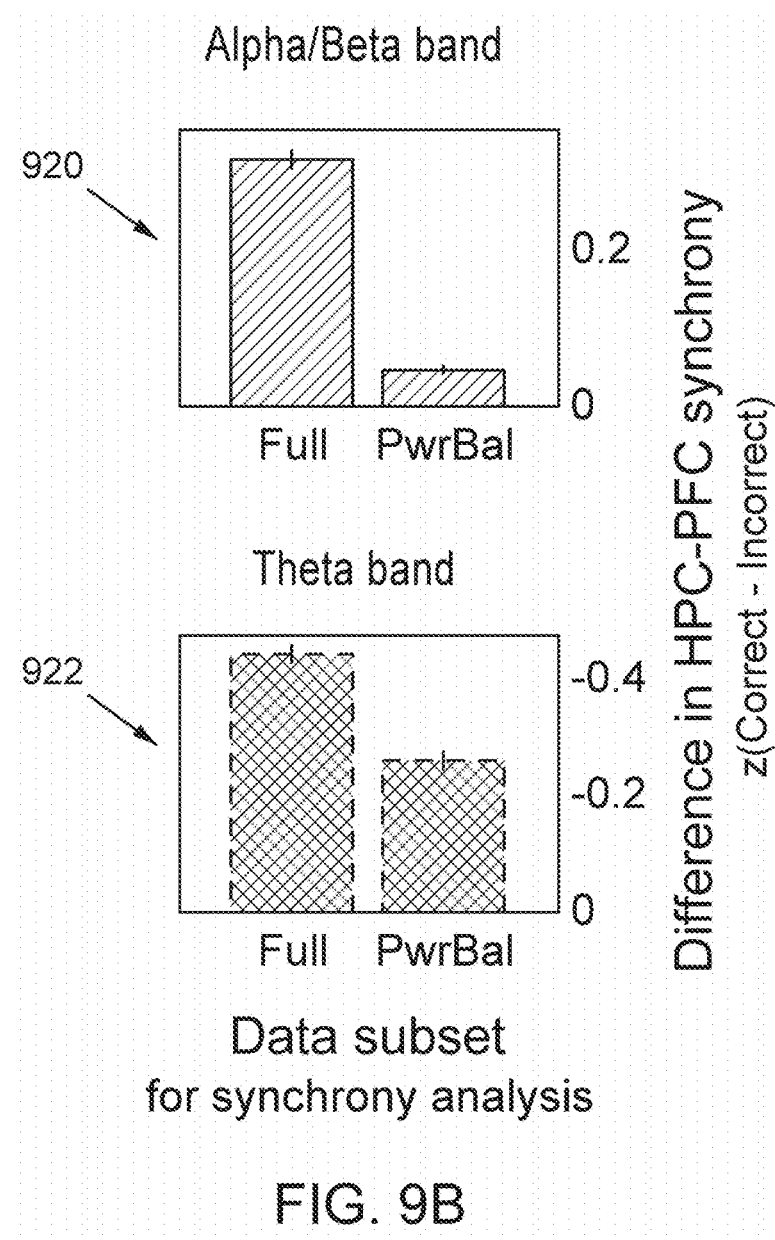
FIG. 9B is a series of plots illustrating full versus power-balanced data comparison by plotting the mean z-scored synchrony difference pooled within the alpha/beta-band and theta-band regions of interest, for the full dataset and a data subset created by balancing power in the given region of interest, respectively, in accordance with some embodiments.

Outcome selectivity in cross-area synchrony could not, however, be fully attributed to local power differences, as it remained significant even when band-specific power was balanced across correct and incorrect trials. That is, balancing band-limited power does not eliminate trial outcome information in HPC-PFC synchrony in accordance with some embodiments. FIG. 9A shows the mean z-scored difference in HPC-PFC synchrony between correct and incorrect trials for the full dataset 900, and for data where power pooled within the theta-band 902 or alpha/beta-band 904 region of interest was balanced across trial outcomes. Power balancing was performed using a stratification method that trims extreme power values from each condition, until the histogram of trial power values is closely matched between compared conditions (correct, incorrect outcomes). FIG. 9B summarizes full vs. power-balanced data comparison by plotting the mean (±SEM) z-scored synchrony difference pooled within the alpha/beta-band 920 and theta-band 922 regions of interest, for the full dataset (left bars) or a data subset created by balancing power in the given region of interest (right bars). Though power balancing reduces the effect of trial outcome on neural synchrony, both frequency bands remain significantly different from zero ($p<10-4$ for both; 1-sample bootstrap test). This confirms there is a specific effect of outcome on HPC-PFC synchrony, beyond any possible artifactual effects due to differences in power.

Directional influences were measured between the PFC and HPC in two ways. First, the mean phase lag was calculated between LFPs on each pair of electrodes, as shown in Equation (6):

$$\varphi_{lag}(f, t) = \text{angle}\left(\frac{1}{nTrials}\sum_{tri=1}^{nTrials} \exp(i[\varphi_{tri,elec1}(f, t) - \varphi_{tri,elec2}(f, t)])\right) \quad (6)$$

To test whether the distribution of phase lags across all electrode pairs was significantly different from zero—suggestive of a directionality between the two signals—a circular bootstrap test was used.

Though consistent phase lags much smaller than a full oscillatory cycle are suggestive of directional influences, they are in principle ambiguous because of the cyclic nature of the signals. Therefore, the generalized partial directed coherence (GPDC) also was computed between pairs of LFPs in each area. GPDC is a frequency-domain analog of Granger causality, which measures putative causality in terms of the degree to which one signal (LFP) can be predicted by past values of another signal (LFP from a distinct electrode), with its own past history factored out. This approach is based on a multivariate autoregressive (MVAR) model fit to pairs of LFP time series, as shown in Equation (7):

$$X(t) = \sum_{k=1}^{p} A_k X(t-k) + \sum(t) \quad (7)$$

where X(t) is the data vector of the pair of LFP signals at time t, $A_k$ is the 2×2 matrix of autoregressive coefficients at the $k^{th}$ time lag, p is the maximum number of lags (model order), and $\Sigma(t)$ the residual prediction error. The Bayesian Information Criterion was evaluated on a few representative LFP pairs to select a fixed model order of 17 (max lag 85 ms). MVAR models were fit separately on LFP data within each sliding time window (500 ms width, 250 ms step between successive windows), trial window, and task condition. The parameters of the MVAR model in each window were estimated using Morf's modification of the Levinson-Wiggins-Robinson algorithm. The fitted MVAR parameters were then transformed from the time domain into the frequency domain, as shown in Equation (8):

$$\overline{A}(f) = I - \sum_{k=1}^{p} A_k \exp(-2\pi i k f / f_{samp}) \quad (8)$$

where I is the p×p identity matrix, $f_{samp}$ is the LFP sampling rate, and the spectral coefficients $\overline{A}(f)$ were evaluated at 1 Hz steps from 1-64 Hz. The GPDC reflecting the directional influence of $LFP_1$ on $LFP_2$ is then calculated as, as shown in Equation (9):

$$GPDC_{2 \leftarrow 1} = \frac{\frac{2}{\sigma_2}|\overline{A}_{2 \leftarrow 1}(f)|}{\sqrt{\frac{1}{\sigma_2^2}|\overline{A}_{2 \leftarrow 1}(f)|^2 + \frac{1}{\sigma_1^2}|\overline{A}_{1 \leftarrow 1}(f)|^2}} \quad (9)$$

where $\sigma_k^2$ is the variance of the prediction error for channel k. Similar results were obtained using classical spectral Granger causality. For display purposes only, LFP causality plots were smoothed with a 2D Gaussian with SDs [1 Hz, 100 ms] and interpolated to a finer sampling grid.

Theta and alpha/beta synchrony differed in the direction of putative causal influence. For theta frequencies, the phase of HPC LFPs lagged behind PFC, consistent with a PFC to HPC directionality; the reverse was true for alpha/beta frequencies. This was confirmed using GPDC to measure the degree to which signals can predict each other's future values.

Figure 10:
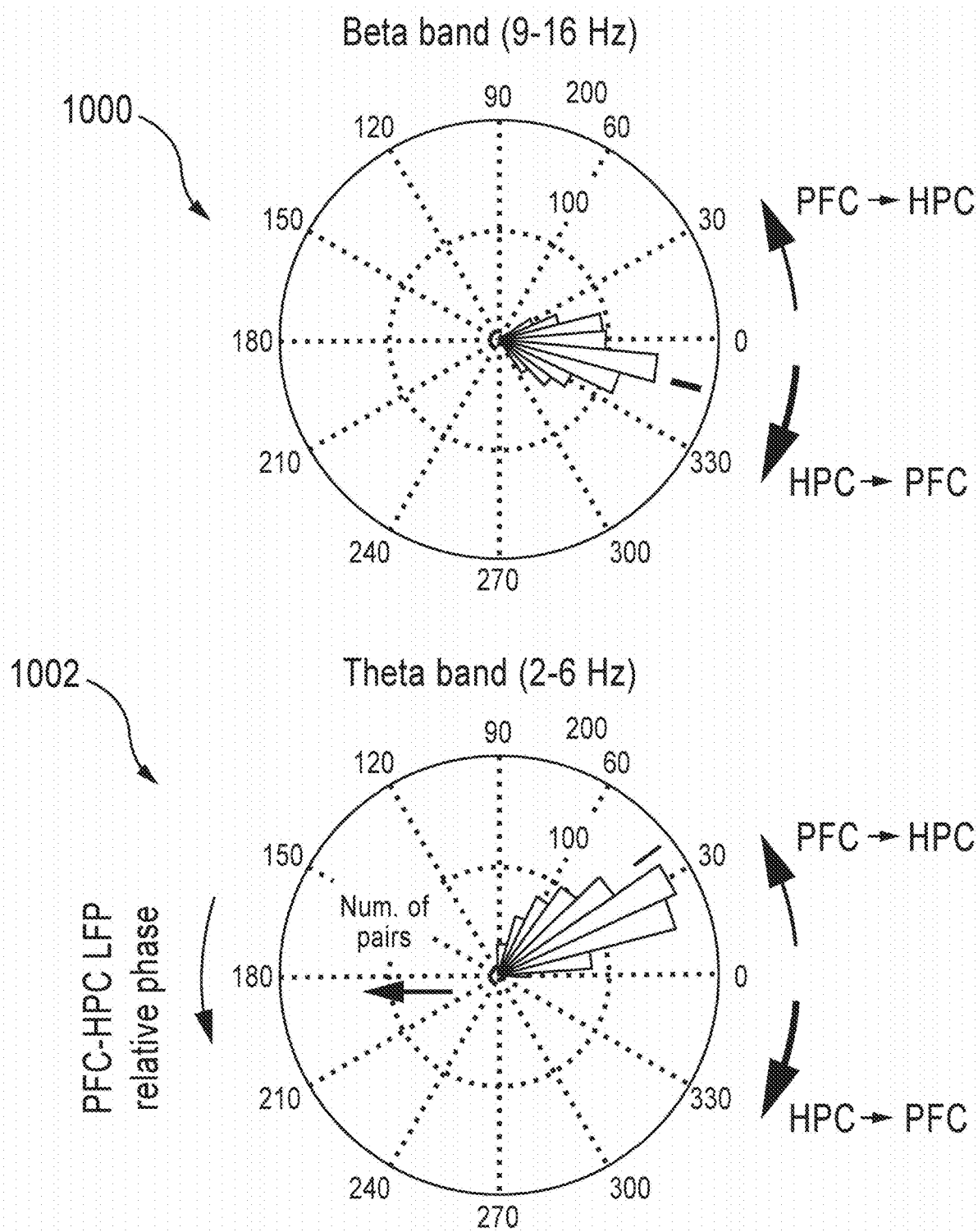
FIG. 10 is a series of histograms illustrating mean PFC-HPC local field potential phase lag for all electrode pairs for alpha/beta-band and theta-band regions of interest, respectively, in accordance with some embodiments.

FIG. 10 includes histograms of mean PFC-HPC LFP phase lag for all 970 electrode pairs for alpha/beta-band 1000 and theta-band 1002 regions of interest in accordance with some embodiments. Tick marks indicate mean across all pairs. HPC leads for alpha/beta frequencies ($p<10^{-4}$; bootstrap test vs. zero phase lag), while PFC leads for theta ($p<10^{-4}$).

GPDC also revealed oscillatory interactions in the theta and alpha/beta bands with stronger theta influence from PFC to HPC (p<10-4) and stronger alpha/beta influence (solid lines) from the HPC to PFC (p<10-4, 2-way causal direction×trial outcome ANOVA). As above, theta and alpha/beta interactions were stronger for incorrect and correct trials, respectively (p<10-4 for both). With learning, there were significant decreases in incorrect-reflecting PFC to HPC theta influences (p=0.021) and correct-reflecting HPC to PFC alpha/beta influences (p=0.04, permutation test on early vs. late learning) suggesting these interactions may be most important during the early stages of learning. In contrast, initially weak PFC to HPC alpha/beta influences reflecting correct outcomes increased with learning (p<10-4), eventually becoming even stronger than the HPC to PFC direction (p=10-3; interaction in 2-way causal-direction×learning-stage ANOVA).

Figure 11A:
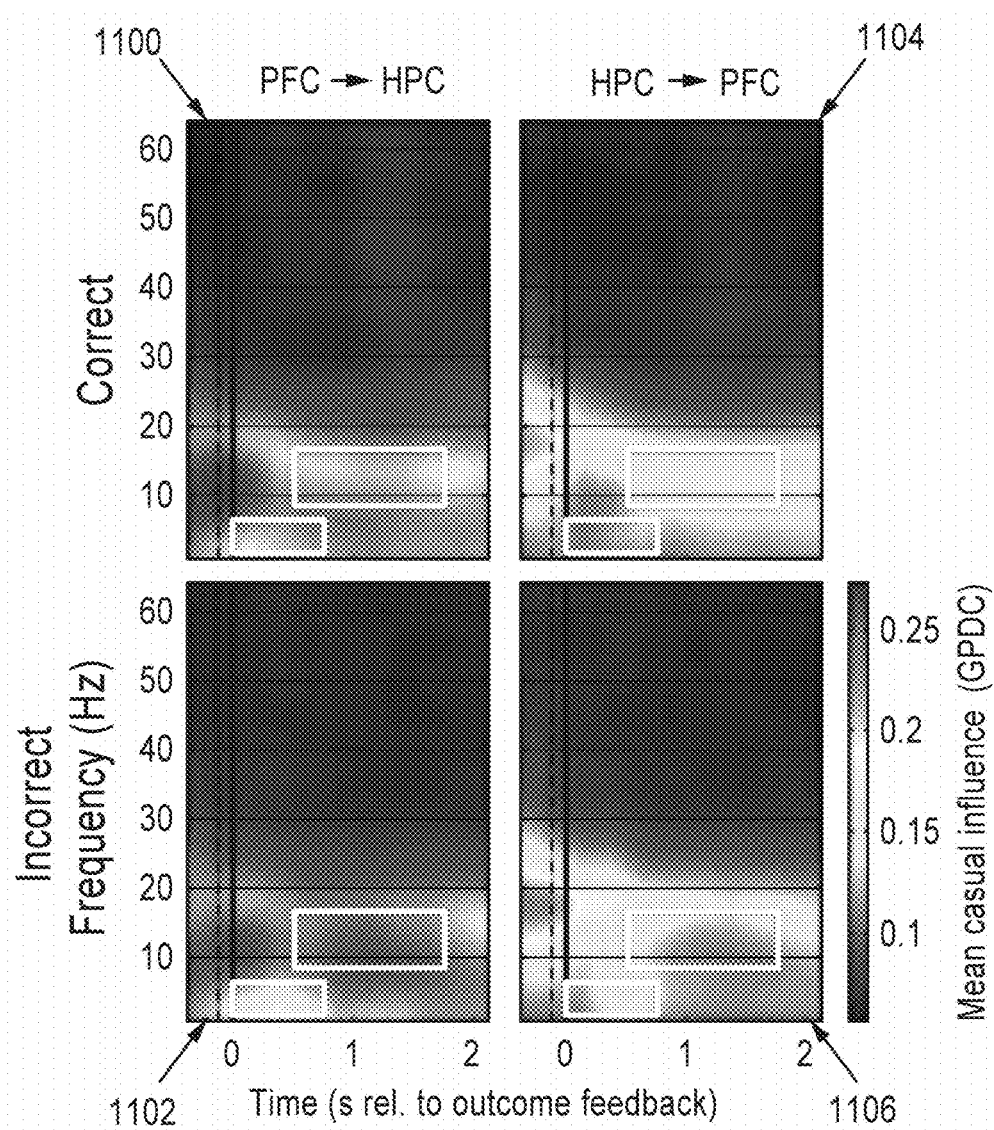
FIG. 11A is a series of spectrograms illustrating frequency-domain directional influences from PFC to HPC and from HPC to PFC, respectively, in accordance with some embodiments.
Figure 11B:
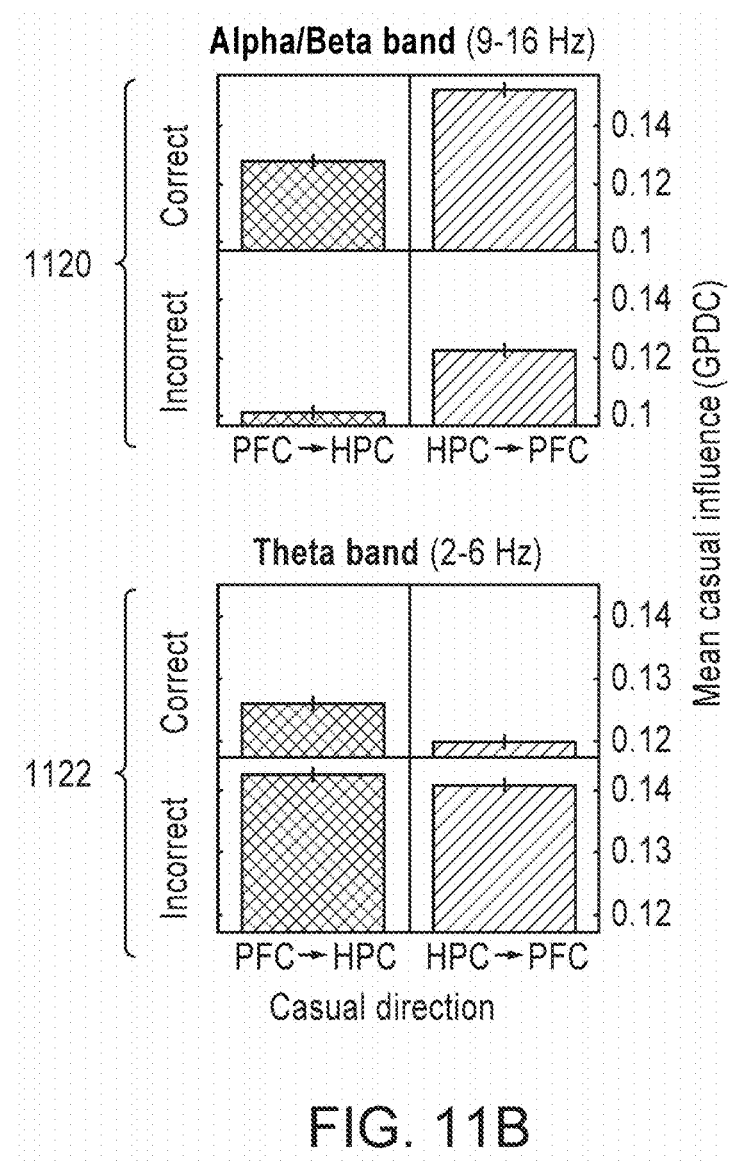
FIG. 11B is a series of plots illustrating the mean generalized partial directed coherence pooled within the alpha/beta-band and theta-band regions of interest, respectively, in accordance with some embodiments.
Figure 11C:
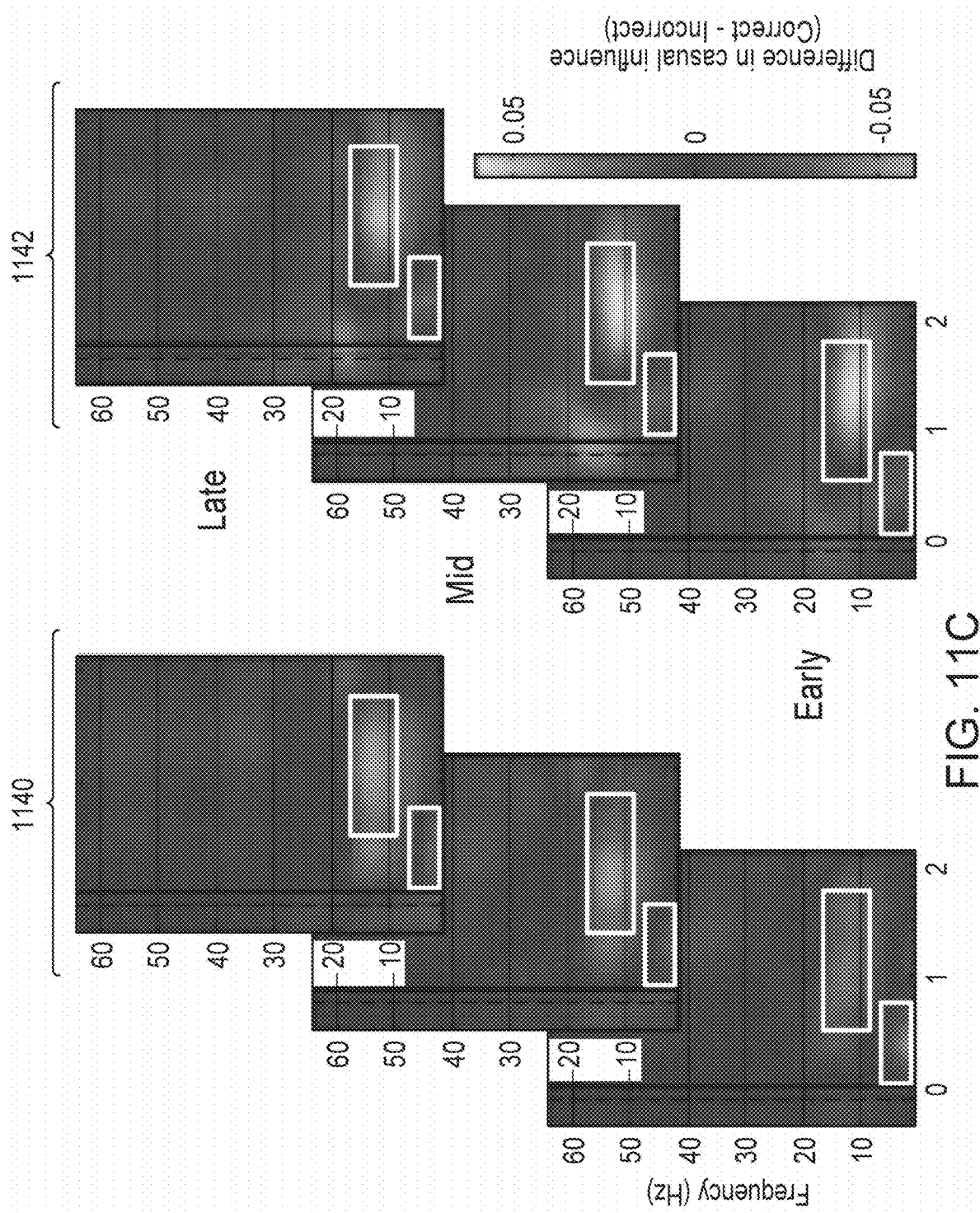
FIG. 11C is a diagram including series of spectrograms illustrating the difference in directional strength between correct and incorrect outcomes separately for PFC to HPC and HPC to PFC, respectively, in accordance with some embodiments.
Figure 11D:
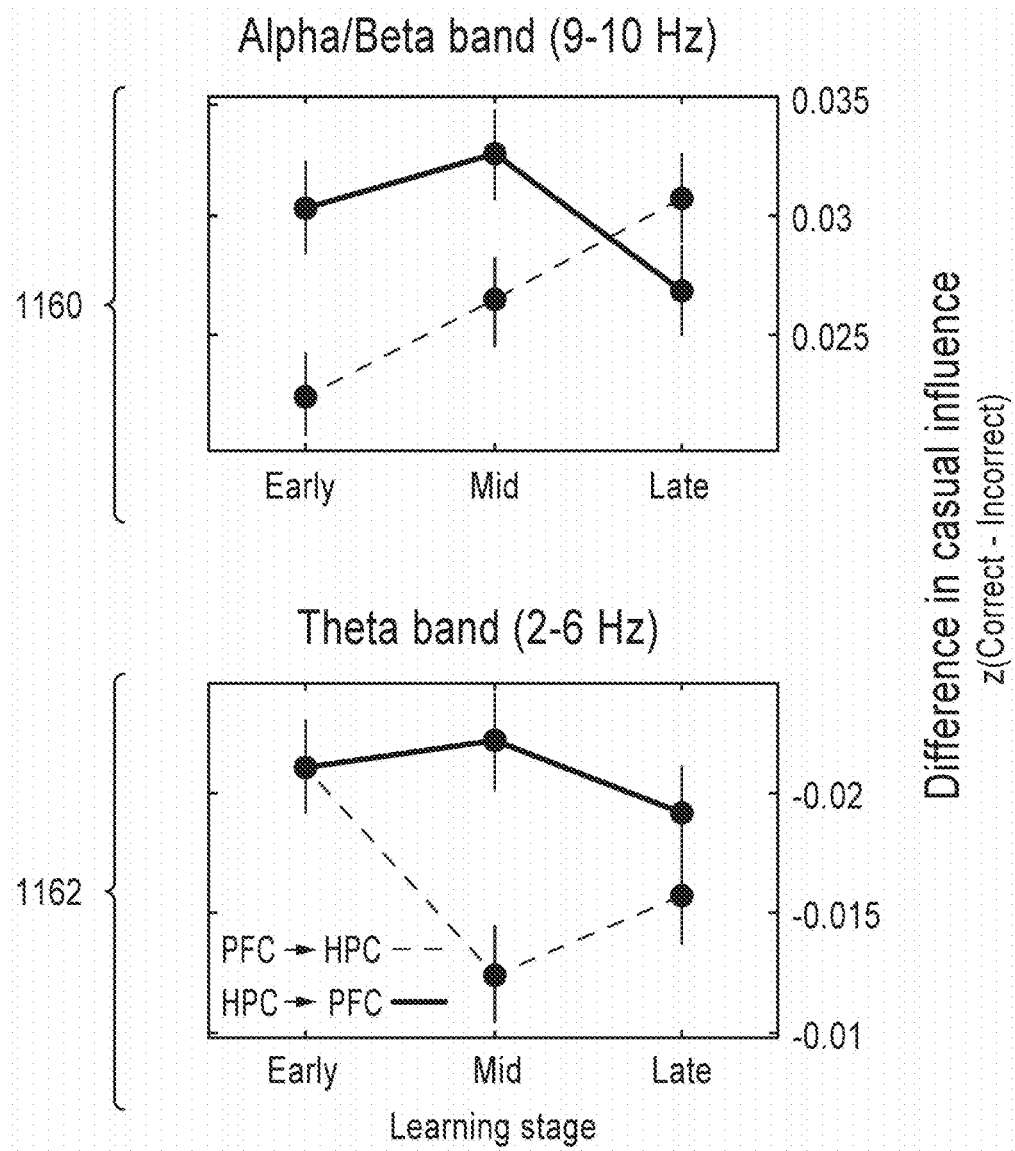
FIG. 11D is a series of plots illustrating observed learning effects on directionality within the alpha/beta-band and theta-band regions of interest, respectively, as a function of learning stage in accordance with some embodiments.

FIG. 11A includes spectrograms plotted across time (x-axis) and frequency (y-axis) to show frequency-domain directional influences (generalized partial directed coherence) from PFC to HPC following correct trials 1100 and incorrect trials 1102, and from HPC to PFC following correct trials 1104 and incorrect trials 1106. FIG. 11B summarizes these directional effects by plotting the mean (±SEM) GPDC pooled within the alpha/beta-band 1120 and theta-band 1122 regions of interest. Overall, alpha/beta-band influences are stronger from HPC to PFC and for correct trials, while theta-band influences are stronger from PFC to HPC and for incorrect trials in accordance with some embodiments. FIG. 11C illustrates cross-area directional influences across learning by plotting the difference in directional strength (GPDC) between correct and incorrect outcomes separately for each direction, PFC to HPC 1140 and HPC to PFC 1142 and learning stage (bottom to top). FIG. 11D summarizes learning effects. With learning, theta interactions 1160 showed a decreasing trend, while alpha/beta interactions 1162 shifted from a HPC→PFC to PFC→HPC directionality in accordance with some embodiments.

These results suggest different roles and interactions between the PFC and HPC during object associative learning. Only PFC neurons showed neural correlates of learning the paired associates. The HPC was more engaged when feedback was given about whether the trial was correct or incorrect. Early in learning, incorrect outcomes activated HPC neurons and promoted cross-area theta synchrony with a stronger influence from the PFC to the HPC. Correct outcomes, in contrast, promoted alpha/beta-band synchrony that was initially stronger in the HPC to PFC direction. But as learning progressed, correct outcomes increasingly evoked PFC to HPC alpha/beta-band influences and HPC neuronal spiking. This shift in HPC outcome coding (and other properties) distinguishes it from static reward-prediction-error signals in subcortical structures, but may reflect the functional shift from early error-prone learning to consolidation, which is enhanced by positive feedback.

Figure 12A:
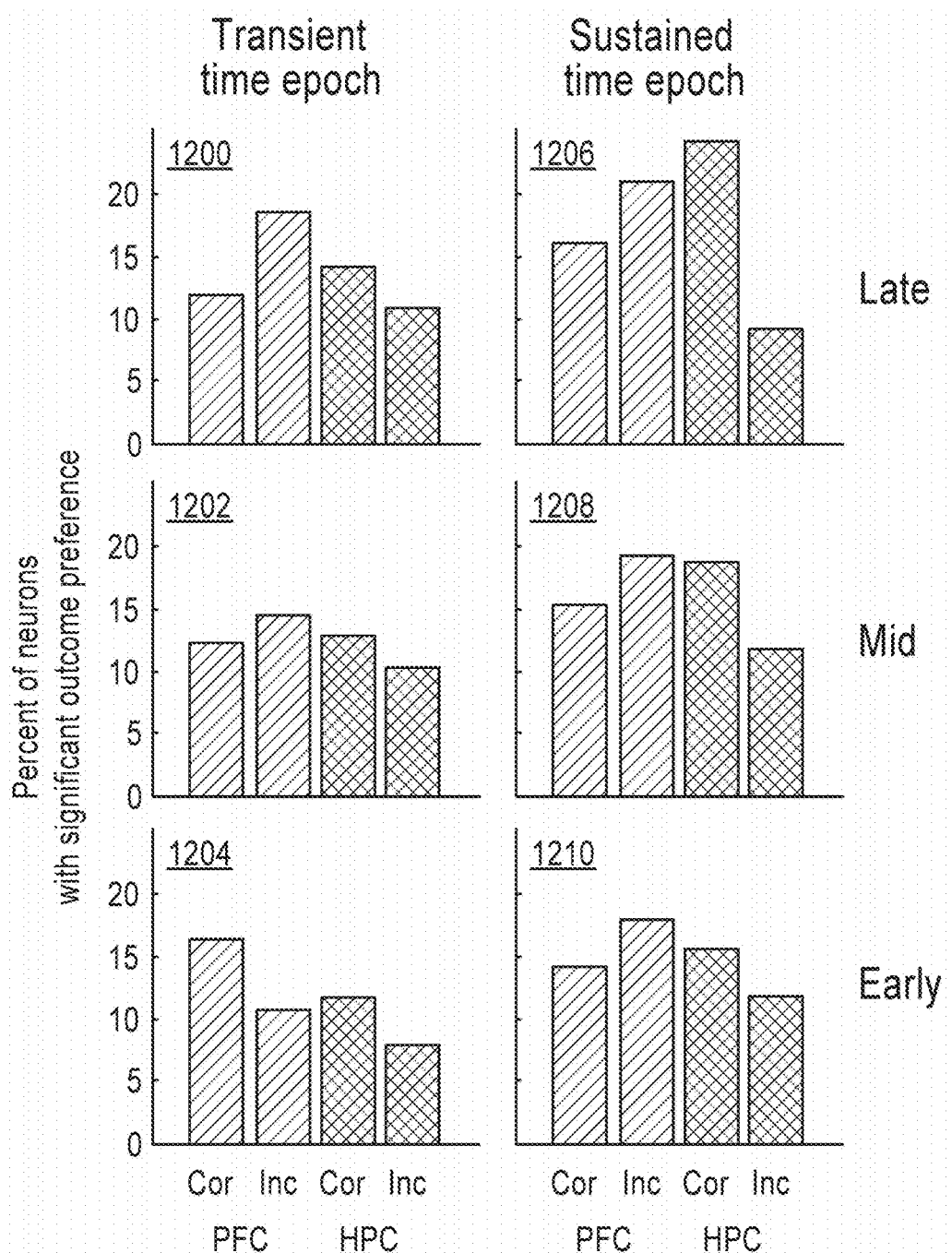
FIG. 12A is a series of plots illustrating a percent of neurons in PFC and HPC with a significant preference for correct or incorrect outcomes in accordance with some embodiments.

The PFC and the HPC neuronal trial outcome signals are distinct from subcortical reward prediction error signals. Roughly equal numbers of neurons show stronger activity for correct and incorrect outcomes in accordance with some embodiments. FIG. 12A includes plots showing the percent of neurons in PFC (n=319) and HPC (n=199) with a significant preference for correct (Cor) or incorrect (Inc) outcomes ($p<0.05$, permutation test). Values are plotted separately for early, mid, and late learning stages (bottom to top), and time epochs capturing transient (left; 100 ms to 500 ms) and sustained (right; 600 ms to 1350 ms) response components. These results are in contrast to previous results from the ventral tegmental area and lateral habenula, which show strong biases toward positive and negative reward prediction errors (roughly, uncertain correct and incorrect outcomes), respectively.

Figure 12B:
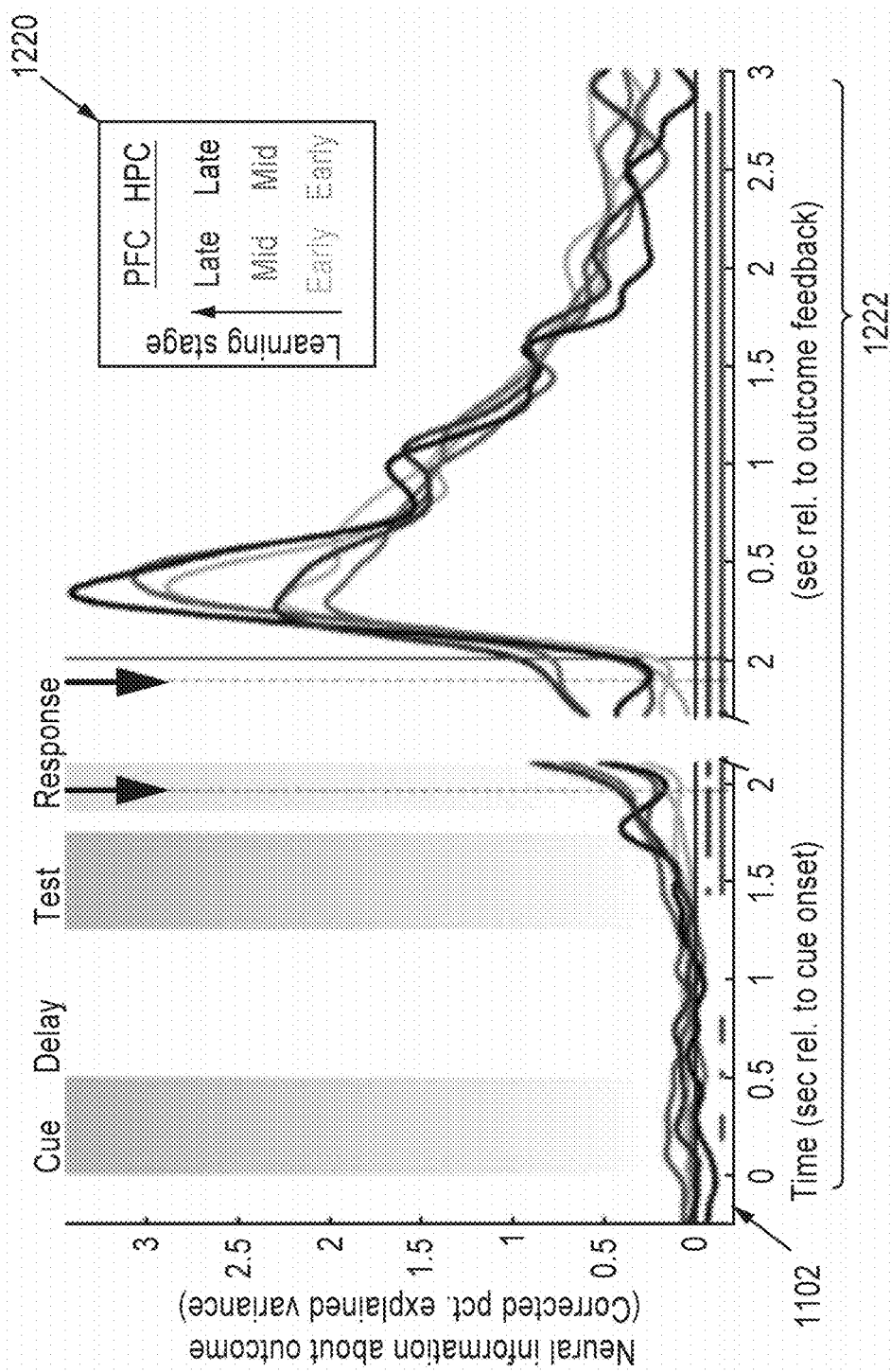
FIG. 12B is a diagram including a plot illustrating population mean percent variance explained by trial outcome as a function of time during and after the trial, separately for PFC and HPC and learning stages in accordance with some embodiments.

FIG. 12B is a plot of population mean percent variance explained by trial outcome (correct vs. incorrect) as a function of time during (left) and after (right) the trial, separately for PFC and HPC and learning stages (see legend 1220). Tick marks 1222 represent time points with significant explained variance during the late learning stage ($p<0.05$, uncorrected, bootstrap test). In the ventral tegmental area and lateral habenula, as reward becomes more predictable during learning, activation shifts from the post-response outcome feedback epoch to earlier trial events predictive of reward. In contrast, post-response trial outcome information in PFC and HPC is present throughout learning, with little shift to earlier time points.

These properties, and the learning-related shift from bias toward encoding incorrect to correct outcomes in HPC, distinguish the outcome signals from the static reward prediction error signals found in areas such as the ventral tegmental area and lateral habenula. However, it has been shown neural activity that changes with context—such as the stage of new memory acquisition/consolidation—may still easily be "read out" by downstream neurons, even with a simple linear decoder.

The HPC is critical for formation of explicit memories. Rodent neurophysiological studies suggest it acquires spatial memories and consolidates them in the neocortex, including the PFC. The primate HPC shows rapid activity changes related to spatial associative learning. But the HPC is also known to be critical for non-spatial memory in rodents and especially in primates, where it plays a general role in explicit memory formation. Lesion studies have suggested that perirhinal cortex—part of the medial temporal lobe system that includes the HPC—may be more critical for object associative learning than the HPC, and neural correlates of object associations have been seen in perirhinal, prefrontal, and inferotemporal cortex. However, these studies examined associations that were familiar or learned gradually (over days or weeks), situations known to favor neocortical representation. The results disclosed herein suggest that rapid acquisition of object associations also occurs in the neocortex, not the HPC, perhaps particularly the PFC given its importance for behavioral flexibility. Object associations may lack the context required for explicit HPC representation.

Both the HPC and PFC signal trial outcome, differentiating between correct and error trials. The results suggest this information is communicated between HPC and PFC via synchrony at different frequencies: theta for incorrect and alpha/beta for correct. Human EEG also shows theta oscillations with a frontal source reflecting conflict or error; the results suggest these oscillations are propagated to HPC during learning. Human and animal studies suggest that oscillatory activity is associated with memory encoding and retrieval, as well as other cognitive processes. Higher frequency (gamma) oscillations are thought to underlie the transient formation of local neuronal ensembles, while lower frequencies may recruit larger networks due to their longer integration times. Thus, the lower frequency (theta and alpha/beta) synchrony observed may reflect formation of larger PFC-HPC networks.

Beta oscillations are ideal for maintaining active cell assemblies, and their associated cognitive states. This is consistent with the idea that beta might have a role in maintaining neural representations active during correct associations. Studies of synaptic plasticity have also shown that low-frequency synaptic stimulation fosters long-term depression, while high-frequency stimulation fosters long-term potentiation, with the crossover point at about 8 Hz to about 10 Hz. PFC-HPC theta interactions may therefore have weakened synapses active during incorrect associations, while alpha/beta interactions strengthened those active for the correct associations.

In sum, these observations show that rapid formation of non-spatial associations may occur within the PFC, not the HPC. The main role of the HPC was to provide feedback signals that may guide neocortical learning. The results also provide further support for the idea that synchrony in different frequency bands may have functionally different roles in neural communication.

Systems and Methods for Enhancing and/or Disrupting Memory Formation and Storage Through research and analysis, the inventors have determined that the PFC and the HPC synchronize their oscillations at specific frequencies when memory associations are formed or reconsolidated. For example, when a subject forms a correct memory association, oscillations in the PFC and the HPC synchronize at beta frequencies. However, when a subject makes a mistake or attempts to form an incorrect memory association, oscillations in the PFC and the HPC synchronize at theta frequencies. Thus, beta synchrony indicates to the brain that the subject should "store" the correct memory association, while theta synchrony indicates to the brain that the subject should "forget" the incorrect memory association.

The inventors have further recognized and appreciated that the external application of synchronized oscillations may be used to train the brain to reinforce and/or weaken associations during memory formation and/or reconsolidation. For example, oscillations with beta frequencies may be applied to artificially create beta synchrony between the PFC and the HPC, and oscillations with theta frequencies may be applied to artificially create theta synchrony between the PFC and the HPC.

According to some embodiments, electrical stimulation is applied to the brain (e.g., through electrodes in substantial contact with the scalp). For example, the electrical stimulation may be safely applied to the PFC and the HPC using low-voltage TES, which involves passing a very low current between electrodes and has been used only to administer DC currents; however, brain activity naturally waxes and wanes in phase with endogenous rhythms. By adapting TES to enhance these rhythms by administering AC currents, the inventors have recognized and appreciated that TES may be used to enhance specific brain activities in a more precise, physiological manner (i.e., by selectively administering electrical currents oscillating at beta frequencies and/or theta frequencies).

Figure 13:
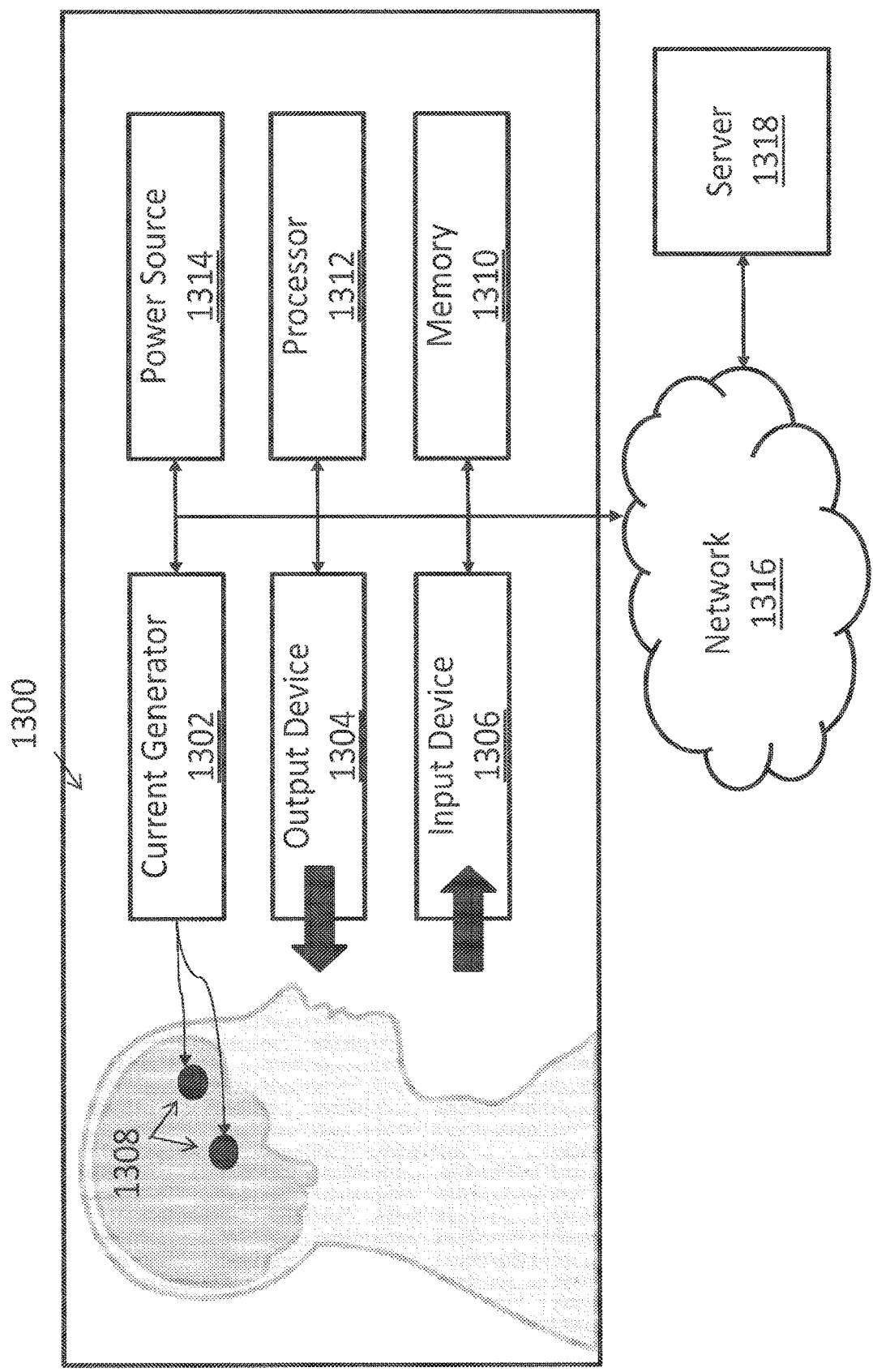
FIG. 13 is a diagram illustrating a system for selectively reinforcing and/or weakening memory associations in accordance with some embodiments.

FIG. 13 illustrates a system 1300 for selectively reinforcing or weakening memory associations in accordance with some embodiments. The system may include at least one current generator 1302 for providing an electrical current. The electrical current may include a plurality of oscillating pulses with at least one predetermined frequency.

The system may also include a user interface, including at least one output device 1304 for delivering at least one sensory stimulus to a user, at least one user input device 1306 for registering at least one response of the user to the at least one sensory stimulus, and at least one electrode pair 1308 for detachable attachment to or proximate to the user's scalp.

The at least one output device 1304 for delivering the at least one sensory stimulus to the user may include a visual display (e.g., a computer monitor, a touchscreen, etc.), a printer, a refreshable tactile or haptic (e.g., braille) display, and/or a speaker (e.g., computer speakers, headphones, earbuds, etc.).

The sensory stimulus may be visual, audible, tactile, olfactory, and/or gustatory. A sensory stimulus may include anything from a digital image, an alphanumeric character, a braille character, and/or an audible sound to an explicit objective assessment question. A sensory stimulus may require the user to select, via the at least one input device, an indication of true or false, an answer from a plurality of presented answers, or a match from a plurality of presented matches. Alternatively, a sensory stimulus may require the user to supply at least one of an alphanumeric character, a braille character, and an audible sound via the at least one input device.

The at least one input device 1306 for registering at least one response of the user to the at least one sensory stimulus may include a keyboard, a scanner, a camera, a microphone, a pointing device (e.g., a joystick, stylus, mouse, trackball, touchpad, etc.), a touchscreen, and/or a refreshable tactile or haptic (e.g., braille) display.

The system 1300 may include at least one sensor for calibrating system 1300, detecting, and/or measuring physiological input signal from the user, such as endogenous neural activity and/or physiological markers of stress. A sensor may include a heart rate monitor, an ECG system, a blood pressure monitor, a respiration rate monitor, a thermometer, an fMRI system, an EEG system, and/or an MEG system. A sensor may be in addition to the at least one input device 1306, or the at least one input device 1306 may include the sensor. The system 1300 may also include an analog-to-digital converter coupled to the at least one sensor for electronically converting the at least one physiological input signal from the at least one sensor to a plurality of digital samples of the at least one physiologic signal relating to at least one physiological parameter.

A response may be a selection of an indication of true or false, a selection of an answer from a plurality of presented answers, or a selection of a match from a plurality of presented matches. A response may be an alphanumeric character, a braille character, and/or an audible sound. A response may also relate to a change in a physiological parameter of the user. The physiological parameter may relate to the user's heart rate, blood pressure, body temperature, respiration rate, neural activation, and/or neural oscillation.

The at least one electrode pair 1308 may be configured to stimulate at least one specific portion of the user's brain with the electrical current based at least in part on the at least one response of the user to the at least one sensory stimulus. The at least one specific portion of the user's brain may include the PFC, the HPC, or some combination thereof.

The at least one electrode pair 1308 may be a plurality of electrode pairs. Each electrode of the at least one electrode pair 1308 may be a transcranial electrode and/or an alternating current electrode. A conductive gel and/or paste may be used to reduce impedance between each electrode of the at least one electrode pair 1308 and the user's scalp. Wiring may be used to connect each electrode of the at least one electrode pair 1308 to the at least one current generator 1302.

The system may include at least one memory 1310 for storing processor-executable instructions. The at least one memory 1310 may also store the at least one sensory stimulus, the at least one response of the user to the at least one stimulus, and/or at least one predetermined standard for determining whether the at least one response of the user to the at least one stimulus is desired or undesired.

The system may include at least one processor 1312 for executing the processor-executable instructions. The at least one processor 1312 is communicatively coupled to the at least one current generator 1302, the at least one output device 1304, the at least one input device 1306, the at least one memory 1310, at least one power source 1314, and a network 1316 connected to a server 1318.

The at least one power source 1314 may supply low voltage to the at least one current generator 1302. The power source 1314 may supply about 5-20 volts. The electrical current may have a current flow of about 0.25-1.5 milliamps. The frequency and/or an amplitude of the electrical current may be regulated by, for example, the at least one processor 1312.

The network 1316 may be used to receive information (e.g., the at least one sensory stimulus and/or at least one predetermined standard for determining whether the at least one response of the user to the at least one stimulus is desired or undesired) and/or transmit information (e.g., the at least one response of the user to the at least one stimulus and/or the determination of whether the at least one response of the user to the at least one stimulus is desired or undesired) to server 1318, which may be used to store information. The software and/or information stored in the memory 1310 and/or server 1318 also may be customizable, allowing, for example, a user to input one or more new or custom components, steps, stimuli materials, and/or predetermined standards into the system 1300.

Upon execution of the processor-executable instructions, the at least one processor 1312 may control the user interface to deliver a first sensory stimulus to the user via the at least one output device 1304, and register the at least one response of the user to the first sensory stimulus via the input device 1306. The at least one processor 1312 may further process the at least one response of the user to the first sensory stimulus to determine whether an underlying memory association is desired or undesired according to at least one predetermined standard.

Based on whether the underlying memory association is desired, the at least one processor 1312 may further set the at least one predetermined frequency to be a beta frequency if the underlying memory association is desired or a theta frequency if the underlying memory association is undesired. The beta frequency may be a frequency between about 12 Hz and about 40 Hz. For example, the beta frequency may be about 16 Hz. The theta frequency may be a frequency between about 3 Hz and about 8 Hz. For example, the theta frequency may be about 4 Hz.

The at least one processor 1312 may then control the at least one current generator 1302 to generate an electrical current with either the beta frequency or the theta frequency, and control the user interface to administer the electrical current, via the at least one electrode pair 1308, thereby stimulating the at least one specific portion of the user's brain with the electrical current based at least in part on the at least one response of the user to the first sensory stimulus so as to reinforce or weaken the underlying memory association.

In some embodiments, the system may only be used for selectively weakening memory associations. The at least one processor 1312 may process the at least one response of the user to the first sensory stimulus to determine whether an underlying memory association is undesired according to at least one predetermined standard. If the underlying memory association is undesired, the system 1300 may administer the electrical current at a theta frequency, via the at least one electrode pair 1308, thereby stimulating the at least one specific portion of the user's brain with the electrical current based at least in part on the at least one response of the user to the first sensory stimulus so as to weaken the underlying memory association. If the underlying memory association is not undesired, no electrical current or an electrical current that does not have a theta frequency may be applied.

In some embodiments, the system may only be used for selectively reinforcing memory associations. The at least one processor 1312 may process the at least one response of the user to the first sensory stimulus to determine whether an underlying memory association is desired according to at least one predetermined standard. If the underlying memory association is desired, the system 1300 may administer the electrical current at a beta frequency, via the at least one electrode pair 1308, thereby stimulating the at least one specific portion of the user's brain with the electrical current based at least in part on the at least one response of the user to the first sensory stimulus so as to reinforce the underlying memory association. If the underlying memory association is not desired, no electrical current or an electrical current that does not have a beta frequency may be applied.

FIG. 14 illustrates a method 1400 for selectively reinforcing or weakening memory associations in accordance with some embodiments. In step 1402, a system is calibrated for a particular user. Some embodiments may include selecting, calibrating, and/or customizing the at least one output device, the at least one input device, a placement of the at least one electrode pair, a type of one or more stimuli, a content of one or more stimuli, a type of response, the at least one predetermined standard, an amplitude of the electrical current, and the at least one predetermined frequency. Some embodiments may include attaching the at least one electrode pair to or proximate to the user's scalp, applying a conductive gel and/or paste between each electrode of the at least one electrode pair and the user's scalp, and/or attaching connecting each electrode of the at least one electrode pair to the at least one current generator.

Additional components and/or steps may be used to calibrate embodiments for an individual user. Some embodiments may include a calibration procedure to determine at least one optimal stimulation location for an individual user based on measurements from at least one sensor of endogenous neural oscillations under stimulus and response conditions similar to those during the intended stimulation. For example, at least one stimulation electrode may be placed at one or more sites where measured endogenous beta oscillation power is strongest following desired associations and/or where endogenous theta oscillation power is strongest following undesired associations.

Since the precise frequency of neural oscillations varies between individuals, some embodiments may include a calibration procedure to determine peak endogenous beta and/or theta oscillation frequencies for an individual user based on measurements from at least one sensor under stimulus and response conditions similar to those during the intended stimulation. At least one optimal stimulation frequency may then be set by a processor to, for example, match the frequency of the individual's endogenous oscillations.

Since stimulation is likely to be most effective if delivered in-phase with ongoing endogenous oscillations, some embodiments may include a real-time calibration procedure whereby the phase of endogenous beta and/or theta oscillations is measured from at least one sensor and used by a processor to time the onset of oscillatory stimulation such that the endogenous and synthetic oscillations are approximately in phase.

In step 1404 of method 1400, at least one first sensory stimulus is delivered to the user. In step 1406, at least one response of the user to the first sensory stimulus is received. In step 1408, the at least one response of the user to the first sensory stimulus is compared to at least one predetermined standard to determine whether an underlying memory association is desired or undesired. The at least one predetermined standard may include a correct response to an associated sensory stimulus, a response time, a magnitude of a physiological parameter of the user, and/or a frequency of a physiological parameter of the user.

If the underlying memory association is desired, at least one predetermined frequency is set to a beta frequency in step 1410. If the underlying memory association is undesired, the at least one predetermined frequency is set to a theta frequency in step 1412. In step 1414, an electrical current, including a plurality of oscillating pulses with the at least one predetermined frequency—either the beta frequency or the theta frequency—is generated and administered to the user's scalp via at least one electrode pair to stimulate at least one specific portion of the user's brain with the electrical current.

Following the administration of the electrical current, in step 1416, a decision is made whether to repeat the method or not. Similarly, a decision is made whether to repeat the method or not in step 1416 if the underlying memory association was determined to be neither desired nor undesired in step 1408. The method may be repeated with the first sensory stimulus or with a second sensory stimulus. The method may be repeated as many times as wanted, with as many sensory stimuli as wanted.

Example 1

Some embodiments may be used to reinforce or enhance a desired memory association. For example, Alzheimer's disease may have a profound effect on explicit memory. Patients with Alzheimer's disease may have difficulty, among other functions, remembering where items are placed in new or unfamiliar environments. Thus, some embodiments may be practiced by or with an Alzheimer's patient (e.g., in the company of a therapist or medical provider) to, for example, reinforce object-location associations in an unfamiliar environment.

According to some embodiments, a system may be selected, calibrated, and/or customized for a particular Alzheimer's patient. At least one electrode pair may be attached to or proximate to the patient's scalp with a conductive gel between each electrode and the scalp, each electrode being connected to at least one current generator.

A sensory stimulus in the form of a digital image of an object (e.g., keys) may be delivered to the patient via a touchscreen. The touchscreen also presents one or more digital images of at least two locations (e.g., a basket and a hook) where the object may be located. The patient is asked to select the correct location of the object. The patient provides at least one response to the sensory stimulus by selecting one of the at least two locations on the touchscreen.

The location selected is compared to a predetermined standard of the correct location to determine whether an underlying memory association between the object and the selected location is desired. If the location selected is the correct location, then the underlying memory association is desired, and an electrical current with a beta frequency (e.g., 16 Hz) is generated and administered to the patient's scalp via at least one electrode pair to stimulate the PFC and/or the HPC.

If the location selected is not the correct location, then the underlying memory association is undesired, and an electrical current with a theta frequency (e.g., 4 Hz) is generated and administered to the patient's scalp via at least one electrode pair to stimulate the PFC and/or the HPC.

Alternatively, an electrical current may only be applied if the location selected is the correct location but not if the location selected is not the correct location. Similarly, an electric current may only be applied if the location selected is not the correct location but not if the location selected is the correct location. An electrical current may or may not be applied if the patient does not make a selection or the selection is determined to be neither correct nor incorrect.

The method may be repeated with the same object as the sensory stimulus or with one or more different objects as sensory stimuli. The method may be repeated as many times as wanted, with as many sensory stimuli as wanted.

Example 2

Some embodiments may be used to disrupt or weaken an undesired memory association. For example, post-traumatic stress disorder (PTSD) may have a severe effect on daily functioning. For example, patients with PTSD may suffer from intrusive and/or anxiety-invoking memories, usually based on a traumatic experience. When a memory is recalled, it becomes labile and must be "reconsolidated" back into long-term storage. Thus, some embodiments may be practiced by or with a PTSD patient (e.g., in the company of a therapist or medical provider) to weaken intrusive and/or anxiety-invoking associations by disrupting the brain rhythms that promote memory reconsolidation (or enhancing rhythms that promote forgetting) while the patient recalls the traumatic experience.

According to some embodiments, a system may be selected, calibrated, and/or customized for a particular PTSD patient. At least one electrode pair may be attached to or proximate to the patient's scalp with a conductive gel between each electrode and the scalp, each electrode being connected to at least one current generator. One or more sensors (e.g., a heart rate monitor) may also be attached to the patient to measure one or more physiological input signals.

An olfactory stimulus that triggers a memory of a traumatic experience (e.g., the scent of diesel gas) may be delivered to the patient. The patient provides at least one response to the sensory stimulus via one or more physiological input signals (e.g., heart rate) measured by the one or more sensors.

The one or more physiological input signals are processed and compared to a predetermined standard of one or more physiological parameters (e.g., a heart rate threshold value or a change in heart rate) to determine whether an underlying memory association between the olfactory stimulus and the one or more physiological parameters is desired. The one or more physiological parameters may be markers of stress. If the one or more physiological parameters are within one or more predetermined limits, then the underlying memory association is desired, and an electrical current with a beta frequency (e.g., 16 Hz) may be generated and administered to the patient's scalp via at least one electrode pair to stimulate the PFC and/or the HPC.

If the one or more physiological parameters fall outside the one or more predetermined limits, then the underlying memory association is undesired, and an electrical current with a theta frequency (e.g., 4 Hz) is generated and administered to the patient's scalp via at least one electrode pair to stimulate the PFC and/or the HPC. Since recalling a memory is known to render the memory temporarily labile—and susceptible to treatments that inhibit consolidation into long-term memory—stimulating the user with theta oscillations during a recall episode is likely to promote forgetting of the traumatic memory.

Alternatively, an electrical current may only be applied if the one or more physiological parameters fall outside the one or more predetermined limits but not if the one or more physiological parameters are within one or more predetermined limits. Similarly, an electric current may only be applied if the one or more physiological parameters are within one or more predetermined limits but not if the one or more physiological parameters fall outside the one or more predetermined limits. The method may be repeated as many times as wanted, with as many sensory stimuli as wanted.

Example 3

Researchers distinguish between recognition and recall memory. Recognition memory tasks require individuals to indicate whether they have encountered a stimulus (such as a picture or a word) before. Recall memory tasks require participants to retrieve previously learned information. For example, individuals might be asked to produce a series of actions they have seen before or to repeat a list of words they have heard before.

Some embodiments may be used to reinforce a desired memory association and/or weaken undesired memory associations. Associative learning has applications in schools, workplaces, homes, etc. For example, students may be required to remember large amounts of information in educational settings, on-the-job training settings, and high-stakes professional testing settings. Thus, some embodiments may be practiced by or with a student (e.g., in the company of a trainer, educator, or study partner) to enhance or disrupt memory.

According to some embodiments, a system may be selected, calibrated, and/or customized for a particular student. At least one electrode pair may be attached to or proximate to the student's scalp with a conductive gel between each electrode and the scalp, each electrode being connected to at least one current generator. According to some embodiments, the system provides transcranial electrical stimulation to boost endogenous beta or theta rhythms in the student's brain following correct or incorrect recall, respectively, of study/test material.

A student, trainer, educator, or study partner may select material from a set of pre-defined knowledge domains saved in local memory or in a remote server, or input custom material into the system via a software application program interface (API). In either case, the knowledge may consist of a set of facts. Each fact may be associated with a question or prompt (i.e., a stimulus), a correct answer (i.e., a predetermined standard), and optionally, a set of incorrect answers. Questions or prompts may be delivered to the student (e.g., "What is the Korean word for 'friendly'?" or simply, "friendly") serially, with a specific or random sequence. For example, typed questions (from/for, e.g., language tests, employment assessments, entrance/exit examinations, or licensing and certification examinations) may be delivered to the student via a computer monitor. The computer monitor also may present two or more answers (e.g., true/false or multiple choice). The student's response may be a selection (e.g., a selection with a pointing tool of "chin-han" from a list of multiple choices), a free response (e.g., speaking "chin-han" into a microphone), and/or a change in a physiological parameter of the student (e.g., a stress marker).

The system software would determine whether the response was correct or not. If correct, the system would provide a visual and/or auditory feedback signal to indicate this to the user, followed by sending a command to a current generator to produce a beta frequency stimulation. If incorrect, the system would provide a distinct visual and/or auditory feedback signal, followed by a command to produce a theta frequency stimulation. Optionally, the software could also monitor neural activity via a sensor, such as a scalp EEG electrode, and time the stimulator command so the synthetic oscillation is precisely aligned with the phase of the user's endogenous oscillations.

The response is compared to a predetermined standard of the correct answer (and may be a maximum response time period) to determine whether an underlying memory association between the question and response is desired. If the response is the correct answer (and is made within the maximum response time period), then the underlying memory association is desired, a feedback signal may indicate this to the student, and an electrical current with a beta frequency (e.g., 16 Hz) may be generated and administered to the student's scalp via at least one electrode pair to stimulate the PFC and/or the HPC.

If the response is not the correct answer (or is not made within the maximum response time period), then the underlying memory association is undesired, a distinct feedback signal may indicate this to the student, and an electrical current with a theta frequency (e.g., 4 Hz) may be generated and administered to the student's scalp via at least one electrode pair to stimulate the PFC and/or the HPC. For incorrect responses, the correct answer may be indicated subsequently, for example, after a short delay.

Alternatively, an electrical current may only be applied if the response is correct but not if the response is incorrect or too slow. Similarly, an electric current may only be applied if the response is incorrect or too slow but not if the response is correct. An electrical current may or may not be applied if the student does not respond or the response is determined to be neither correct nor incorrect (e.g., too slow).

The method may be repeated with the same question or with a series of different questions. The method may be repeated as many times as wanted, with as many sensory stimuli as wanted. The electrical stimulation may boost the user's endogenous brain rhythms following correct and incorrect response, thereby promoting learning of the study/test material.

CONCLUSION

While various inventive embodiments have been described and illustrated herein, those of ordinary skill in the art will readily envision a variety of other means and/or structures for performing the function and/or obtaining the results and/or one or more of the advantages described herein, and each of such variations and/or modifications is deemed to be within the scope of the inventive embodiments described herein. More generally, those skilled in the art will readily appreciate that all parameters, dimensions, materials, and configurations described herein are meant to be exemplary and that the actual parameters, dimensions, materials, and/or configurations will depend upon the specific application or applications for which the inventive teachings is/are used. Those skilled in the art will recognize, or be able to ascertain using no more than routine experimentation, many equivalents to the specific inventive embodiments described herein. It is, therefore, to be understood that the foregoing embodiments are presented by way of example only and that, within the scope of the appended claims and equivalents thereto, inventive embodiments may be practiced otherwise than as specifically described and claimed. Inventive embodiments of the present disclosure are directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the inventive scope of the present disclosure.

The above-described embodiments can be implemented in any of numerous ways. For example, embodiments of designing and making the embodiments disclosed herein may be implemented using hardware, software or a combination thereof. When implemented in software, the software code can be executed on any suitable processor or collection of processors, whether provided in a single computer or distributed among multiple computers.

Further, it should be appreciated that a computer may be embodied in any of a number of forms, such as a rack-mounted computer, a desktop computer, a laptop computer, or a tablet computer. Additionally, a computer may be embedded in a device not generally regarded as a computer but with suitable processing capabilities, including a Personal Digital Assistant (PDA), a smart phone or any other suitable portable or fixed electronic device.

Also, a computer may have one or more input and output devices. These devices can be used, among other things, to present a user interface. Examples of output devices that can be used to provide a user interface include printers or display screens for visual presentation of output and speakers or other sound generating devices for audible presentation of output. Examples of input devices that can be used for a user interface include keyboards, and pointing devices, such as mice, touch pads, and digitizing tablets. As another example, a computer may receive input information through speech recognition or in other audible format.

Such computers may be interconnected by one or more networks in any suitable form, including a local area network or a wide area network, such as an enterprise network, and intelligent network (IN) or the Internet. Such networks may be based on any suitable technology and may operate according to any suitable protocol and may include wireless networks, wired networks or fiber optic networks.

The various methods or processes (e.g., of designing and making the retention/delivery structure disclosed above) outlined herein may be coded as software that is executable on one or more processors that employ any one of a variety of operating systems or platforms. Additionally, such software may be written using any of a number of suitable programming languages and/or programming or scripting tools, and also may be compiled as executable machine language code or intermediate code that is executed on a framework or virtual machine.

Also, various inventive concepts may be embodied as one or more methods, of which an example has been provided. The acts performed as part of the method may be ordered in any suitable way. Accordingly, embodiments may be constructed in which acts are performed in an order different than illustrated, which may include performing some acts simultaneously, even though shown as sequential acts in illustrative embodiments.

All publications, patent applications, patents, and other references mentioned herein are incorporated by reference in their entirety.

All definitions, as defined and used herein, should be understood to control over dictionary definitions, definitions in documents incorporated by reference, and/or ordinary meanings of the defined terms.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of" or, when used in the claims, "consisting of" will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of" "only one of" or "exactly one of" "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

The invention claimed is:

1. A method for selectively reinforcing or weakening memory associations, the method comprising:
   delivering, via at least one output device, a first sensory stimulus to a user, wherein the first sensory stimulus includes at least one of a visual stimulus, an audio stimulus, or a tactile stimulus;
   registering, via at least one user input device, at least one response of the user to the first sensory stimulus, wherein the at least one response of the user to the first sensory stimulus is a selection of an indication of true or false, a selection of an answer from a plurality of presented answers, or a selection of a match to the first sensory stimulus from a plurality of presented matches;
   processing, via at least one processor in communication with the at least one output device and the at least one input device, the at least one response of the user to the first sensory stimulus to determine whether an underlying memory association between the first sensory stimulus and the at least one response is desired or undesired according to at least one predetermined standard;
   generating, via at least one current generator in communication with the at least one processor, an electrical current, the electrical current including a plurality of oscillating pulses with at least one predetermined frequency, the at least one predetermined frequency being set to:
      a beta frequency if the underlying memory association is desired; or
      a theta frequency if the underlying memory association is undesired; and
   administering, within about 1 second to about 10 seconds from the registration of the at least one response of the user to the first sensory stimulus, the electrical current via at least one electrode pair detachably attached to or proximate to the user's scalp to stimulate at least one specific portion of the user's brain with the electrical current based at least in part on the at least one response of the user to the first sensory stimulus so as to reinforce or weaken the underlying memory association.

2. The method of claim 1, wherein the current generator draws about 5-20 volts from a low voltage source.

3. The method of claim 1, wherein the electrical current has a current flow of about 0.25-1.5 milli-amps.

4. The method of claim 1, further comprising regulating, via the at least one processor, an amplitude of the electrical current.

5. The method of claim 1, wherein the at least one output device for delivering the first sensory stimulus to the user includes at least one of a visual display, a printer, a refreshable tactile display, and a speaker.

6. The method of claim 1, wherein the first sensory stimulus includes at least one of a digital image, an alphanumeric character, a braille character, and an audible sound.

7. The method of claim 1, wherein the first sensory stimulus includes an objective assessment question, wherein the objective assessment question requires the user to provide the at least one response via the at least one input device.

8. The method of claim 1, wherein the first sensory stimulus includes an objective assessment question, wherein the objective assessment question requires the user to supply at least one of an alphanumeric character, a braille character, and an audible sound via the at least one input device.

9. The method of claim 1, wherein the at least one input device for registering at least one response of the user to the first sensory stimulus includes at least one of a keyboard, a scanner, a microphone, a pointing device, a touchscreen, a webcam, and a refreshable tactile display.

10. The method of claim 1, wherein the at least one response of the user to the first sensory stimulus is at least one of an alphanumeric character, a braille character, and an audible sound.

11. The method of claim 1, wherein the at least one response of the user to the first sensory stimulus further relates to a change in a physiological parameter of the user, the physiological parameter relating to at least one of a heart rate, a blood pressure, a body temperature, a respiration rate, a neural activation, and a neural oscillation.

12. The method of claim 1, wherein registering the at least one response of the user to the first sensory stimulus further includes at least one of detecting and measuring, via at least one sensor, at least one physiological input signal from the user.

13. The method of claim 1, wherein the at least one input device for registering the at least one response of the user to the first sensory stimulus includes at least one of a heart rate monitor, an ECG system, a blood pressure monitor, a respiration rate monitor, a thermometer, an fMRI system, an EEG system, and an MEG system.

14. The method of claim 1, further comprising at least one of detecting and measuring, via at least one sensor, at least one physiological input signal from the user.

15. The method of claim 1, further comprising:
   at least one of detecting and measuring, via at least one sensor, at least one physiological input signal from the user; and
   electronically converting, via an analog-to-digital converter coupled to the at least one sensor, the at least one physiological input signal from the at least one sensor to a plurality of digital samples of the at least one physiologic signal relating to at least one physiological parameter.

16. The method of claim 1, wherein the at least one specific portion of the user's brain is at least one of the prefrontal cortex, the hippocampus, and an associated structure of the limbic system.

17. The method of claim 1, wherein the at least one electrode pair is a plurality of electrode pairs.

18. The method of claim 1, wherein each electrode of the at least one electrode pair is a transcranial alternating current electrode.

19. The method of claim 1, further comprising attaching the at least one electrode pair to or proximate to the user's scalp.

20. The method of claim 1, further comprising applying at least one of a conductive gel and a conductive paste between each electrode of the at least one electrode pair and the user's scalp to reduce impedance.

21. The method of claim 1, further comprising at least one of selecting, calibrating, and customizing for the user at least one of:
the at least one output device;
the at least one input device;
a placement of the at least one electrode pair;
a type of the first sensory stimulus;
a content of the first sensory stimulus;
a type of the at least one response to the first sensory stimulus;
the at least one predetermined standard;
an amplitude of the electrical current; and
the at least one predetermined frequency.

22. The method of claim 1, wherein the at least one predetermined standard includes a correct response to an associated sensory stimulus.

23. The method of claim 1, wherein determining whether an underlying memory association is desired or undesired comprising comparing the at least one response of the user to the at least one predetermined standard.

24. The method of claim 1, wherein the beta frequency is a frequency between about 12 Hz and about 40 Hz.

25. The method of claim 1, wherein the beta frequency is about 16 Hz.

26. The method of claim 1, wherein the theta frequency is a frequency between about 3 Hz and about 8 Hz.

27. The method of claim 1, wherein the theta frequency is about 4 Hz.

28. The method of claim 1, wherein the method is used for computer-based learning.

29. The method of claim 1, wherein the method is used to administer treatment to a patient with at least one of a learning disability, a memory disorder, and a stress disorder.

30. A method for selectively weakening memory associations, the method comprising:
delivering, via at least one output device, a first sensory stimulus to a user, wherein the first sensory stimulus includes at least one of a visual stimulus, an audio stimulus, or a tactile stimulus;
registering, via at least one user input device, at least one response of the user to the first sensory stimulus, wherein the at least one response of the user to the first sensory stimulus is a selection of an indication of true or false, a selection of an answer from a plurality of presented answers, or a selection of a match to the first sensory stimulus from a plurality of presented matches;
processing, via at least one processor in communication with the at least one output device and the at least one input device, the at least one response of the user to the first sensory stimulus to determine that an underlying memory association between the first sensory stimulus and the at least one response is undesired according to at least one predetermined standard; and
in response to determining that the underlying memory association is undesired:
generating, via at least one current generator in communication with the at least one processor, an electrical current, the electrical current including a plurality of oscillating pulses with at least one predetermined frequency, the at least one predetermined frequency being set to a theta frequency; and
administering, within about 1 second to about 10 seconds from the registration of the at least one response of the user to the first sensory stimulus, the electrical current via at least one electrode pair detachably attached to or proximate to the user's scalp to stimulate at least one specific portion of the user's brain with the electrical current based at least in part on the at least one response of the user to the first sensory stimulus so as to weaken the underlying memory association.

31. A method for selectively reinforcing memory associations, the method comprising:
delivering, via at least one output device, a first sensory stimulus to a user, wherein the first sensory stimulus includes at least one of a visual stimulus, an audio stimulus, or a tactile stimulus;
registering, via at least one user input device, at least one response of the user to the first sensory stimulus, wherein the at least one response of the user to the first sensory stimulus is a selection of an indication of true or false, a selection of an answer from a plurality of presented answers, or a selection of a match to the first sensory stimulus from a plurality of presented matches;
processing, via at least one processor in communication with the at least one output device and the at least one input device, the at least one response of the user to the first sensory stimulus to determine that an underlying memory association between the first sensory stimulus and the at least one response is desired according to at least one predetermined standard; and
in response to determining that the underlying memory association is desired:
generating, via at least one current generator in communication with the at least one processor, an electrical current, the electrical current including a plurality of oscillating pulses with at least one predetermined frequency, the at least one predetermined frequency being set to a beta frequency; and
administering, within about 1 second to about 10 seconds from the registration of the at least one response of the user to the first sensory stimulus, the electrical current via at least one electrode pair detachably attached to or proximate to the user's scalp to stimulate at least one specific portion of the user's brain with the electrical current based at least in part on the at least one response of the user to the first sensory stimulus so as to reinforce the underlying memory association.

* * * * *